(12) United States Patent
Annis et al.

(10) Patent No.: US 8,513,431 B2
(45) Date of Patent: Aug. 20, 2013

(54) METHOD FOR PREPARING 5-HALOALKYL-4, 5-DIHYDROISOXAZOLE DERIVATIVES

(75) Inventors: Gary David Annis, Landenberg, PA (US); Brenton Todd Smith, Exton, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/544,113

(22) Filed: Jul. 9, 2012

(65) Prior Publication Data
US 2012/0277442 A1 Nov. 1, 2012
US 2013/0165663 A9 Jun. 27, 2013

Related U.S. Application Data

(62) Division of application No. 12/679,382, filed as application No. PCT/US2008/072074 on Aug. 4, 2008, now Pat. No. 8,217,180.

(60) Provisional application No. 61/080,454, filed on Jul. 14, 2008, provisional application No. 61/043,459, filed on Apr. 9, 2008, provisional application No. 60/965,115, filed on Aug. 17, 2007.

(51) Int. Cl.
*C07D 261/04* (2006.01)
*C07C 233/00* (2006.01)

(52) U.S. Cl.
USPC .......................................... 548/240; 564/123

(58) Field of Classification Search
USPC .......................................... 548/240; 564/123
See application file for complete search history.

(56) References Cited

U.S. PATENT DOCUMENTS

| | | | |
|---|---|---|---|
| 3,879,532 A | 4/1975 | Hass et al. | |
| 4,129,568 A | 12/1978 | Howe | |
| 6,645,984 B2 | 11/2003 | Braun et al. | |
| 7,662,972 B2 | 2/2010 | Mita et al. | |
| 7,897,630 B2 | 3/2011 | Lahm et al. | |
| 7,947,715 B2 | 5/2011 | Mita et al. | |
| 7,951,828 B1 | 5/2011 | Mita et al. | |
| 8,022,089 B2 | 9/2011 | Mita et al. | |
| 8,138,213 B2 | 3/2012 | Mita et al. | |
| 8,217,180 B2 | 7/2012 | Annis et al. | |
| 8,231,888 B2 | 7/2012 | Lahm et al. | |
| 2005/0250822 A1 | 11/2005 | Mita et al. | |
| 2007/0066617 A1 | 3/2007 | Mita et al. | |
| 2009/0023923 A1 | 1/2009 | Mizukoshi et al. | |
| 2009/0133319 A1 | 5/2009 | Lahm et al. | |
| 2009/0143410 A1 | 6/2009 | Patel | |
| 2010/0137612 A1 | 6/2010 | Yaosaka et al. | |
| 2010/0173948 A1 | 7/2010 | Lahm et al. | |
| 2010/0179195 A1 | 7/2010 | Lahm et al. | |
| 2010/0249424 A1 | 9/2010 | Annis et al. | |
| 2010/0254959 A1 | 10/2010 | Lahm et al. | |
| 2010/0254960 A1 | 10/2010 | Long et al. | |
| 2011/0059988 A1 | 3/2011 | Heckeoth et al. | |

FOREIGN PATENT DOCUMENTS

| | | |
|---|---|---|
| CA | 2252543 | 11/1997 |
| CA | 2558848 | 9/2005 |
| CN | 101346336 | 1/2009 |
| EA | 000924 | 6/2000 |
| EP | 1538138 | 6/2005 |
| EP | 1731512 | 12/2006 |
| EP | 1975149 | 10/2008 |
| EP | 2172462 | 4/2010 |
| EP | 1973888 | 1/2011 |
| GB | 2351081 | 12/2000 |
| JP | 199859944 | 3/1998 |
| JP | 1999503114 | 3/1999 |
| JP | 2004529130 | 9/2004 |
| JP | 2005272452 | 10/2005 |
| JP | 2007016017 | 1/2007 |
| JP | 2007106756 | 4/2007 |
| KZ | 13246 | 7/2003 |
| KZ | 16356 | 10/2005 |

(Continued)

OTHER PUBLICATIONS

Konno et al., "Palladium-Catalyzed Regio- and Stereoselective Formate Reduction of Fluorine-Containing Allylic Mesylates. A New Entry for the Construction of a Tertiary Carbon Attached with a Fluoroalkyl Group," Journal of Organic Chemistry (2006) 71(9):3545-3550.

(Continued)

*Primary Examiner* — Golam M M Shameem
(74) *Attorney, Agent, or Firm* — Pepper Hamilton LLP

(57) ABSTRACT

Disclosed is a method for preparing a compound of Formula 1

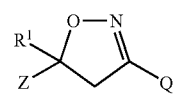

wherein
$R^1$ is $CHX_2$, $CX_3$, $CX_2CHX_2$ or $CX_2CX_3$;
each X is independently Cl or F;
Z is optionally substituted phenyl; and
Q is phenyl or 1-naphthalenyl, each optionally substituted as defined in the disclosure; comprising contacting a compound of Formula 2

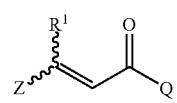

with hydroxylamine in the presence of a base.
The present invention also relates to novel compounds of Formula 2, useful as starting materials for the aforedescribed method.

17 Claims, No Drawings

(56) References Cited

FOREIGN PATENT DOCUMENTS

| | | |
|---|---|---|
| RU | 99101948 | 10/2001 |
| RU | 2433123 | 11/2011 |
| WO | 2004099197 | 11/2004 |
| WO | 2005085216 | 6/2005 |
| WO | 2005094329 | 10/2005 |
| WO | 2006135640 | 12/2006 |
| WO | 2007026985 | 3/2007 |
| WO | 20070070606 | 6/2007 |
| WO | 2007074789 | 7/2007 |
| WO | 2007075459 | 7/2007 |
| WO | 2007079162 | 7/2007 |
| WO | 2007105814 | 9/2007 |
| WO | 2007123855 | 11/2007 |
| WO | 2007125984 | 11/2007 |
| WO | 2008019760 | 2/2008 |
| WO | 2008108448 | 9/2008 |
| WO | 2008122375 | 10/2008 |
| WO | 2008154528 | 12/2008 |
| WO | 2009001942 | 12/2008 |
| WO | 2009002809 | 12/2008 |
| WO | 2009003075 | 12/2008 |
| WO | 2009025983 | 2/2009 |
| WO | 2009035004 | 3/2009 |
| WO | 2009045999 | 4/2009 |

OTHER PUBLICATIONS

Carey et al., "Advanced Organic Chemistry," 2ed., Part B: Reactions and Synthesis, (1983) Pelenum Press, New York.

Sosnovskil et al., "Ketone-ketone condensation with participation of polyhaloalkyl phenyl ketones," Journal of Organic Chemistry of the USSR, (1992) 28:420-426.

Kamble et al., "An efficient synthesis of pharmacologically active derivatives 1,3,4-Oxadiazoles," Journal of Heterocyclic Chemistry (2006) 43(345):345-352.

Database Chemical Abstracts Service (1988) XP002516318, Database accession No. 111:115084.

Regaila et al.. "Newer heterocycles and carbamates from naphthyl," Egyptian Journal of Pharmaceutical Sciences (1988) 29(1-4): 71-87.

Database Chemical Abstracts Service (1996) XP002516333, Database Accession No. 126:31303.

Kuznetsova et al., "Synthesis of fluorine-containing functlonalized isoxazolines," Russian Chemical Bulletin (1996) 45 (5):1245-1246.

Notice of Allowance dated Jan. 11, 2011 received in copending U.S. Appl. No. 12/086,935.

Notice of Allowance dated Sep. 28, 2010 received in copending U.S. Appl. No. 12/086,935.

Notice of Allowance dated Oct. 21, 2010 received in copending U.S. Appl. No. 12/083,944.

Non-final Office Action dated May 19, 2010 received in copending U.S. Appl. No. 12/083,944.

Non-final Office Action dated Dec. 16, 2009 received in copending U.S. Appl. No. 12/083,944.

Non-final Office Action dated Aug. 3, 2009 received in copending U.S. Appl. No. 12/083,944.

Dighade et al,. "Effect of solvents in synthesis of new 4-(2-hydroxy-5-methylphenyl)-6-aryl-2-Imino-6H-2,3-dihydro-1,3-thiazines," Asian Journal of Chemistry (2001) 13(4):1560-1564.

International Search Report dated Feb. 24, 2011 received in copending International Application No. PCT/US2009/039832.

Non-final Office Action dated Nov. 28, 2011 received in copending U.S. Appl. No. 12/663,751.

Lahm et al. (2007): STN International HAPLUS database, Columbus (OH), accession No. 2007:755410.

Motoki et al., "Cooper(I) alkoxide-catalyzed alkynylation of trifluoromethyl ketones," Organic Letters (2007) 9 (16):2997-3000.

Mita et al. (2007): STN International HCAPLUS database, (Columbus, Ohio), Accession No. 2009:740002.

Office Action dated Jan. 23, 2012 received in copending U.S. Appl. No. 12/667,927.

Office Action dated Feb. 6, 2012 received in copending U.S. Appl. No. 12/602,821.

Notice of Allowance dated Feb. 8, 2012 received in copending U.S. Appl. No. 12/663,848.

Notice of Allowance and Fee(s) due dated Mar. 18, 2012 received in pending U.S. Appl. No. 12/679,382.

Advisory Action dated Sep. 6, 2012 received in copending U.S. Appl. No. 12/677,927.

Notice of Allowance dated Sep. 24, 2012 received in copending U.S. Appl. No. 12/677,927.

[Kuznetsova et al., "Synthesis of fluorine-containing functionalized Isoxazolines," Proceedings of the Academy of Sciences (1996) 5:1306.1307]. English Translation of Russian Office Acton received Jul. 3, 2012 attached.

Mita at al. (2007): STN International HCAPLUS database, (Columbus, Ohio). Accession No. 2007:330406.

Office Action dated Jun. 8, 2012 received in copending U.S. Appl. No. 12/663,848.

Office Action dated Jun. 26, 2012 received in pending U.S. Appl. No. 12/602,821.

Office Action dated Jun. 8, 2012 received in copending U.S. Appl. No. 12/663,751.

Office Action dated Jul. 2, 2012 received in copending U.S. Appl. No. 12/677,927.

Office Action dated Aug. 14, 2012 received in copending U.S. Appl. No. 12/933,493.

Notice of Allowance dated Mar. 21, 2012 received in copending U.S. Appl. No. 13/156,653.

Office Action dated Sep. 21, 2011 received in counterpart U.S. Appl. No. 13/156,653.

Office Action dated Nov. 23, 2012 received in counterpart U.S. Appl. No. 13/561,546.

Notice of Allowance dated Nov. 14, 2012 received in counterpart U.S. Appl. No. 12/663,751.

Final Office Action dated Jan. 28, 2013 received in copending U.S. Appl. No. 12/663,848.

Final Office Action dated Mar. 13, 2013 received in copending U.S. Appl. No. 12/602,821.

Notice of Allowance dated Jun. 7, 2013 received in copending U.S. Appl. No. 13/561,546.

Notice of Allowance dated May 14, 2013 received in copending U.S. Appl. No. 12/933,493.

METHOD FOR PREPARING 5-HALOALKYL-4, 5-DIHYDROISOXAZOLE DERIVATIVES

CROSS-REFERENCE TO RELATED APPLICATIONS

This application is a U.S. Divisional Application filing of U.S. patent application Ser. No. 12/679,382, filed Mar. 22, 2010, issued Jul. 10, 2012 as U.S. Pat. No. 8,217,180, which is a U.S. National Stage Entry of PCT/US08/72074, filed Aug. 4, 2008 which claims priority to U.S. Provisional Application No. 61/080,454, filed Jul. 14, 2008, U.S. Provisional Application No. 61/043,459, filed Apr. 9, 2008, and U.S. Provisional Application No. 60/965,115, filed Aug. 17, 2007, each of which is incorporated herein by reference in its entirety.

FIELD OF THE INVENTION

The present invention pertains to a method for the preparation of 5-haloalkyl-4,5-dihydroisoxazole derivatives. The present invention also relates to novel enones useful as starting materials for the aforedescribed method.

SUMMARY OF THE INVENTION

The present invention relates to a method for preparing a compound of Formula 1

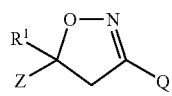

1 wherein
- $R^1$ is $CHX_2$, $CX_3$, $CX_2CHX_2$ or $CX_2CX_3$;
- each X is independently Cl or F;
- Z is optionally substituted phenyl;
- Q is $Q^a$ or $Q^b$;
- $Q^a$ is phenyl substituted with one $Q^1$ and optionally substituted with one to four substituents independently selected from $R^3$;
- $Q^1$ is a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —CN, —NO$_2$, —N(R$^4$)R$^5$, —C(=W)N(R$^4$)R$^5$, —C(=O)OR$^5$ and $R^7$;
- $Q^b$ is optionally substituted 1-naphthalenyl;
- each $R^3$ is independently halogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ haloalkynyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_2$-$C_7$ alkylcarbonyl, $C_2$-$C_7$ haloalkylcarbonyl, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —N(R$^4$)R$^5$, —C(=W)N(R$^4$)R$^5$, —C(=W)OR$^5$, —CN, —OR$^{11}$ or —NO$_2$; or a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —CN, —NO$_2$, —N(R$^4$)R$^5$, —C(=W)N(R$^4$)R$^5$, —C(=O)OR$^5$ and $R^7$;
- each $R^4$ is independently H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;
- each $R^5$ is independently H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;
- each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ halodialkylaminocarbonyl, —OH, —NH$_2$, —CN or —NO$_2$; or $Q^2$;
- each $R^7$ is independently a phenyl ring or a pyridinyl ring, each ring optionally substituted with one or more substituents independently selected from $R^8$;
- each $R^8$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkylcarbonyl, $C_2$-$C_4$ alkoxycarbonyl, $C_2$-$C_7$ alkylaminocarbonyl, $C_3$-$C_7$ dialkylaminocarbonyl, —OH, —NH$_2$, —C(=O)OH, —CN or —NO$_2$;
- each $Q^2$ is independently a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —NO$_2$, —C(=W)N(R$^9$)R$^{10}$ and —C(=O)OR$^{10}$;
- each $R^9$ is independently H, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;
- each $R^{10}$ is independently H; or $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl;
- each $R^{11}$ is independently H; or $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl, $C_2$-$C_7$ alkoxycarbonyl, $C_1$-$C_6$ alkylsulfonyl or $C_1$-$C_6$ haloalkylsulfonyl; and
- each W is independently O or S;

comprising contacting a compound of Formula 2

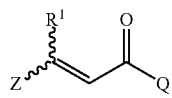

wherein R¹, Q and Z are as previously defined for Formula 1, with hydroxylamine in the presence of a base.

The present invention also relates to novel compounds of Formula 2, useful as starting materials for the aforedescribed method.

DETAILS OF THE INVENTION

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

Ratios are generally recited herein as single numbers, which are relative to the number 1; for example, a ratio of 4 means 4:1. The term "equivalent ratio" refers to the number of equivalents of one component (e.g., of a base) relative to another component added to a reaction mixture, recognizing that some compounds may provide two or more equivalents per mole.

In the present disclosure and claims, the radical "$SO_2$" means sulfonyl, "—CN" means cyano, "—$NO_2$" means nitro, and "—OH" means hydroxyl.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(=O)$—, $CH_3CH_2S(=O)$—, $CH_3CH_2CH_2S(=O)$—, $(CH_3)_2CHS(=O)$— and the different butylsulfinyl, pentyl-sulfinyl and hexylsulfinyl isomers. Examples of "alkylsulfonyl" include $CH_3SO_2$—, $CH_3CH_2SO_2$—, $CH_3CH_2CH_2SO_2$—, $(CH_3)_2CHSO_2$—, and the different butylsulfonyl, pentylsulfonyl and hexylsulfonyl isomers.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$—, $ClCH_2$—, $CF_3CH_2$— and $CF_3CCl_2$—. The terms "haloalkoxy" and "haloalkylthio" and the like, are defined analogously to the term "haloalkyl". Examples of "haloalkoxy" include $CF_3O$—, $CCl_3CH_2O$—, $HCF_2CH_2CH_2O$— and $CF_3CH_2O$—. Examples of "haloalkylthio" include $CCl_3S$—, $CF_3S$—, $CCl_3CH_2S$— and $ClCH_2CH_2CH_2S$—. Examples of "haloalkylsulfinyl" include $CF_3S(=O)$—, $CCl_3S(=O)$—, $CF_3CH_2S(=O)$— and $CF_3CF_2S(=O)$—. Examples of "haloalkylsulfonyl" include $CF_3SO_2$—, $CCl_3SO_2$—, $CF_3CH_2SO_2$— and $CF_3CF_2SO_2$—.

"Alkylcarbonyl" denotes a straight-chain or branched alkyl moieties bonded to a C(=O) moiety. Examples of "alkylcarbonyl" include $CH_3C(=O)$—, $CH_3CH_2CH_2C(=O)$— and $(CH_3)_2CHC(=O)$—. Examples of "alkoxycarbonyl" include $CH_3OC(=O)$—, $CH_3CH_2OC(=O)$—, $CH_3CH_2CH_2OC(=O)$—, $(CH_3)_2CHOC(=O)$— and the different butoxy-, pentoxy-, or hexoxycarbonyl isomers.

The total number of carbon atoms in a substituent group is indicated by the "$C_i$-$C_j$" prefix where i and j are numbers from 1 to 7. For example, $C_1$-$C_4$ alkylsulfonyl designates methylsulfonyl through butylsulfonyl.

When a compound is substituted with a substituent bearing a subscript that indicates the number of said substituents can exceed 1, said substituents (when they exceed 1) are independently selected from the group of defined substituents, e.g., $(R^v)_r$ in U-1 of Exhibit 1 wherein v is 0, 1, 2, 3, 4 or 5. As $(R^v)_r$ are optional substituents on rings in Exhibits 1 and 2, Q-A and Q-B respectively, each may substitute any available carbon or nitrogen ring member(s) of the rings. When a variable group is shown to be optionally attached to a position, for example $(R^v)^r$ wherein v may be 0, then hydrogen may be at the position even if not recited in the variable group definition. When one or more positions on a group are said to be "not substituted" or "unsubstituted", then hydrogen atoms are attached to take up any free valency.

The term "heterocyclic ring" denotes a ring in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. The term "unsaturated heterocyclic ring" relates to both partially and fully unsaturated rings. When a fully unsaturated heterocyclic ring satisfies Hückel's rule, then said ring is also called a "heteroaromatic ring" or "aromatic heterocyclic ring". Unless otherwise indicated, heterocyclic rings can be attached through any available carbon or nitrogen by replacement of a hydrogen on said carbon or nitrogen. A "heterocyclic ring" may optionally contain ring members selected from the group C(=O), C(=S), S(=O) and SO$_2$. The term "ring member" refers to any atom or other moiety (e.g., C(=O), C(=S), S(=O) or SO$_2$) forming the backbone of a ring.

"Aromatic" indicates that each of the ring atoms is essentially in the same plane and has a p-orbital perpendicular to the ring plane, and in which (4p+2)π electrons, where p is a positive integer, are associated with the ring to comply with Hückel's rule.

As is generally known in the art, the chemical name "pyridyl" is synonymous with "pyridinyl".

The term "optionally substituted" is used herein interchangeably with the phrase "substituted or unsubstituted" or with the term "(un)substituted". Unless otherwise indicated, an optionally substituted group may have a substituent at each substitutable position of the group, and each substitution is independent of the other. An optionally substituted group also may have no substituents. Therefore the phrase "optionally substituted with one or more substituents" means that the number of substituents may vary from zero up to the number of available positions for substitution. Similarly the phrase "optionally substituted with 1-5 substituents" means that the number of substituents may vary from zero up to the number of available position but not exceeding 5.

Each X is independently Cl or F. Thus, for example, CHX$_2$ could be CHCl$_2$, CHF$_2$ or CHClF.

When Q$^1$ or Q$^2$ is a nitrogen-containing heterocyclic ring it may be attached to the remainder of Formula 1 though any available carbon or nitrogen ring atom, unless otherwise described. As noted above, Q$^1$ and Q$^2$ can be (among others) phenyl optionally substituted with one or more substituents selected from a group of substituents as defined in the Summary of Invention. An example of phenyl optionally substituted with one to five substituents is the ring illustrated as U-1 in Exhibit 1, wherein R$^v$ is the optional substituents as defined in the Summary of the Invention for Q$^1$ and Q$^2$ and r is an integer from 0 to 5.

As noted above, Q$^1$ and Q$^2$ can be a 5- or 6-membered heterocyclic ring, which may be saturated or unsaturated, optionally substituted with one or more substituents selected from a group of substituents as defined in the Summary of Invention. Examples of a 5- or 6-membered aromatic unsaturated heterocyclic ring optionally substituted with one or more substituents include the rings U-2 through U-61 illustrated in Exhibit 1 wherein R$^v$ is any substituent as defined in the Summary of the Invention for Q$^1$ and Q$^2$ and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by (R$^v$)$_r$.

Exhibit 1

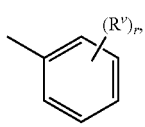
U-1

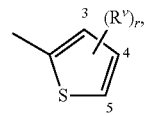
U-2

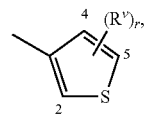
U-3

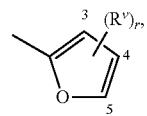
U-4

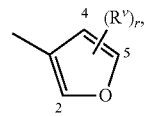
U-5

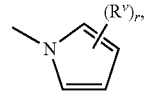
U-6

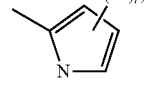
U-7

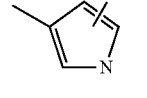
U-8

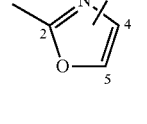
U-9

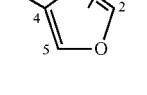
U-10

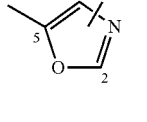
U-11

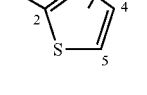
U-12

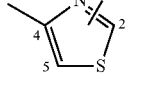
U-13

-continued
U-14 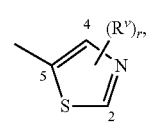
U-15 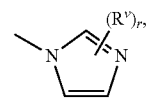
U-16 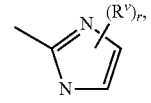
U-17 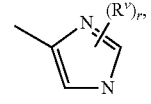
U-18 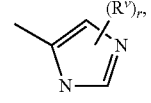
U-19 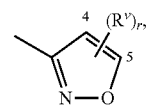
U-20 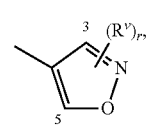
U-21 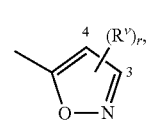
U-22 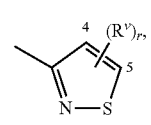
U-23 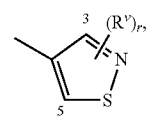
U-24 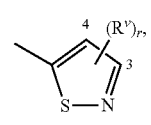
U-25 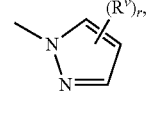
U-26 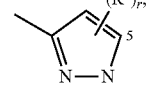
-continued
U-27 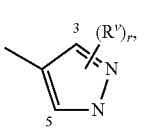
U-28 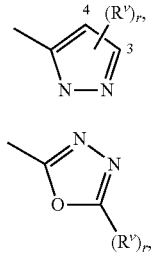
U-29 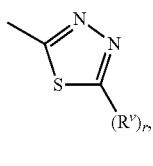
U-30 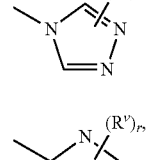
U-31 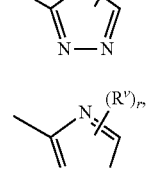
U-32 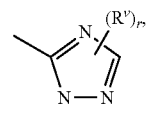
U-33 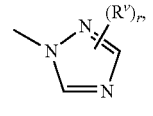
U-34 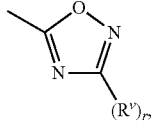
U-35 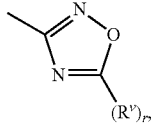
U-36 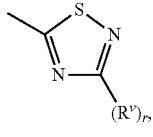
U-37
U-38

-continued
U-39 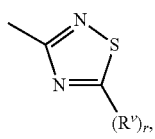
U-40 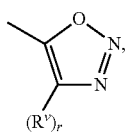
U-41 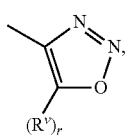
U-42 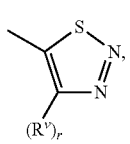
U-43 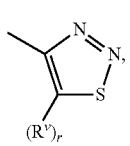
U-44 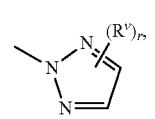
U-45 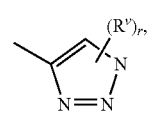
U-46 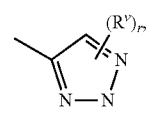
U-47 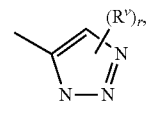
U-48 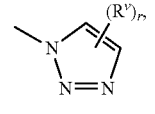
U-49 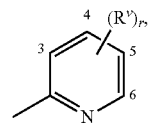
U-50 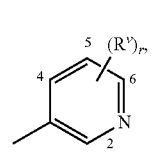
-continued
U-51 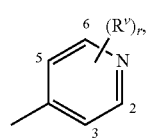
U-52 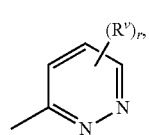
U-53 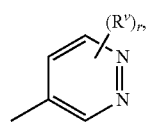
U-54 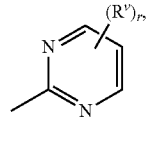
U-55 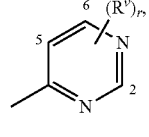
U-56 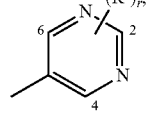
U-57 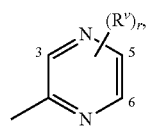
U-58 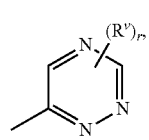
U-59 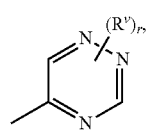
U-60 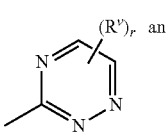
and
U-61 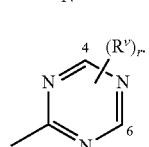
Note that when $Q^1$ or $Q^2$ is a 5- or 6-membered saturated or non-aromatic unsaturated heterocyclic ring optionally substituted with one or more substituents selected from the group of substituents as defined in the Summary of Invention for $Q^1$ and $Q^2$, one or two carbon ring members of the heterocycle can optionally be in the oxidized form of a carbonyl moiety.

Examples of a 5- or 6-membered saturated or non-aromatic unsaturated heterocyclic ring include the rings G-1 through G-35 as illustrated in Exhibit 2. Note that when the attachment point on the G group is illustrated as floating, the G group can be attached to the remainder of Formula 1 through any available carbon or nitrogen of the G group by replacement of a hydrogen atom. The optional substituents corresponding to $R^v$ can be attached to any available carbon or nitrogen by replacing a hydrogen atom. For these G rings, r is typically an integer from 0 to 4, limited by the number of available positions on each G group.

Note that when $Q^1$ and $Q^2$ comprise a ring selected from G-28 through G-35, $G^2$ is selected from O, S or N. Note that when $G^2$ is N, the nitrogen atom can complete its valence by substitution with either H or the substituents corresponding to $R^v$ as defined in the Summary of Invention for $Q^1$ and $Q^2$.

Exhibit 2

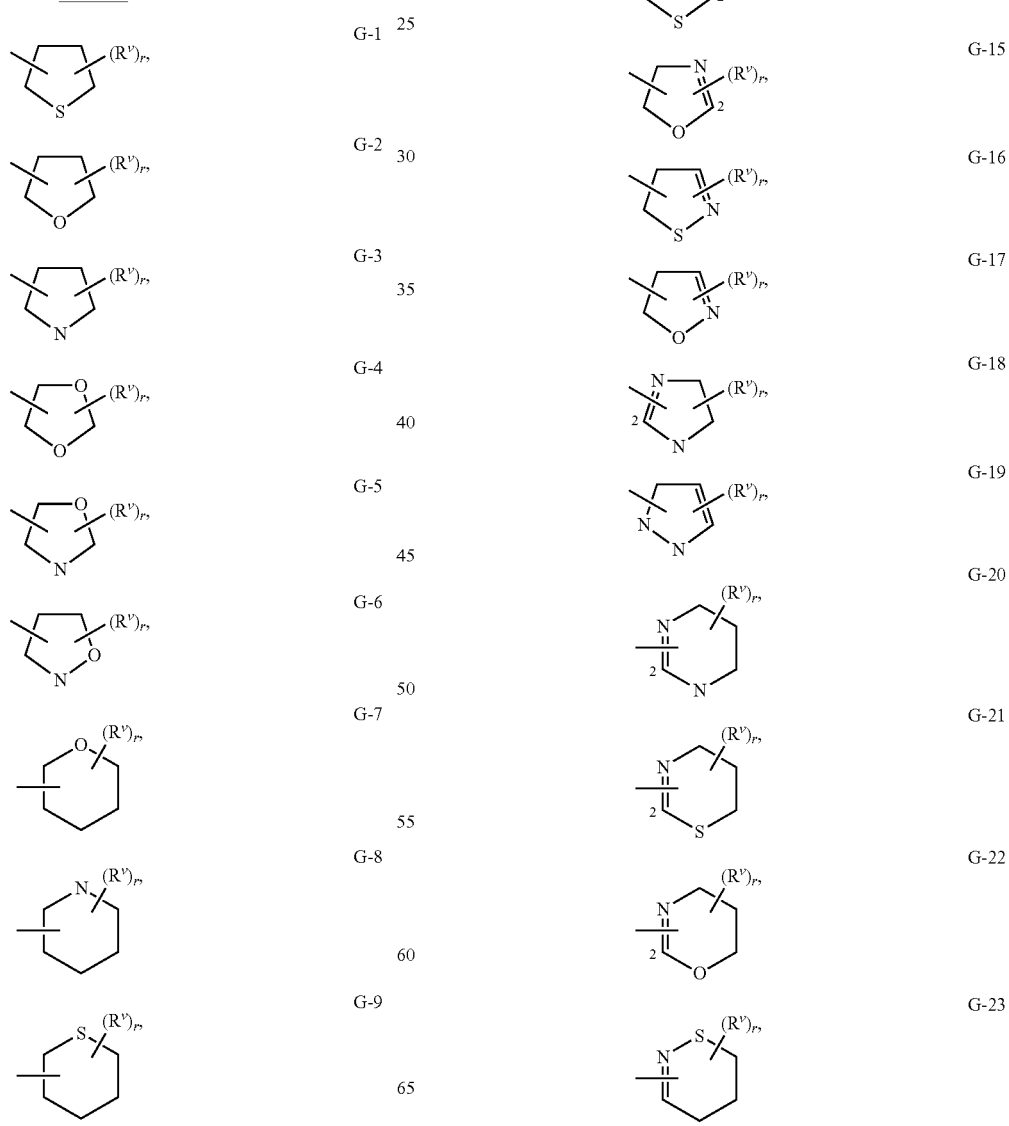

G-24 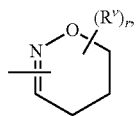

G-25 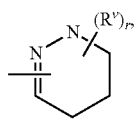

G-26 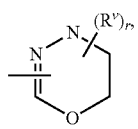

G-27 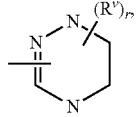

G-28 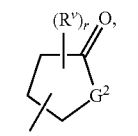

G-29 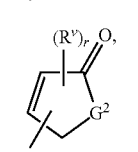

G-30 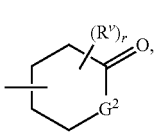

G-31 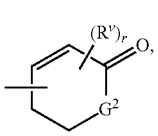

G-32 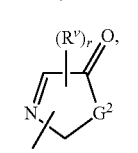

G-33 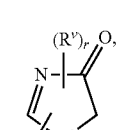

G-34 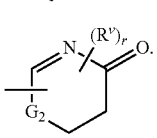 and

G-35 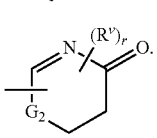

Embodiments of the present invention include:

Embodiment 1. The method described in the Summary of the Invention for preparing a compound of Formula 1 comprising contacting a compound of Formula 2 with hydroxylamine in the presence of a base wherein Z is phenyl optionally substituted with one to five substituents independently selected from $R^2$ (i.e.

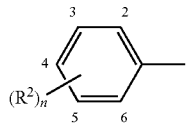

wherein n is 0, 1, 2, 3, 4 or 5); and
each $R^2$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylamino, $C_2$-$C_6$ dialkylamino, —CN or —$NO_2$.

Embodiment 1A. The method of Embodiment 1 wherein Z is phenyl substituted with one to three substituents independently selected from $R^2$, said substituents attached at the 3-, 4- or 5-positions of the phenyl ring.

Embodiment 1B. The method of Embodiment 1 or 1A wherein each $R^2$ is independently F, Cl, Br, $C_1$-$C_6$ alkyl, $C_1$-$C_6$ fluoroalkyl, $C_1$-$C_6$ alkoxy, $C_1$-$C_6$ fluoroalkoxy, $C_1$-$C_6$ alkylthio or $C_1$-$C_6$ fluoroalkylthio.

Embodiment 1C. The method of Embodiment 1 or 1A wherein each $R^2$ is independently halogen, $C_1$-$C_6$ alkyl, $C_1$-$C_6$ haloalkyl or —CN.

Embodiment 1D. The method of Embodiment 1C wherein each $R^2$ is independently halogen or $C_1$-$C_6$ haloalkyl.

Embodiment 1E. The method of Embodiment 1C wherein each $R^2$ is independently halogen or $CF_3$.

Embodiment 1F. The method of Embodiment 1E wherein each $R^2$ is independently F, Cl or $CF_3$.

Embodiment 1G. The method of Embodiment 1A wherein Z is

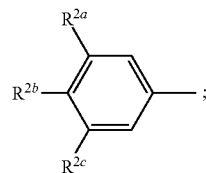

$R^{2a}$ is halogen, $C_1$-$C_2$ haloalkyl or $C_1$-$C_2$ haloalkoxy; $R^{2b}$ is H, halogen or cyano; and $R^{2c}$ is H, halogen or $CF_3$.

Embodiment 1H. The method of Embodiment 1G wherein $R^{2a}$ is $CF_3$ or halogen; and $R^{2c}$ is H, $CF_3$ or halogen.

Embodiment 1I. The method of Embodiment 1H wherein $R^{2a}$ is $CF_3$.

Embodiment 1J. The method of any one of Embodiments 1G through 1I wherein $R^{2b}$ is H.

Embodiment 1K. The method of any one of Embodiments 1G through 1J wherein $R^2$ is $CF_3$ or halogen.

Embodiment 1L. The method of Embodiment 1K wherein $R^{2c}$ is $CF_3$, F, Cl or Br.

Embodiment 1M. The method of Embodiment 1L wherein $R^{2c}$ is F, Cl or Br.

Embodiment 1N. The method of Embodiment 1L wherein $R^{2c}$ is $CF_3$, Cl or Br.

Embodiment 1O. The method of Embodiment 1N wherein $R^{2c}$ is Cl or Br.

Embodiment 1P. The method of Embodiment 1O wherein $R^{2b}$ is H and $R^{2c}$ is Cl.

Embodiment 1Q. The method of Embodiment 1O wherein $R^{2b}$ is H and $R^{2c}$ is Br.

Embodiment 2. The method described in the Summary of the Invention for preparing a compound of Formula 1 comprising contacting a compound of Formula 2 with hydroxylamine in the presence of a base, or the method of any one of Embodiments 1 through 1Q, wherein $Q^b$ is 1-naphthalenyl optionally substituted with one to four substituents independently selected from $R^3$.

Embodiment 2A. The method of Embodiment 2 wherein Q is $Q^a$.

Embodiment 2B. The method of Embodiment 2 wherein Q is $Q^b$.

Embodiment 2C. The method of Embodiment 2 wherein each $R^3$ is independently halogen, $C_1$-$C_6$ alkyl, $C_1$-$C_6$ haloalkyl, —C(=W)N($R^4$)$R^5$, —C(=W)O$R^5$, —CN or —O$R^{11}$; or a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, —CN, —C(=W)N($R^4$)$R^5$ and —C(=O)O$R^5$.

Embodiment 2D. The method of Embodiment 2 wherein each $R^3$ is independently halogen, —C(=W)N($R^4$)$R^5$, —C(=W)O$R^5$, —CN or —O$R^{11}$.

Embodiment 2E. The method of Embodiment 2 wherein each $R^4$ is independently H or $C_1$-$C_6$ alkyl.

Embodiment 2F. The method of Embodiment 2 wherein each $R^5$ is independently H; or $C_1$-$C_6$ alkyl optionally substituted with one or more substituents independently selected from $R^6$.

Embodiment 2G. The method of Embodiment 2 wherein each $R^6$ is independently halogen, $C_1$-$C_6$ alkyl, $C_1$-$C_6$ alkoxy, $C_1$-$C_6$ alkylthio, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylaminocarbonyl, $C_3$-$C_9$ halodialkylaminocarbonyl or —CN; or $Q^2$.

Embodiments 2H. The method of Embodiment 2 wherein each $Q^2$ is a pyridinyl ring optionally substituted with one to four halogen.

Embodiments 2I. The method of Embodiment 2 wherein each $Q^a$ is a phenyl substituted with one $Q^1$ at the para position and optionally substituted with one to three substituents independently selected from $R^3$ at the other positions on the phenyl ring.

Embodiment 2J. The method of Embodiment 2I wherein $Q^1$ is an optionally substituted 1-triazolyl or 1-pyrazolyl ring.

Embodiment 2K. The method of Embodiment 2J wherein $R^3$ is Me or —CN at a meta position of the phenyl ring.

Embodiment 2L. The method of Embodiment 2B wherein Q is

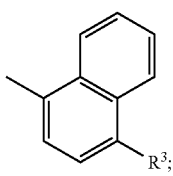

and
$R^3$ is C(O)N($R^4$)$R^5$ or C(O)O$R^5$.

Embodiment 2M. The method of Embodiment 2L wherein $R^4$ is H, $C_2$-$C_7$ alkylcarbonyl or $C_2$-$C_7$ alkoxycarbonyl.

Embodiment 2N. The method of Embodiment 2M wherein $R^4$ is H.

Embodiment 2O. The method of any one of Embodiments 2L through 2N wherein
$R^3$ is C(O)N($R^4$)$R^5$ or C(O)O$R^{5a}$;
$R^5$ is $C_1$-$C_6$ alkyl or $C_1$-$C_6$ haloalkyl, each substituted with one substituent independently selected from hydroxy, $C_1$-$C_6$ alkoxy, $C_1$-$C_6$ alkylthio, $C_1$-$C_6$ alkylsulfinyl, $C_1$-$C_6$ alkylsulfonyl, $C_2$-$C_7$ alkylaminocarbonyl, $C_3$-$C_9$ dialkylaminocarbonyl, $C_2$-$C_7$ haloalkylaminocarbonyl and $C_3$-$C_9$ halodialkylaminocarbonyl; and
$R^{5a}$ is $C_1$-$C_6$ alkyl, $C_2$-$C_6$ alkenyl or $C_2$-$C_6$ alkynyl, each optionally substituted with one or more substituents independently selected from halogen, $C_1$-$C_2$ alkoxy and phenyl optionally substituted with up to 5 substituents selected from halogen and $C_1$-$C_3$ alkyl.

Embodiment 2P. The method of any one of Embodiments 2L through 2O wherein $R^{5a}$ is $C_1$-$C_6$ alkyl optionally substituted with phenyl.

Embodiment 2Q. The method of any one of Embodiments 2L through 2P wherein $R^3$ is C(O)N($R^4$)$R^5$.

Embodiment 2R. The method of any one of Embodiments 2L through 2N wherein $R^3$ is C(O)O$R^5$.

Embodiment 2S. The method of any one of Embodiments 2O through 2P wherein $R^3$ is C(O)O$R^{5a}$.

Embodiment 3. The method described in the Summary of the Invention for preparing a compound of Formula 1 comprising contacting a compound of Formula 2 with hydroxylamine in the presence of a base, or the method of any one of Embodiments 1 through 1Q and 2 through 2S, wherein in Formulae 1 and 2 $R^1$ is $CF_3$.

Embodiment 4. The method described in the Summary of the Invention for preparing a compound of Formula 1 comprising contacting a compound of Formula 2 with hydroxylamine in the presence of a base wherein the contact occurs in a temperature range of from about 0 to about 150° C.

Embodiment 4A. The method of Embodiment 4 wherein the temperature range is from about 15 to about 40° C.

Embodiment 5. The method described in the Summary of the Invention for preparing a compound of Formula 1 comprising contacting a compound of Formula 2 with hydroxylamine in the presence of a base wherein the hydroxylamine is derived from a hydroxylamine salt.

Embodiment 5A. The method of Embodiment 5 wherein the hydroxylamine salt is a hydroxylamine salt of a mineral acid.

Embodiment 5B. The method of Embodiment 5A wherein the hydroxylamine salt is a hydroxylamine salt of hydrochloric acid, sulfuric acid, phosphoric acid, or a mixture thereof.

Embodiment 6. The method described in the Summary of the Invention for preparing a compound of Formula 1 comprising contacting a compound of Formula 2 with hydroxylamine in the presence of a base wherein the molar ratio of hydroxylamine to the compound of Formula 2 is at least about 1.

Embodiment 6A. The method of Embodiment 6 wherein the molar ratio of hydroxylamine to the compound of Formula 2 is at least about 1.2.

Embodiment 6B. The method of Embodiment 6A wherein the molar ratio of hydroxylamine to the compound of Formula 2 is at least about 1.5.

Embodiment 6C. The method described in the Summary of the Invention for preparing a compound of Formula 1 comprising contacting a compound of Formula 2 with hydroxylamine in the presence of a base wherein the molar ratio of hydroxylamine to the compound of Formula 2 is no more than about 3.

Embodiment 7. The method described in the Summary of the Invention for preparing a compound of Formula 1 comprising contacting a compound of Formula 2 with hydroxyl amine in the presence of a base wherein the base comprises one or more compounds selected from organic bases, hydroxide bases, alkoxide bases and carbonate bases.

Embodiment 7A. The method described in the Summary of the Invention for preparing a compound of Formula 1 comprising contacting a compound of Formula 2 with hydroxylamine in the presence of a base wherein the base comprises one or more compounds selected from amine bases, alkali metal hydroxide bases, alkali metal alkoxide bases and alkali metal carbonate bases.

Embodiment 7AA. The method of Embodiment 7 wherein the base comprises an alkali metal carbonate.

Embodiment 7B. The method of Embodiment 7AA wherein the base comprises sodium carbonate, potassium carbonate or a mixture thereof.

Embodiment 7C. The method of Embodiment 7B wherein the base comprises sodium carbonate.

Embodiment 7D. The method of Embodiment 7 wherein the base comprises an alkali metal hydroxide.

Embodiment 7E. The method of Embodiment 7D wherein the base comprises sodium hydroxide, potassium hydroxide or a mixture thereof.

Embodiment 8. The method of the Summary of the Invention for preparing a compound of Formula 1 comprising contacting a compound of Formula 2 with hydroxylamine in the presence of a base wherein the base in excess of the amount needed to neutralize hydroxylamine salts is in an equivalent ratio of at least about 1 to the compound of Formula 2.

Embodiment 8A. The method of Embodiment 8 wherein the ratio is no more than about 5.

Embodiment 9. The method of the Summary of the Invention for preparing a compound of Formula 1 comprising contacting a compound of Formula 2 with hydroxylamine in the presence of a base wherein the compound of Formula 2, hydroxylamine and base are contacted in the presence of a suitable solvent.

Embodiment 9A. The method of Embodiment 9 wherein the suitable solvent comprises a solvent selected from alcohols, ethers, amides, nitriles, halogenated hydrocarbons and aromatic hydrocarbons (including mixtures thereof).

Embodiment 9B. The method of Embodiment 9A wherein the suitable solvent comprises isopropanol.

Embodiment 9C. The method of Embodiment 9A wherein the suitable solvent further comprises water.

Embodiment 10. A compound of Formula 2 as described in the Summary of the Invention wherein
$R^1$ is $CHX_2$, $CX_3$, $CX_2CHX_2$ or $CX_2CX_3$;
each X is independently Cl or F;
Z is optionally substituted phenyl;
Q is $Q^a$ or $Q^b$;
$Q^a$ is phenyl substituted with one $Q^1$ and optionally substituted with one to four substituents independently selected from $R^3$;
$Q^1$ is a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —CN, —$NO_2$, —$N(R^4)R^5$, —C(=W)N$(R^4)R^5$, —C(=O)$OR^5$ and $R^7$;

$Q^b$ is optionally substituted 1-naphthalenyl;
each $R^3$ is independently halogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ haloalkynyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_2$-$C_7$ alkylcarbonyl, $C_2$-$C_7$ haloalkylcarbonyl, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —$N(R^4)R^5$, —C(=W)$N(R^4)R^5$, —C(=W)$OR^5$, —CN, —$OR^{11}$ or —$NO_2$;
or a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —CN, —$NO_2$, —$N(R^4)R^5$, —C(=W)$N(R^4)R^5$, —C(=O)$OR^5$ and $R^7$;
each $R^4$ is independently H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;
each $R^5$ is independently H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;
each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkyl aminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ halodialkylaminocarbonyl, —OH, —$NH_2$, —CN or —$NO_2$; or $Q^2$;
each $R^7$ is independently a phenyl ring or a pyridinyl ring, each ring optionally substituted with one or more substituents independently selected from $R^8$;
each $R^8$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkylcarbonyl, $C_2$-$C_4$ alkoxycarbonyl, $C_2$-$C_7$ alkylaminocarbonyl, $C_3$-$C_7$ dialkylaminocarbonyl, —OH, —$NH_2$, —C(=O)OH, —CN or —$NO_2$;
each $Q^2$ is independently a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —$NO_2$, —C(=W)N($R^9$)$R^{10}$ and —C(=O)$OR^{10}$;
  each $R^9$ is independently H, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;
  each $R^{10}$ is independently H; or $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl;
  each $R^{11}$ is independently H; or $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl, $C_2$-$C_7$ alkoxycarbonyl, $C_1$-$C_6$ alkylsulfonyl or $C_1$-$C_6$ haloalkylsulfonyl; and
each W is independently O or S.
Embodiment 10A. A compound of Embodiment 10 wherein
  Z is phenyl optionally substituted with one to five substituents independently selected from $R^2$; and
  each $R^2$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylamino, $C_2$-$C_6$ dialkylamino, —CN or —$NO_2$.
Embodiment 10B. A compound of Embodiment 10A wherein Z is phenyl substituted with one to three substituents independently selected from $R^2$, said substituents attached at the 3-, 4- or 5-positions of the phenyl ring.
Embodiment 10C. A compound of Embodiment 10A or 10B wherein each $R^2$ is independently halogen, $C_1$-$C_6$ alkyl, $C_1$-$C_6$ haloalkyl or CN.
Embodiment 10D. A compound of Embodiment 10C wherein each $R^2$ is independently halogen or $C_1$-$C_6$ haloalkyl.
Embodiment 10E. A compound of Embodiment 10D wherein each $R^2$ is independently halogen or $CF_3$.
Embodiment 10F. A compound of Embodiment 10E wherein each $R^2$ is independently F, Cl or $CF_3$.
Embodiment 11. A compound of Embodiment 10 wherein $Q^b$ is 1-naphthalenyl optionally substituted with one to four substituents independently selected from $R^3$.
Embodiment 11A. A compound of Embodiment 11 wherein Q is $Q^a$.
Embodiment 11B. A compound of Embodiment 11 wherein Q is $Q^b$.
Embodiment 11C. A compound of Embodiment 11 wherein each $R^3$ is independently halogen, $C_1$-$C_6$ alkyl, $C_1$-$C_6$ haloalkyl, —C(=W)N($R^4$)$R^5$, —C(=W)$OR^5$, —CN or —$OR^{11}$; or a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, —CN, —C(=W)N($R^4$)$R^5$ and —C(=O)$OR^5$.
Embodiment 11D. A compound of Embodiment 11 wherein each $R^3$ is independently halogen, —C(=W)N($R^4$)$R^5$, —C(=W)$OR^5$, —CN or —$OR^{11}$.
Embodiment 11E. A compound of Embodiment 11 wherein each $R^4$ is independently H or $C_1$-$C_6$ alkyl.
Embodiment 11F. A compound of Embodiment 11 wherein each $R^5$ is independently H; or $C_1$-$C_6$ alkyl optionally substituted with one or more substituents independently selected from $R^6$.
Embodiment 11G. A compound of Embodiment 11 wherein each $R^6$ is independently halogen, $C_1$-$C_6$ alkyl, $C_1$-$C_6$ alkoxy, $C_1$-$C_6$ alkylthio, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylaminocarbonyl, $C_3$-$C_9$ halodialkylaminocarbonyl or —CN; or $Q^2$.
Embodiment 11H. A compound of Embodiment 11 wherein each $Q^2$ is a pyridinyl ring optionally substituted with one to four halogen.
Embodiment 11I. A compound of Embodiment 11 wherein each $Q^a$ is a phenyl substituted with one $Q^1$ at the para position and optionally substituted with one to three substituents independently selected from $R^3$ at the other positions on the phenyl ring.
Embodiment 11J. A compound of Embodiment 11I wherein $Q^1$ is an optionally substituted 1-triazolyl or 1-pyrazolyl ring.
Embodiment 11K. A compound of Embodiment 11J wherein $R^3$ is Me or CN at a meta position of the phenyl ring.
Embodiment 12. A compound of Embodiment 10 wherein $R^1$ is $CF_3$.
Embodiment 13. The method described in the Summary of the Invention for preparing a compound of Formula 1 comprising contacting a compound of Formula 2 with hydroxylamine in the presence of a base wherein Z is phenyl optionally substituted with one to five substituents independently selected from $R^2$.
Embodiment 13a. The method of Embodiment 13 wherein Z is phenyl substituted with one to three substituents independently selected from $R^2$, said substituents attached at the 3-, 4- or 5-positions (i.e. meta or para) of the phenyl ring.
Embodiment 13b. The method of Embodiment 13a wherein each $R^2$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylamino, $C_2$-$C_6$ dialkylamino, —CN or —$NO_2$.
Embodiment 13c. The method of Embodiment 13b wherein each $R^2$ is independently halogen, $C_1$-$C_3$ alkyl, $C_1$-$C_3$ haloalkyl, $C_1$-$C_3$ haloalkoxy or —CN.
Embodiment 14. The method described in the Summary of the Invention for preparing a compound of Formula 1 comprising contacting a compound of Formula 2 with hydroxylamine in the presence of a base wherein $R^1$ is $CF_3$.
Embodiment 15. The method described in the Summary of the Invention for preparing a compound of Formula 1 comprising contacting a compound of Formula 2 with hydroxylamine in the presence of a base wherein Q is $Q^a$.
Embodiment 15a. The method of Embodiment 15 wherein $Q^a$ is phenyl substituted with one $Q^1$ attached at the 4-position of the phenyl ring, said phenyl ring further optionally substituted with one or two substituents independently selected from $R^3$
(i.e.

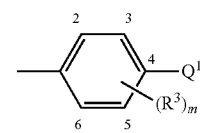

wherein m is 0, 1 or 2).
Embodiment 15b. The method of Embodiment 15a wherein $Q^1$ is a 5-membered heteroaromatic ring optionally substituted with one or two substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, —CN, —C(=W)N($R^4$)$R^5$ and —C(=O)O$R^5$.

Embodiment 15c. The method of Embodiment 15b wherein $Q^1$ is a pyrazole or triazole ring optionally substituted with one or two substituents independently selected from halogen, —CN and —C(=W)N($R^4$)$R^5$.

Embodiment 15d. The method of Embodiment 15a wherein each $R^3$ is independently halogen, $C_1$-$C_6$ alkyl or —CN.

Embodiment 15e. The method of Embodiment 15d wherein one $R^3$ is Cl, $CH_3$ or —CN and is attached at the 3-position of the phenyl ring (i.e. adjacent to $Q^1$).

Embodiment 15f. The method of Embodiment 15b or 15c wherein $R^4$ is H.

Embodiment 15g. The method of Embodiment 15b or 15c wherein $R^5$ is H; or $C_1$-$C_3$ alkyl, cyclopropyl or cyclopropylmethyl, each optionally substituted with halogen and further optionally substituted with 1 or 2 $CH_3$.

Embodiment 16. The method described in the Summary of the Invention for preparing a compound of Formula 1 comprising contacting a compound of Formula 2 with hydroxylamine in the presence of a base wherein Q is $Q^b$.

Embodiment 16a. The method of Embodiment 16 wherein $Q^b$ is 1-naphthalenyl substituted with one or two substituents independently selected from $R^3$ (i.e.

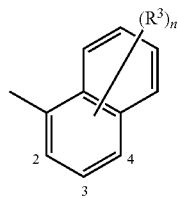

wherein n is 1 or 2).

Embodiment 16b. The method of Embodiment 16 wherein $Q^b$ is 1-naphthalenyl substituted with one $R^3$ attached at the 4-position of the naphthalene ring (i.e.

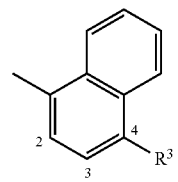

).

Embodiment 16c. The method of Embodiment 16a or 16b wherein one $R^3$ is halogen, $C_1$-$C_6$ alkyl, $C_1$-$C_6$ haloalkyl, $C_1$-$C_6$ alkoxy, —N($R^4$)$R^5$, —C(=W)N($R^4$)$R^5$, —C(=W)O$R^5$, —CN, —O$R^{11}$ or —NO$_2$, and said $R^3$ is attached at the 4-position of the naphthalene ring.

Embodiment 16d. The method of Embodiment 16c wherein the $R^3$ attached at the 4-position of the naphthalene ring is —C(=O)N($R^4$)$R^5$.

Embodiment 16e. The method of Embodiment 16c or 16d wherein each $R^4$ is independently H, $C_1$-$C_6$ alkyl, $C_2$-$C_7$ alkylcarbonyl or $C_2$-$C_7$ alkoxycarbonyl.

Embodiment 16f. The method of Embodiment 16c or 16d wherein each $R^5$ is independently $C_1$-$C_6$ alkyl substituted with one substituent selected from hydroxy, $C_1$-$C_6$ alkoxy, $C_1$-$C_6$ alkylthio, $C_1$-$C_6$ alkylsulfinyl, $C_1$-$C_6$ alkylsulfonyl, $C_2$-$C_7$ alkylaminocarbonyl, $C_3$-$C_9$ dialkylaminocarbonyl, $C_2$-$C_7$ haloalkylaminocarbonyl, $C_3$-$C_9$ halodialkylaminocarbonyl and $Q^2$.

Embodiment 16g. The method of Embodiment 16c or 16d wherein each $R^5$ is independently $C_1$-$C_2$ alkyl substituted with $C_2$-$C_7$ haloalkylaminocarbonyl.

Embodiment 16h. The method of Embodiment 16f wherein $Q^2$ is a pyridinyl ring optionally substituted with one to four halogen.

Embodiment 16i. The method of Embodiment 16c wherein $R^{11}$ is H, $C_2$-$C_6$ alkenyl, $C_2$-$C_6$ alkynyl, $C_2$-$C_7$ alkylcarbonyl, $C_2$-$C_7$ alkoxycarbonyl, $C_1$-$C_6$ alkylsulfonyl or $C_1$-$C_6$ haloalkylsulfonyl.

Embodiment 17. A compound of Formula 2 as described in the Summary of the Invention wherein $R^1$ is $CHX_2$, $CX_3$, $CX_2CHX_2$ or $CX_2CX_3$;

each X is independently Cl or F;

Z is optionally substituted phenyl;

Q is $Q^a$ or $Q^b$;

$Q^a$ is phenyl substituted with one $Q^1$ and optionally substituted with one to four substituents independently selected from $R^3$;

$Q^1$ is a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —CN, —NO$_2$, —N($R^4$)$R^5$, —C(=W)N($R^4$)$R^5$, —C(=O)O$R^5$ and $R^7$;

$Q^b$ is optionally substituted 1-naphthalenyl;

each $R^3$ is independently halogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ haloalkynyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_2$-$C_7$ alkylcarbonyl, $C_2$-$C_7$ haloalkylcarbonyl, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —N($R^4$)$R^5$, —C(=W)N($R^4$)$R^5$, —C(=W)O$R^5$, —CN, —O$R^{11}$ or —NO$_2$; or a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, —CN, —NO$_2$, —N($R^4$)$R^5$, —C(=W)N($R^4$)$R^5$, —C(=O)O$R^5$ and $R^7$;

each $R^4$ is independently H, $C_1$-$C_6$ alkyl, $C_2$-$C_6$ alkenyl, $C_2$-$C_6$ alkynyl, $C_3$-$C_6$ cycloalkyl, alkylcycloalkyl, cycloalkylalkyl, $C_2$-$C_7$ alkylcarbonyl or $C_2$-$C_7$ alkoxycarbonyl;

each $R^5$ is independently H; or $C_1$-$C_6$ alkyl, $C_2$-$C_6$ alkenyl, $C_2$-$C_6$ alkynyl, $C_3$-$C_6$ cycloalkyl, alkylcycloalkyl or $C_4$-$C_7$ cycloalkylalkyl, each optionally substituted with one or more substituents independently selected from $R^6$.

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ halodialkylaminocarbonyl, —OH, —$NH_2$, —CN or —$NO_2$; or $Q^2$;

each $R^7$ is independently a phenyl ring or a pyridinyl ring, each ring optionally substituted with one or more substituents independently selected from $R^8$;

each $R^8$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkylcarbonyl, $C_2$-$C_4$ alkoxycarbonyl, $C_2$-$C_7$ alkylaminocarbonyl, $C_3$-$C_7$ dialkylaminocarbonyl, —OH, —$NH_2$, —C(=O)OH, —CN or —$NO_2$;

each $Q^2$ is independently a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —$NO_2$, —C(=W)N($R^9$)$R^{10}$ and —C(=O)O$R^{10}$;

each $R^9$ is independently H, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

each $R^{10}$ is independently H; or $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl;

each $R^{11}$ is independently H; or $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl, $C_2$-$C_7$ alkoxycarbonyl, $C_1$-$C_6$ alkylsulfonyl or $C_1$-$C_6$ haloalkylsulfonyl; and each W is independently O or S.

Embodiment 17a. A compound of Embodiment 17 wherein Z is phenyl optionally substituted with one to five substituents independently selected from $R^2$.

Embodiment 17b. A compound of Embodiment 17a wherein Z is phenyl substituted with one to three substituents independently selected from $R^2$, said substituents attached at the 3-, 4- or 5-positions (i.e. meta or para) of the phenyl ring.

Embodiment 17c. A compound of Embodiment 17b wherein each $R^2$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylamino, $C_2$-$C_6$ dialkylamino, —CN or —$NO_2$.

Embodiment 17d. A compound of Embodiment 17c wherein each $R^2$ is independently halogen, $C_1$-$C_3$ alkyl, $C_1$-$C_3$ haloalkyl, $C_1$-$C_3$ haloalkoxy or —CN.

Embodiment 18. A compound of Formula 2 wherein $R^1$ is $CF_3$.

Embodiment 19. A compound of Formula 2 wherein Q is $Q^a$.

Embodiment 19a. A compound of Embodiment 19 wherein $Q^a$ is phenyl substituted with one $Q^1$ attached at the 4-position of the phenyl ring, said phenyl ring further optionally substituted with one or two substituents independently selected from $R^3$
(i.e.

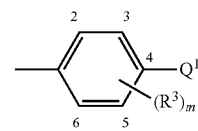

wherein m is 0, 1 or 2).

Embodiment 19b. A compound of Embodiment 19a wherein $Q^1$ is a 5-membered heteroaromatic ring optionally substituted with one or two substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, —CN, —C(=W)N($R^4$)$R^5$ and —C(=O)O$R^5$.

Embodiment 19c. A compound of Embodiment 19b wherein $Q^1$ is a pyrazole or triazole ring optionally substituted with one or two substituents independently selected from halogen, —CN and —C(=W)N($R^4$)$R^5$.

Embodiment 19d. A compound of Embodiment 19a wherein each $R^3$ is independently halogen, $C_1$-$C_6$ alkyl or —CN.

Embodiment 19e. A compound of Embodiment 19d wherein one $R^3$ is Cl, $CH_3$ or —CN and is attached at the 3-position of the phenyl ring (i.e. adjacent to $Q^1$).

Embodiment 19f. A compound of Embodiment 19b or 19c wherein $R^4$ is H.

Embodiment 19g. A compound of Embodiment 19b or 19c wherein $R^5$ is H; or $C_1$-$C_3$ alkyl, cyclopropyl or cyclopropylmethyl, each optionally substituted with halogen and further optionally substituted with 1 or 2 $CH_3$.

Embodiment 20. A compound of Formula 2 wherein Q is $Q^b$.

Embodiment 20a. A compound of Embodiment 20 wherein $Q^b$ is 1-naphthalenyl substituted with one or two substituents independently selected from $R^3$
(i.e.

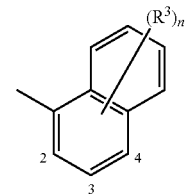

wherein n is 1 or 2).

Embodiment 20b. A compound of Embodiment 20 wherein $Q^b$ is 1-naphthalenyl substituted with one $R^3$ attached at the 4-position of the naphthalene ring (i.e.

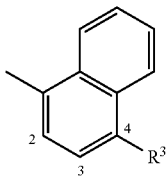

).

Embodiment 20c. A compound of Embodiment 20a or 20b wherein one $R^3$ is halogen, $C_1$-$C_6$ alkyl, $C_1$-$C_6$ haloalkyl, $C_1$-$C_6$ alkoxy, —N($R^4$)$R^5$, —C(=W)N($R^4$)$R^5$, —C(=W)O$R^5$, —CN, —O$R^{11}$ or —NO$_2$, and said $R^3$ is attached at the 4-position of the naphthalene ring.

Embodiment 20d. A compound of Embodiment 20c wherein the $R^3$ attached at the 4-position of the naphthalene ring is —C(=O)N($R^4$)$R^5$.

Embodiment 20e. A compound of Embodiment 20c or 16d wherein each $R^4$ is independently H, $C_1$-$C_6$ alkyl, $C_2$-$C_7$ alkylcarbonyl or $C_2$-$C_7$ alkoxycarbonyl.

Embodiment 20f. A compound of Embodiment 20c or 20d wherein each $R^5$ is independently $C_1$-$C_6$ alkyl substituted with one substituent selected from hydroxy, $C_1$-$C_6$ alkoxy, $C_1$-$C_6$ alkylthio, $C_1$-$C_6$ alkylsulfinyl, $C_1$-$C_6$ alkylsulfonyl, $C_2$-$C_7$ alkylaminocarbonyl, $C_3$-$C_9$ dialkylaminocarbonyl, $C_2$-$C_7$ haloalkylaminocarbonyl, $C_3$-$C_9$ halodialkylaminocarbonyl and $Q^2$.

Embodiment 20g. A compound of Embodiment 20c or 20d wherein each $R^5$ is independently $C_1$-$C_2$ alkyl substituted with $C_2$-$C_7$ haloalkylaminocarbonyl.

Embodiment 20h. A compound of Embodiment 20f wherein $Q^2$ is a pyridinyl ring optionally substituted with one to four halogen.

Embodiment 20i. A compound of Embodiment 20c wherein $R^{11}$ is H, $C_2$-$C_6$ alkenyl, $C_2$-$C_6$ alkynyl, $C_2$-$C_7$ alkylcarbonyl, $C_2$-$C_7$ alkoxycarbonyl, $C_1$-$C_6$ alkylsulfonyl or $C_1$-$C_6$ haloalkylsulfonyl.

Embodiments of this invention, including Embodiments 1-20i above as well as any other embodiments described herein, can be combined in any manner, and the descriptions of variables in the embodiments pertain not only to the compounds of Formula 1 and Formula 2 but also to the starting compounds and intermediate compounds useful for preparing the compounds of Formula 1 or Formula 2.

Combinations of Embodiments 1-20i are illustrated by:

Embodiment A. The method described in the Summary of the Invention for preparing a compound of Formula 1 comprising contacting a compound of Formula 2 with hydroxylamine in the presence of a base wherein
Z is phenyl optionally substituted with one to five substituents independently selected from $R^2$;
each $R^2$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylamino, $C_2$-$C_6$ dialkylamino, —CN or —NO$_2$; and
$Q^b$ is 1-naphthalenyl optionally substituted with one to four substituents independently selected from $R^3$.

Embodiment B. The method of Embodiment A wherein Q is $Q^a$.

Embodiment C. The method of Embodiment A wherein Q is $Q^b$.

Embodiment D. The method of Embodiment B or C wherein in Formulae 1 and 2 $R^1$ is CF$_3$.

Embodiment E. The method of Embodiment D wherein each $R^2$ is independently halogen or $C_1$-$C_6$ haloalkyl;

each $R^3$ is independently halogen, $C_1$-$C_6$ alkyl, $C_1$-$C_6$ haloalkyl, —C(=W)N($R^4$)$R^5$, —C(=W)O$R^5$, —CN or —O$R^{11}$; or a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, —CN, —C(=W)N($R^4$)$R^5$ and —C(=O)O$R^5$;

each $R^4$ is independently H or $C_1$-$C_6$ alkyl;

each $R^5$ is independently H; or $C_1$-$C_6$ alkyl optionally substituted with one or more substituents independently selected from $R^6$;

each $R^6$ is independently halogen, $C_1$-$C_6$ alkyl, $C_1$-$C_6$ alkoxy, $C_1$-$C_6$ alkylthio, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylaminocarbonyl, $C_3$-$C_9$ halodialkylaminocarbonyl or —CN; or $Q^2$; and each $Q^2$ is a pyridinyl ring optionally substituted with one to four halogen.

Embodiment E1. The method of Embodiment C or D wherein
Z is

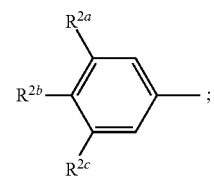

Q is

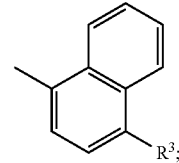

$R^{2a}$ is halogen, $C_1$-$C_2$ haloalkyl or $C_1$-$C_2$ haloalkoxy;
$R^{2b}$ is H, halogen or cyano;
$R^{2c}$ is H, halogen or CF$_3$;
$R^3$ is C(O)N($R^4$)$R^5$ or C(O)O$R^{5a}$;
$R^4$ is H, $C_2$-$C_7$ alkylcarbonyl or $C_2$-$C_7$ alkoxycarbonyl; and
$R^5$ is $C_1$-$C_6$ alkyl or $C_1$-$C_6$ haloalkyl, each substituted with one substituent independently selected from hydroxy, $C_1$-$C_6$ alkoxy, $C_1$-$C_6$ alkylthio, $C_1$-$C_6$ alkylsulfinyl, $C_1$-$C_6$ alkylsulfonyl, $C_2$-$C_7$ alkylaminocarbonyl, $C_3$-$C_9$ dialkylaminocarbonyl, $C_2$-$C_7$ haloalkylaminocarbonyl and $C_3$-$C_9$ halodialkylaminocarbonyl; and
$R^{5a}$ is $C_1$-$C_6$ alkyl, $C_2$-$C_6$ alkenyl or $C_2$-$C_6$ alkynyl, each optionally substituted with one or more substituents independently selected from halogen, $C_1$-$C_2$ alkoxy and phenyl optionally substituted with up to 5 substituents selected from halogen and $C_1$-$C_3$ alkyl.

Embodiment E2. The method of Embodiment E1 wherein $R^3$ is C(O)N($R^4$)$R^5$.

Embodiment E3. The method of Embodiment E1 wherein $R^3$ is C(O)O$R^{5a}$.

Embodiment F. A compound of Formula 2 wherein
  Z is phenyl optionally substituted with one to five substituents independently selected from $R^2$;
  each $R^2$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylamino, $C_2$-$C_6$ dialkylamino, —CN or —$NO_2$; and
  $Q^b$ is 1-naphthalenyl optionally substituted with one to four substituents independently selected from $R^3$.

Embodiment G. A compound of Embodiment F wherein Q is $Q^a$.

Embodiment H. A compound of Embodiment F wherein Q is $Q^b$.

Embodiment I. A compound of Embodiment G or H wherein $R^1$ is $CF_3$.

Embodiment J. A compound of Embodiment I wherein
  each $R^2$ is independently halogen or $C_1$-$C_6$ haloalkyl;
  each $R^3$ is independently halogen, $C_1$-$C_6$ alkyl, $C_1$-$C_6$ haloalkyl, —C(=W)N($R^4$)$R^5$, —C(=W)O$R^5$, —CN or —O$R^{11}$; or a phenyl ring or a 5- or 6-membered saturated or unsaturated heterocyclic ring, each ring optionally substituted with one or more substituents independently selected from halogen, $C_1$-$C_6$ alkyl, $C_1$-$C_6$ haloalkyl, —CN, —C(=W)N($R^4$)$R^5$ and —C(=O)O$R^5$;
  each $R^4$ is independently H or $C_1$-$C_6$ alkyl;
  each $R^5$ is independently H; or $C_1$-$C_6$ alkyl optionally substituted with one or more substituents independently selected from $R^6$;
  each $R^6$ is independently halogen, $C_1$-$C_6$ alkyl, $C_1$-$C_6$ alkoxy, $C_1$-$C_6$ alkylthio, $C_2$-$C_7$ alkoxycarbonyl, $C_2$-$C_7$ alkylaminocarbonyl, $C_3$-$C_9$ dialkylaminocarbonyl, $C_1$-$C_7$ haloalkylaminocarbonyl, $C_3$-$C_9$ halodialkylaminocarbonyl or —CN; or $Q^2$; and
  each $Q^2$ is a pyridinyl ring optionally substituted with one to four halogen.

Embodiment K. A compound of Embodiment J wherein
  each $R^3$ is independently halogen, —C(=W)N($R^4$)$R^5$, —C(=W)O$R^5$, —CN or —O$R^{11}$.

Embodiment AA. The method described in the Summary of the Invention for preparing a compound of Formula 1 comprising contacting a compound of Formula 2 with hydroxylamine in the presence of a base wherein
  Z is phenyl optionally substituted with one to five substituents independently selected from $R^2$; and
  each $R^2$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylamino, $C_2$-$C_6$ dialkylamino, —CN or —$NO_2$.

Embodiment BB. The method of Embodiment AA wherein
  $R^1$ is $CF_3$;
  Z is phenyl substituted with one to three substituents independently selected from $R^2$, said substituents attached at the 3-, 4- or 5-positions (i.e. meta or para) of the phenyl ring; and
  each $R^2$ is independently halogen, $C_1$-$C_3$ alkyl, $C_1$-$C_3$ haloalkyl, $C_1$-$C_3$ haloalkoxy or —CN.

Embodiment CC. The method of Embodiment BB wherein Q is $Q^a$.

Embodiment DD. The method of Embodiment CC wherein
  $Q^a$ is phenyl substituted with one $Q^1$ attached at the 4-position of the phenyl ring, said phenyl ring further optionally substituted with one or two substituents independently selected from $R^3$;
  $Q^1$ is a 5-membered heteroaromatic ring optionally substituted with one or two substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, —CN, —C(=W)N($R^4$)$R^5$ and —C(=O)O$R^5$; and
  each $R^3$ is independently halogen, $C_1$-$C_6$ alkyl or —CN.

Embodiment EE. The method of Embodiment DD wherein
  $Q^1$ is a pyrazole or triazole ring optionally substituted with one or two substituents independently selected from halogen, —CN and —C(=W)N($R^4$)$R^5$;
  one $R^3$ is Cl, $CH_3$ or —CN and is attached at the 3-position of the phenyl ring adjacent to $Q^1$;
  $R^4$ is H; and
  $R^5$ is H; or $C_1$-$C_3$ alkyl, cyclopropyl or cyclopropylmethyl, each optionally substituted with halogen and further optionally substituted with 1 or 2 $CH_3$.

Embodiment FF. The method of Embodiment BB wherein Q is $Q^b$.

Embodiment GG. The method of Embodiment FF wherein $Q^b$ is 1-naphthalenyl substituted with one or two substituents independently selected from $R^3$.

Embodiment HH. The method of Embodiment GG wherein
  one $R^3$ is halogen, $C_1$-$C_6$ alkyl, $C_1$-$C_6$ haloalkyl, $C_1$-$C_6$ alkoxy, —N($R^4$)$R^5$, —C(=W)N($R^4$)$R^5$, —C(=W)O$R^5$, —CN, —O$R^{11}$ or —$NO_2$, and said $R^3$ is attached at the 4-position of the naphthalene ring;
  each $R^4$ is independently H, $C_1$-$C_6$ alkyl, $C_2$-$C_7$ alkylcarbonyl or $C_2$-$C_7$ alkoxycarbonyl;
  $R^5$ is $C_1$-$C_6$ alkyl substituted with one substituent selected from hydroxy, $C_1$-$C_6$ alkoxy, $C_1$-$C_6$ alkylthio, $C_1$-$C_6$ alkylsulfinyl, $C_1$-$C_6$ alkylsulfonyl, $C_2$-$C_7$ alkylaminocarbonyl, $C_3$-$C_9$ dialkylaminocarbonyl, $C_2$-$C_7$ haloalkylaminocarbonyl, $C_3$-$C_9$ halodialkylaminocarbonyl and $Q^2$;
  $Q^2$ is a pyridinyl ring optionally substituted with one to four halogen; and
  $R^{11}$ is H, $C_2$-$C_6$ alkenyl, $C_2$-$C_6$ alkynyl, $C_2$-$C_7$ alkylcarbonyl, $C_2$-$C_7$ alkoxycarbonyl, $C_1$-$C_6$ alkylsulfonyl or $C_1$-$C_6$ haloalkylsulfonyl.

Embodiment II. The method of Embodiment HH wherein
  $Q^b$ is 1-naphthalenyl substituted with one $R^3$ attached at the 4-position of the naphthalene ring;
  $R^3$ is —C(=O)N($R^4$)$R^5$;
  $R^4$ is H; and
  $R^5$ is $C_1$-$C_2$ alkyl substituted with $C_2$-$C_7$ haloalkylaminocarbonyl.

Embodiment JJ. A compound of Formula 2 wherein
  Z is phenyl optionally substituted with one to five substituents independently selected from $R^2$;
  each $R^2$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylamino, $C_2$-$C_6$ dialkylamino, —CN or —$NO_2$; and
  $R^1$ and Q are as defined in the Summary of the Invention.

Embodiment KK. A compound of Embodiment JJ wherein
  $R^1$ is $CF_3$;
  Z is phenyl substituted with one to three substituents independently selected from $R^2$, said substituents attached at the 3-, 4- or 5-positions (i.e. meta or para) of the phenyl ring; and
  each $R^2$ is independently halogen, $C_1$-$C_3$ alkyl, $C_1$-$C_3$ haloalkyl, $C_1$-$C_3$ haloalkoxy or —CN.

Embodiment LL. A compound of Embodiment KK wherein
  Q is $Q^a$.

Embodiment MM. A compound of Embodiment LL wherein $Q^a$ is phenyl substituted with one $Q^1$ attached at the 4-position of the phenyl ring, said phenyl ring further optionally substituted with one or two substituents independently selected from $R^3$;

$Q^1$ is a 5-membered heteroaromatic ring optionally substituted with one or two substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, —CN, —C(=W)N($R^4$)$R^5$ and —C(=O)O$R^5$; and each $R^3$ is independently halogen, $C_1$-$C_6$ alkyl or —CN.

Embodiment NN. A compound of Embodiment MM wherein $Q^1$ is a pyrazole or triazole ring optionally substituted with one or two substituents independently selected from halogen, —CN and —C(=W)N($R^4$)$R^5$;

one $R^3$ is Cl, $CH_3$ or —CN and is attached at the 3-position of the phenyl ring adjacent to $Q^1$;

$R^4$ is H; and $R^5$ is H; or $C_1$-$C_3$ alkyl, cyclopropyl or cyclopropylmethyl, each optionally substituted with halogen and further optionally substituted with 1 or 2 $CH_3$.

Embodiment OO. A compound of Embodiment KK wherein

Q is $Q^b$.

Embodiment PP. A compound of Embodiment OO wherein $Q^b$ is 1-naphthalenyl substituted with one or two substituents independently selected from $R^3$.

Embodiment QQ. A compound of Embodiment PP wherein one $R^3$ is halogen, $C_1$-$C_6$ alkyl, $C_1$-$C_6$ haloalkyl, $C_1$-$C_6$ alkoxy, —N($R^4$)$R^5$, —C(=W)N($R^4$)$R^5$, —C(=W)O$R^5$, —CN, —O$R^{11}$ or —NO$_2$, and said $R^3$ is attached at the 4-position of the naphthalene ring;

each $R^4$ is independently H, $C_1$-$C_6$ alkyl, $C_2$-$C_7$ alkylcarbonyl or $C_2$-$C_7$ alkoxycarbonyl;

$R^5$ is $C_1$-$C_6$ alkyl substituted with one substituent selected from hydroxy, $C_1$-$C_6$ alkoxy, $C_1$-$C_6$ alkylthio, $C_1$-$C_6$ alkylsulfinyl, $C_1$-$C_6$ alkylsulfonyl, $C_2$-$C_7$ alkylaminocarbonyl, $C_3$-$C_9$ dialkylaminocarbonyl, $C_2$-$C_7$ haloalkylaminocarbonyl, $C_3$-$C_9$ halodialkylaminocarbonyl and $Q^2$;

$Q^2$ is a pyridinyl ring optionally substituted with one to four halogen; and $R^{11}$ is H, $C_2$-$C_6$ alkenyl, $C_2$-$C_6$ alkynyl, $C_2$-$C_7$ alkylcarbonyl, $C_2$-$C_7$ alkoxycarbonyl, $C_1$-$C_6$ alkylsulfonyl or $C_1$-$C_6$ haloalkylsulfonyl.

Embodiment RR. A compound of Embodiment QQ wherein $Q^b$ is 1-naphthalenyl substituted with one $R^3$ attached at the 4-position of the naphthalene ring;

$R^3$ is —C(=O)N($R^4$)$R^5$;

$R^4$ is H; and $R^5$ is $C_1$-$C_2$ alkyl substituted with $C_2$-$C_7$ haloalkylaminocarbonyl.

In the following Schemes 1-8 the definitions of $R^1$, $R^2$, $R^4$, $R^5$, Z, and Q in the compounds of Formulae 1 through 9 are as defined above in the Summary of the Invention and description of Embodiments unless otherwise indicated. Formulae 1a, 1b, 1c and 1d are subsets of Formula 1.

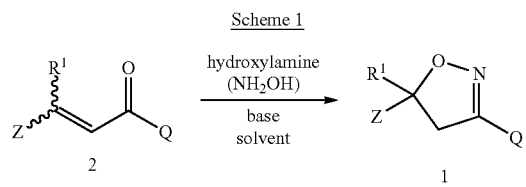

Scheme 1

As shown in Scheme 1, according to the method of this invention a compound of Formula 2 is contacted with hydroxylamine and a base to form a 5-haloalkyl-4,5-dihydroisoxazole compound of Formula 1.

Hydroxylamine can be generated from a mineral acid salt such as hydroxylamine sulfate or hydroxylamine chloride by treatment with a base in a suitable solvent, or can be obtained commercially as 50% aqueous solution. In this method before contact with an enone of Formula 2, hydroxylamine or a mineral acid salt thereof is typically contacted with a base. When a mineral acid salt of hydroxylamine is used, the base is contacted in an amount in excess of the amount needed to convert the hydroxylamine mineral acid salt to hydroxylamine. Base is not consumed in the reaction of Scheme 1, and appears to act as a catalyst for the desired cyclization. Deprotonation of the hydroxylamine with a base prior to contact with an enone of Formula 2 is necessary to obtain good yields, because in the absence of base the reaction of hydroxylamine with enones can afford products other than compounds of Formula 2. Therefore although often about one molar equivalent of base (in addition to any base used to convert a hydroxylamine mineral acid salt to hydroxylamine) is used relative to hydroxylamine, less than one molar equivalent of base can give excellent results. More than one molar equivalent (e.g., up to about 5 molar equivalents) of base relative to hydroxylamine can be used, provided that the excess base does not react with the enone of Formula 2 or the isoxazole of Formula 1.

A molar excess of one to three equivalents of hydroxylamine relative to the enone of Formula 2 can be used. To ensure the cost-effective, complete, and expeditious conversion of the enone of Formula 2 to the isoxazole of Formula 1, in a manner suitable for large-scale production, between about one and about two molar equivalents of hydroxyl amine relative to the enone of Formula 2 is typically found to be most suitable.

Suitable bases can include, but are not limited to, alkali metal alkoxides such as sodium methoxide, alkali metal carbonates such as sodium carbonate or potassium carbonate, alkali metal hydroxides such as sodium hydroxide or potassium hydroxide, and organic bases. Preferred organic bases are amine bases having at least one pair of free electrons available for protonation such as pyridine, triethylamine or N,N-diisopropylethylamine. Weaker bases such as pyridine can be used, but stronger bases which efficiently deprotonate hydroxylamine, such as an alkali metal alkoxide or an alkali metal hydroxide, typically provide better results. Because water is an especially useful solvent for deprotonating hydroxylamine, as well as forming hydroxylamine from its salts, bases compatible with water are of particular note. Examples of strong bases that are soluble and compatible with water are alkali metal hydroxides. Sodium hydroxide is preferred, because it is inexpensive and works well for deprotonating hydroxylamine, thereby forming the sodium salt of hydroxylamine in aqueous solution. Alkali metal alkoxides are frequently used in solution in a lower alkanol, often the alkanol corresponding to the alkoxide.

The method of Scheme 1 is conducted in the presence of a suitable solvent. For best results the solvent should be inert to the base and hydroxylamine, and should be capable of dissolving the enone of Formula 2. Suitable organic solvents include alcohols, ethers, nitriles or aromatic hydrocarbons. Water-miscible solvents such as alcohols (e.g., methanol, isopropanol), ethers (e.g., tetrahydrofuran) or nitriles (e.g., acetonitrile) work well with alkali metal hydroxide bases. Solvents which are non-nucleophilic (e.g., ethers and nitriles) often provide the best results. Particularly when a single solvent is used, the most preferred solvents are tetrahydrofuran and acetonitrile.

Alternatively it may be more desirable to conduct the reaction using a mixture of two solvents formed by contacting a solution of the enone of Formula 2 in a solvent such as tetrahydrofuran or acetonitrile with a solution of hydroxylamine and a base such as sodium hydroxide in a second solvent, which acts as the co-solvent in the solvent mixture. Water is particularly useful as a co-solvent, because mineral acid salts of hydroxylamine and alkali metal hydroxide bases such as sodium hydroxide are particularly soluble in water. The rapid generation of hydroxylamine from its mineral acid salt and subsequent deprotonation of hydroxylamine facilitated by water, and the solubility and stability of the deprotonated species in water are especially desirable. In large-scale production, solutions rather than slurries are preferred, because they are easier to handle and transfer in process equipment. When water is the co-solvent, the other solvent is typically a water-miscible solvent such as tetrahydrofuran or acetonitrile.

Other highly polar, hydroxylic solvents such as lower alkanols (e.g., methanol, ethanol) are also particularly useful as co-solvents, because like water they readily dissolve mineral acid salts of hydroxylamine and alkali metal hydroxides. Lower alkanols can give better results than water as a co-solvent when the other solvent is not water-miscible, e.g., tert-butyl methyl ether. When a lower alkanol is used as a co-solvent, particularly with another solvent that is not water-miscible, the base added is often an alkali metal alkoxide instead of an alkali metal hydroxide.

As long as base is present to deprotonate hydroxylamine, the hydroxylamine, the base and the enone of Formula 2 can be contacted in a variety of ways in the method of Scheme 1. For example, a mixture formed from hydroxylamine and the base (typically in a solvent such as water) can be added to the enone of Formula 2 (typically in a solvent such as tetrahydrofuran or acetonitrile). Alternatively, the hydroxylamine and the base can be concurrently added separately to the enone of Formula 2. In another embodiment, the enone of Formula 2 (typically in a solvent such as tetrahydrofuran or acetonitrile) can be added to a mixture formed from the hydroxylamine and the base (typically in a solvent such as water). In these example embodiments other combinations of solvents can be used; for example, methanol with tert-butyl methyl ether instead of water with tetrahydrofuran or acetonitrile.

The method of Scheme 1 can be conducted at a reaction temperature between about 0 and 150° C., or most conveniently between 20 and 40° C. The product of Formula 1 is isolated by the usual methods known to those skilled in the art including extraction and crystallization.

Scheme 2

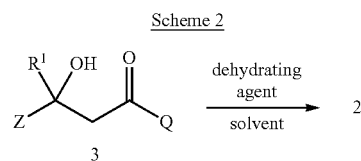

Compounds of Formula 2 can be prepared by dehydration of compounds of Formula 3 as shown in Scheme 2 according to the general method of Sosnovskikh et al., *J. Org. Chem. USSR*/(Eng. Trans.), 1992, 28, 420.

This method involves portion-wise addition of a dehydrating agent such as thionyl chloride to a mixture of a compound of Formula 3 and a base in an organic solvent such as toluene to provide a compound of Formula 2. About two molar equivalents of thionyl chloride relative to the compound of Formula 3 are typically required for high levels of conversion to the compound of Formula 2.

Bases useful in the method of Scheme 2 include amine bases such as pyridine. About three molar equivalents of pyridine relative to the compound of Formula 3 is typically necessary to achieve the conversion of the compound of Formula 3 to the compound of Formula 2.

The method of Scheme 2 is generally conducted using a reaction temperature in the range of about 50 to about 80° C., more commonly in the range of about 60 to about 65° C. After the reaction mixture is treated with water to remove salts, the product can be isolated by the usual methods known to one skilled in the art such as extraction and crystallization.

As shown in Scheme 3, compounds of Formula 2 can also be prepared from addition-elimination reactions of organometallic reagents such as Grignard reagents of Formula 4 with β-enamines or β-haloenones of Formula 5.

Scheme 3

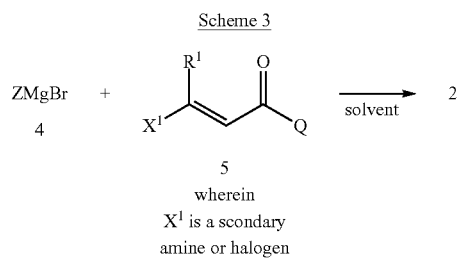

wherein
$X^1$ is a secondary
amine or halogen

The reaction can be run in a variety of solvents including tetrahydrofuran, diethyl ether, dioxane or methylene chloride, and optimum temperatures range from about −78° C. to the refluxing temperature of the solvent. General procedures for additions of Grignard reagents to enamines and haloenones are well documented in the chemical literature; see for example, Jeong et al., *Journal of Fluorine Chemistry* 2004, 125, 1629-1638, as well as references cited within. The method of Scheme 3 is illustrated in Reference Example 1, Step B.

Alternatively, as shown in Scheme 4, a compound of Formula 2 can be formed by condensation of a ketone of Formula 6 with a phosphonate compound of Formula 7 according to the Wadsworth-Emmons modification of the Wittig Reaction.

Scheme 4

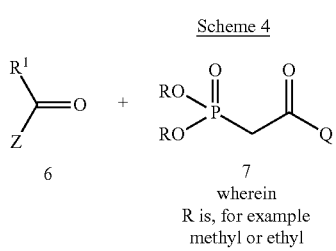

wherein
R is, for example
methyl or ethyl

In this method, the phosphonate compound of Formula 7 is deprotonated with a base such as pyridine, triethylamine, NaH, NaHCO$_3$ or lithium diisopropylamide (LDA) in a solvent such as tetrahydrofuran, diethyl ether, dioxane or methylene chloride to form a ylid intermediate, and the ketone of Formula 6 is added to provide the compound of Formula 2. Optimum temperatures range from about 0° C. to the refluxing temperature of the solvent. The general reaction conditions of the Wittig Reaction are well documented in the chemical literature. For example, see Dull et al., *J. Org. Chem.* 1967, 32, 1622-1623.

A wide variety of methods exist for the preparation of β-hydroxyketone compounds of Formula 3. For example, ketones can be combined under acidic, or more commonly basic conditions, to provide compounds of Formula 3. The aldol condensation has been extensively reviewed (e.g., *Organic Reactions,* 1968, 16, 1), and wide range of conditions have been used to achieve this transformation. This reaction is illustrated in Scheme 5.

Scheme 5

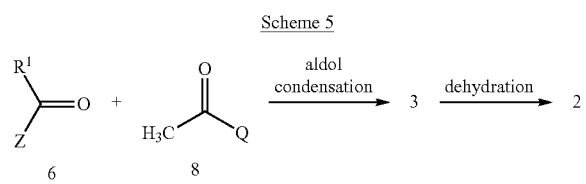

Some of the conditions usually employed in the aldol condensation may be precluded by the reactivity of compounds of Formula 6 (e.g., wherein R$^1$ is CF$_3$) and compounds of Formula 3 (e.g., wherein R$^1$ is CF$_3$) with nucleophiles. A compound of Formula 3 wherein R$^1$ is CF$_3$ can be prepared by addition of a non-nucleophilic base such as lithium hydride (Sosnovskikh et al., *J. Org. Chem. USSR (Eng. Trans.),* 1992, 28, 420), or potassium carbonate to a mixture of a ketone of Formula 6 and a ketone of Formula 8 in a suitable non-nucleophilic organic solvent such as tetrahydrofuran, hexanes, toluene, or acetonitrile. Usually, more than one molar equivalent of the base relative to the ketone of Formula 8 used.

Alternatively small changes in the reaction conditions can be used to prepare compounds of Formula 2 directly from compounds of Formula 6 and compounds of Formula 8. For example suitable conditions, such as treatment with a mixture comprising potassium carbonate and acetonitrile at about 82° C., can be used to prepare compounds of Formula 2. Compounds of Formula 2 can also be prepared directly from compounds of Formula 6 and compounds of Formula 8 by treatment with calcium hydroxide in N,N-dimethylformamide and tent-butyl methyl ether, and then heating the mixture to reflux with azeotropic removal of water. These reactions are usually conducted at temperatures ranging from about 25° C. to the boiling point of the solvent(s).

If the reaction is conducted using a base such as lithium diisopropylamide or lithium bis(trimethylsilyl)amide, which may react with compounds of Formula 6 wherein R$^1$ is CF$_3$ (Gosselin et al., *Organic Letters* 2005, 7, 355), the order of addition of the components of the reaction becomes important. The most preferred order of addition is the metered addition of a ketone of Formula 8 to a base such as lithium diisopropylamide at about −78° C. in a solvent such as tetrahydrofuran. The enolate formed can then be contacted with a compound of Formula 6 at about −78° C. to afford the desired compound of Formula 3. The product can be isolated by methods well known to one skilled in the art such as extraction, crystallization, etc.

Ketones of Formula 6 and Formula 8 can be prepared by numerous methods described in the general literature.

In another aspect of the present invention, certain compounds of Formula 1 (e.g., compounds of Formula 1 wherein Q is Q$^b$ and Q$^b$ is 1-naphthalenyl substituted in the 4-position with —C(=O)OR$^5$) prepared by the method of Scheme 1, are useful for preparing compounds of Formula 1a, which are particularly useful as insecticides.

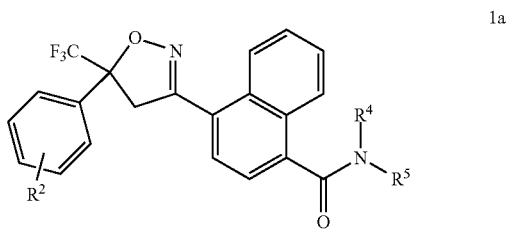

wherein R$^2$, R$^4$ and R$^5$ are as defined in the Summary of the Invention. A variety of routes are possible for the preparation of compounds of Formula 1a from compounds of Formula 1.

As outlined in Scheme 6, one such method involves the aminocarbonylation of a compound of Formula 1b with an appropriately substituted amine compound of Formula 9 wherein R$^2$, R$^4$ and R$^5$ are defined in the Summary of the Invention.

Scheme 6

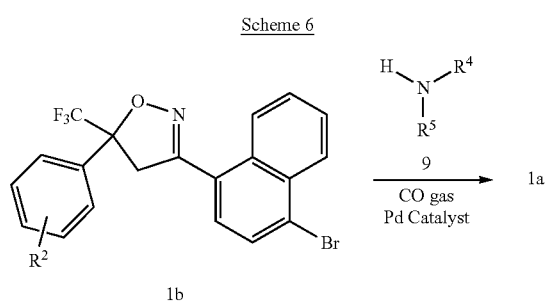

This reaction is typically carried out with an aryl bromide of Formula 1b in the presence of a palladium catalyst under a CO atmosphere. The palladium catalyst used for the present method typically comprises palladium in a formal oxidation state of either 0 (i.e. Pd(0)) or 2 (i.e. Pd(II)). A wide variety of such palladium-containing compounds and complexes are useful as catalysts for the present method. Examples of palladium-containing compounds and complexes useful as catalysts in the method of Scheme 6 include PdCl$_2$(PPh$_3$)$_2$ (bis(triphenylphosphine)palladium(II) dichloride), Pd(PPh$_3$)$_4$ (tetrakis(triphenylphosphine)palladium(0)), Pd(C$_5$H$_7$O$_2$)$_2$ (palladium(II) acetylacetonate), Pd$_2$(dba)$_3$ (tris(dibenzylideneacetone)dipalladium(0)), and [1,1-bis (diphenylphosphino)-ferrocene]dichloropalladium(II). The method of Scheme 6 is generally conducted in a liquid phase, and therefore to be most effective the palladium catalyst preferably has good solubility in the liquid phase. Useful solvents include, for example, ethers such as 1,2-dimethoxyethane, amides such as N,N-dimethylacetamide, and non-halogenated aromatic hydrocarbons such as toluene.

The method of Scheme 6 can be conducted over a wide range of temperatures, ranging from about 25 to about 150° C. Of note are temperatures from about 60 to about 110° C., which typically provide fast reaction rates and high product yields. The general methods and procedures for aminocarbonylation with an aryl bromide and an amine are well known in the literature; see, for example, H. Horino et al., *Synthesis* 1989, 715; and J. J. Li, G. W. Cribble, editors, *Palladium in Heterocyclic Chemistry: A Guide for the Synthetic Chemist*, 2000.

Another method of preparing compounds of Formula 1a is shown in Scheme 7. In this method a carboxylic acid of Formula 1c is coupled with an appropriately substituted amine compound of Formula 9.

Scheme 7

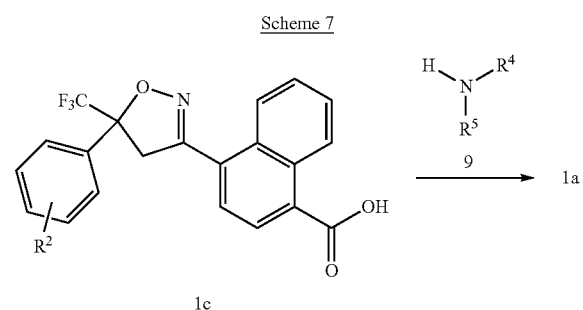

This reaction is generally carried out in the presence of a dehydrating coupling reagent such as dicyclohexylcarbodiimide, 1-(3-dimethylaminopropyl)-3-ethylcarbodiimide, 1-propanephosphonic acid cyclic anhydride or carbonyl diimidazole in the presence of a base such as triethylamine, pyridine, 4-(dimethylamino)pyridine or N,N-diisopropylethylamine in an anhydrous aprotic solvent such as dichloromethane or tetrahydrofuran at a temperature typically between 25 and 70° C.

Compounds of Formula 1c can be prepared by hydrolysis of esters of Formula 1d, wherein R$^5$ is methyl or ethyl, as shown in Scheme 8.

Scheme 8

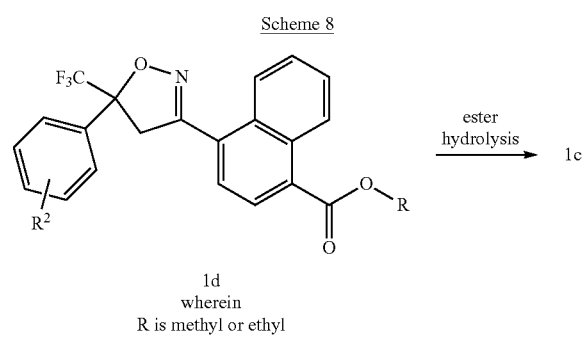

1d
wherein
R is methyl or ethyl

In the method of Scheme 8, an ester of Formula 1d is converted to a corresponding carboxylic acid of Formula 1c by general procedures well known in the art. For example, treatment of a methyl or ethyl ester of Formula 1d with aqueous lithium hydroxide in tetrahydrofuran, followed by acidification yields the corresponding carboxylic acid of Formula 1c.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Synthesis Examples are, therefore, to be construed as merely illustrative, and not limiting of the disclosure in any way whatsoever. Steps in the following Synthesis Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "ABq means AB quartet, "m" means multiplet, "dd" means doublet of doublets, "dt" means doublet of triplets and "br" means broad. The symbol "~" means approximately. LCMS refers to liquid chromatography-mass spectrometry.

Synthesis Example 1

Preparation of 1-(4-bromo-3-methylphenyl)-3-(3,5-dichlorophenyl)-4,4,4-trifluoro-2-buten-1-one Step A: Preparation of
4-bromo-N-methoxy-N,3-dimethylbenzamide A stirred suspension of 4-bromo-3-methylbenzoic acid (15 g, 69.0 mmol) in thionyl chloride (60 mL) was heated at reflux for 2 h and then concentrated under reduced pressure. The residual acyl chloride was dissolved in dichloromethane (300 mL) and added to a stirred solution of N,O-dimethylhydroxylamine hydrochloride (7.2 g, 72.0 mmol) and pyridine (16.8 mL, 207.0 mmol) in dichloromethane (450 mL) at −20° C.

The reaction mixture was allowed to warm to room temperature overnight and then washed with 1 M aqueous potassium carbonate solution. The aqueous solution was extracted with dichloromethane. The organic extracts were concentrated under reduced pressure. The residue was purified by chromatography on silica gel using 50% ethyl acetate/hexanes as eluent to afford the title product as a pale yellow oil (17.81 g, 69.0 mmol, 100% yield).

$^1$H NMR (CDCl$_3$): 7.55 (m, 2H), 7.37 (m, 1H), 3.54 (s, 3H), 3.34 (s, 3H), 2.42 (s, 3H).

Step B: Preparation of 1-(4-bromo-3-methylphenyl)-3-(3,5-dichlorophenyl)-4,4,4-trifluoro-2-buten-1-one To a stirred solution of diisopropylamine (11.1 mL, 83.3 mmol) in tetrahydrofuran (100 mL) at −78° C. was added 2.5 M n-BuLi in hexanes (33.31 mL, 83.3 mmol). The reaction mixture was allowed to warm to 0° C., stirred for 20 minutes, and then cooled to −78° C. 2-Bromo-3,3,3-trifluoropropene (6.78 g, 38.7 mmol) was added to the reaction mixture, which was stirred for 30 minutes. Then a solution of 4-bromo-N-methoxy-N,3-dimethylbenzamide (i.e. the title product of Step A) (5.0 g, 19.4 mmol) in tetrahydrofuran (20 mL) was added to the reaction mixture at −78° C., which was then warmed to 0° C. Water (25 mL) was added to the mixture, which was then stirred for 1 hour at 0° C. The reaction mixture was extracted with ether and concentrated under reduced pressure, and the oily residue was purified by chromatography on silica gel to afford a mixture of 3-[bis (1-methylethyl)amino]-1-(4-bromo-3-methylphenyl)-4,4,4-trifluoro-2-buten-1-one and 1-(4-bromo-3-methylphenyl)-4,4,4-trifluoro-3-(methoxymethylamino)-2-buten-1-one (2.5:1 ratio by LCMS) (6.55 g, approx. 92% yield) as a bright orange oil.

This crude mixture (3 g, approx. 8.5 mmol) was diluted with tetrahydrofuran (40 mL) and cooled to −78° C., and 3,5-dichlorophenylmagnesium bromide (0.5 M in tetrahydrofuran) (51 mL, 25.5 mmol) was added. The reaction mixture was warmed to room temperature and stirred for 2 h, then quenched with an aqueous solution of saturated ammonium chloride, and extracted with diethyl ether. The organic solution was concentrated under reduced pressure, and the residual oil was purified by chromatography on silica gel using 10% ethyl acetate/hexanes as eluent to afford the title product as a yellow oil (3.24 g, 87% yield).

Synthesis Example 2

Preparation of 1-(4-bromo-2-naphthalenyl)-3-(3,5-dichlorophenyl)-4,4,4-trifluoro-2-buten-1-one Step A: Preparation of 1-(4-bromo-1-naphthalenyl)-3-(3,5-dichlorophenyl)-4,4,4-trifluoro-3-hydroxy-1-butanone Lithium diisopropylamide (Aldrich Chemical Company, 2M in tetrahydrofuran/ethylbenzene, 4 mL, 7.94 mmol) was added to tetrahydrofuran (4 mL) at −78° C. A solution of 1-(4-bromo-1-naphthalenyl)ethanone (1.8 g, 7.22 mmol) in tetrahydrofuran (4 mL) was added dropwise to the mixture. When the addition was complete the mixture was stirred for 30 min at −78° C. Then a solution of 1-(3,5-dichlorophenyl)-2,2,2-trifluoroethanone (1.75 g, 7.20 mmol) in tetrahydrofuran (4 mL) was added dropwise to the mixture at such a rate that the temperature of the reaction mixture did not exceed −55° C. The mixture was allowed to warm to ambient temperature over 120 min. The mixture was then poured into 1N hydrochloric acid (100 mL) and extracted with ethyl acetate (2×100 mL). The combined extracts were dried and evaporated. Chromatography on silica gel (eluted with 1:9 ethyl acetate/hexanes) and crystallization from hexanes gave the title product as a white solid (1.1 g, 40% yield) melting at 74.5-75° C. (after recrystallization from hexanes).

IR (nujol) 3409, 1684, 1569, 1505, 1407, 1343, 1232, 1170, 1141, 1121 cm$^{-1}$.

$^1$H NMR (CDCl$_3$) δ 8.38-8.30 (m, 2H), 7.90 (d, J=7.7 Hz, 1H), 7.73-7.61 (m, 3H), 7.52 (s, 2H), 7.36 (t, J=1.8 Hz, 1H), 5.86 (s, 1H), 3.87 (½ABq, J=17.1 Hz, 1H), 3.80 (½ABq, J=17.1 Hz, 1H).

Step B: Preparation of 1-(4-bromo-1-naphthalenyl)-3-(3,5-dichlorophenyl)-4,4,4-trifluoro-2-buten-1-one A solution of thionyl chloride (0.5 g, 4.46 mmol) in toluene (2 mL) was added dropwise to the product of Step A (1.1 g, 2.23 mmol) in toluene (10 mL) at 65° C. The mixture was cooled to ambient temperature and then poured into 1N hydrochloric acid (50 mL). The resulting mixture was extracted with ethyl acetate (2×25 mL). The combined extracts were dried and evaporated to give the title product as an oil (1.0 g, 95% yield).

$^1$H NMR (CDCl$_3$) δ 9.16-9.13 (m, ~0.23H), 8.51-8.45 (m, ~0.77H), 8.40-8.39 (d, ~0.23H), 8.30-8.26 (m, 0.77H), 7.91-6.99 (m, 8H).

Synthesis Example 3

Preparation of 1-(3-bromo-4-fluorophenyl)-3-(3,5-dichlorophenyl)-4,4,4-trifluoro-2-buten-1-one Step A: Preparation of 1-(3-bromo-4-fluorophenyl)-3-(3,5-dichlorophenyl)-4,4,4-trifluoro-3-hydroxy-1-butanone Lithium diisopropylamide (Aldrich Chemical Company, 2M in tetrahydrofuran/ethylbenzene 10.18 mL, 20.36 mmol) was added to tetrahydrofuran (8 mL) at −78° C. A solution of 1-(3-bromo-4-fluorophenyl)ethanone (4.01 g, 18.47 mmol) in tetrahydrofuran (8 mL) was added dropwise to the mixture. When the addition was complete the mixture was stirred at −78° C. for 30 min. Then a solution of 1-(3,5-dichlorophenyl)-2,2,2-trifluoroethanone (4.50 g, 18.52 mmol) in tetrahydrofuran (8 mL) was added dropwise to the mixture so the temperature of the reaction mixture did not exceed −60° C. After the addition was complete the mixture was stirred at −78° C. for 60 min. The mixture was allowed to warm to 0° C. and then poured into 1N hydrochloric acid (100 mL). The mixture was extracted with ethyl acetate (2×100 mL), and the combined extracts were dried and evaporated. Chromatography of the residue on silica gel (eluted with 1:4 ethyl acetate/hexanes) gave the title product as a white solid (3.32 g, 39% yield) melting at 134-135° C. (after crystallization from ethyl acetate/hexanes).

IR (nujol) 3466, 1679, 1591, 1571, 1346, 1252, 1236, 1213, 1185, 1159, 1142, 1054, 825, 803 cm$^{-1}$.

$^1$H NMR (CDCl$_3$), δ 8.16 (dd, J=6.5, 2.2 Hz, 1H), 7.94-7.89 (m, 1H), 7.48 (s, 2H), 7.36 (s, 1H), 7.26 (t, J=8.2 Hz, 1H), 5.55 (s, 1H), 3.80 (½ ABq, J=17.5 Hz, 1H), 3.65 (½ ABq, J=17.5 Hz, 1H).

Step B: Preparation of 1-(3-bromo-4-fluorophenyl)-3-(3,5-dichlorophenyl)-4,4,4-trifluoro-2-buten-1-one To a solution of thionyl chloride (0.618 g, 5.52 mmol) in toluene (1 mL) was added to a mixture of the product from Step A (1.2 g, 2.60 mmol) and pyridine (0.41 g, 5.18 mmol) in toluene (15 mL) at 60-65° C. When the addition was complete, pyridine (0.2 g, 2.53 mmol) was added incrementally to the reaction mixture. When the addition was complete, the mixture was allowed to cool to ambient temperature and then poured into 1N hydrochloric acid (100 mL). The resulting mixture was extracted with ethyl acetate (2×50 mL) and the combined extracts dried and evaporated to give the title product as an oil (1.12 g, 97% yield).

IR (neat) 1681, 1588, 1561, 1492, 1399, 1282, 1211, 1185, 1139, 1048, 866, 822, 806, 709 cm$^{-1}$.

$^1$H NMR (CDCl$_3$), δ 8.21-8.18 (m, ~0.18H), 8.06-8.03 (m, ~0.82H), 7.92-7.88 (m, ~0.18H), 7.80-7.76 (m, ~0.82H), 7.49-6.81 (m, 5H).

Synthesis Example 4

Preparation of 3-(4-bromo-1-naphthalenyl)-5-(3,5-dichlorophenyl)-4,5-dihydro-5-(trifluoromethyl)isoxazole To a solution of hydroxylamine sulfate (0.18 g, 1.10 mmol) in water (1 mL) was added a solution of sodium carbonate (0.7 g, 6.6 mmol) in water (2 mL). The resulting mixture was added to a solution of the product of Synthesis Example 2, Step B (0.7 g, 1.48 mmol) in isopropanol (11 mL). The mixture was stirred at ambient temperature overnight. A further portion of the hydroxylamine sulfate (0.18 g, 1.09 mmol), sodium carbonate (0.7 g, 6.6 mmol), and water (3 mL) mixture was prepared as before and then added to the reaction mixture. After stirring for a further 24 h the mixture was poured into water (25 mL), and the resulting mixture was extracted with ethyl acetate (2×25 mL). The combined extracts were dried and evaporated under reduced pressure. Chromatography of the residue on silica gel (eluted with hexanes/ether, 9:1) gave the title product as a white solid (0.35 g, 48%) melting at 131-132° C. (after recrystallization from hexanes).

IR (nujol) 1591, 1569, 1508, 1426, 1329, 1303, 1280, 1261, 1191, 1170, 1127, 1011, 898, 821, 801 cm$^{-1}$.

$^1$H NMR (CDCl$_3$) δ 8.92-8.88 (m, 1H), 8.38-8.34 (m, 1H), 7.82 (d, J=7.7Hz, 1H), 7.71-7.68 (m, 2H), 7.57 (d, J=1.3 Hz, 2H), 7.46 (d, J=2 Hz, 1H), 7.37 (d, J=7.7 Hz, 1H), 4.27 (½ ABq, J=17.1 Hz, 1H), 3.90 (½ ABq, J=18.1 Hz, 1H).

Synthesis Example 5

Preparation of 3-(3-bromo-4-fluorophenyl)-5-(3,5-dichlorophenyl)-4,5-dihydro-5-(trifluoromethyl)isoxazole Aqueous sodium hydroxide (50%, 1.36 g, 17.0 mmol) was added to a solution of hydroxylamine sulfate (0.70 g, 4.26 mmol) in water (8 mL). When the mixture had cooled to ambient temperature it was added to a solution of the product of Synthesis Example 3, Step B (1.8 g, 4.07 mmol) in tetrahydrofuran (20 mL). After the addition was complete the mixture was stirred for 20 min. The mixture was poured into water (150 mL), and the resulting mixture was extracted with ethyl acetate (2×100 mL). The combined extracts were dried and evaporated. Crystallization from hexanes gave the title product as an off-white solid (1.44 g, 77%) melting at 132-132.5° C. (after recrystallization from hexanes).

IR (nujol) 1570, 1500, 1422, 1407, 1341, 1302, 1274, 1179, 1166, 1118, 1012, 913, 862, 822, 801 cm$^{-1}$.

$^1$H NMR (CDCl$_3$) δ 7.86 (dd, J=6.3, 2.4 Hz, 1H), 7.66-7.61 (m, 1H), 7.50 (d, J=1.3 Hz, 1H), 7.44-7.43 (m, 1H), 7.19 (t, J=8.4 Hz, 1H), 4.05 (½ ABq, J=17.4 Hz, 1H), 3.67 (½ ABq, J=17.1 Hz, 1H).

Synthesis Example 6

Preparation of 3-(4-bromo-2-methylphenyl)-5-(3,5-dichlorophenyl)-4,5-dihydro-5-(trifluoromethyl)isoxazole To a stirred solution of 1-(4-bromo-2-methylphenyl)-3-(3,5-dichlorophenyl)-4,4,4-trifluoro-2-buten-1-one (200 mg, 0.45 mmol) in pyridine (3 mL) at room temperature was added hydroxylamine hydrochloride (47 mg, 0.68 mmol). The reaction mixture was heated to reflux for 4 h. The resulting mixture was cooled to room temperature and then concentrated, and the residual oil was purified by chromatography on silica gel using 20:80 ethyl acetate/hexanes as eluent to afford the title product as a pale yellow oil (50 mg, 24% yield).

$^1$H NMR (CDCl$_3$): 7.17-7.50 (m, 6H), 4.11 (d, 1H), 3.74 (d, 1H), 2.54 (s, 3H).

Synthesis Example 7

Preparation of 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide Step A: Preparation of 4-acetyl-1-naphthalenecarbonyl chloride Thionyl chloride (35.00 g, 0.29 mol) was added to 4-acetyl-1-naphthalenecarboxylic acid (51.70 g, 0.24 mol) in toluene (350 mL). The mixture was warmed to 90° C. for 8.5 h. After cooling to 25° C., the solvent was removed under reduced pressure to give the title product as an off-white solid (55.1 g, 98.7% yield).

IR (nujol) 1758, 1681, 1515, 1352, 1282, 1245, 1218, 1190, 1117, 1053, 923, 762 cm$^{-1}$.

$^1$H NMR (CDCl$_3$): 8.72-8.69 (m, 1H), 8.50 (d, J=7.6 Hz, 1H), 8.44-8.41 (m, 1H), 7.82 (d, J=7.9 Hz, 1H), 7.76-7.65 (m, 2H), 2.77 (s, 3H).

Step B: Preparation of 4-acetyl-N-[2-oxo-2-[(2,2,2-trifluoroethyl)amino]ethyl]-1-naphthalenecarboxamide A solution of 2-amino-N-(2,2,2-trifluoroethyl)acetamide (21.90 g, 0.14 mol) in 1,2-dichloroethane (80 mL) was added dropwise over 15 min to the product of Synthesis Example 7, Step A (32.50 g, 0.14 mol) in 1,2-dichloroethane (160 mL) at a temperature of 25 to 30° C. The resulting mixture was further stirred for 10 min at 25° C. Triethylamine (14.20 g, 0.14 mol) in 1,2-dichloroethane (80 mL) was then added dropwise over 44 min at 25° C., and the mixture was stirred further for 20 min at 25° C. The solvent was removed under reduced pressure, and the residue was dissolved in hot acetonitrile (50 mL). The mixture was then cooled to 25° C., and water (40 mL) was added dropwise. The mixture was further cooled to 0° C. and filtered. The isolated solid was washed with water (100 mL) and dried overnight in a vacuum oven (approximately 16-33 kPa at 50° C.) to provide the title product as an off-white solid (37 g, 75% yield) melting at 169-169° C.

IR (nujol) 3303, 3233, 3072, 1698, 1683, 1636, 1572, 1548, 1447, 1279, 1241, 1186, 1159 cm[1].

$^1$H NMR (CD$_3$S(=O)CD$_3$): 8.95 (t, J=5.8 Hz, 1H), 8.72 (t, J=6.5 Hz, 1H), 8.55 (dd, J=6.5, 2 Hz, 1H), 8.37-8.33 (m, 1H), 8.13 (d, J=7.3 Hz, 1H), 7.70-7.60 (m, 3H), 4.07-3.95 (m, 4H), 2.75 (s, 3H).

Step C: Preparation of 4-[3-[3-chloro-5-(trifluoromethyl)phenyl]-4,4,4-trifluoro-1-oxo-2-buten-1-yl]-N-[2-oxo-2-[(2,2,2-trifluoroethyl)amino]ethyl]-1-naphthalenecarboxamide A mixture of the product of Synthesis Example 7, Step B (10.00 g, 28.38 mmol), 1-[3-chloro-5-(trifluoromethyl)phenyl]-2,2,2-trifluoroethanone (9.00 g, 32.5 mmol), calcium hydroxide (1.05 g, 14.2 mmol), N,N-dimethylformamide (20 mL) and tert-butyl methyl ether (32 mL) was placed in a thermometer-equipped reaction vessel. The reaction vessel was connected to a ten-plate Oldershaw column, the output of which was condensed and fed into a decanter initially filled with tert-butyl methyl ether. A nitrogen atmosphere was maintained in the apparatus. The upper part of the decanter was connected to return condensate to the fifth plate of the Oldershaw column. This arrangement ensured that wet (containing dissolved water) tert-butyl methyl ether was not returned from the decanter to the reaction vessel. A drain valve at the bottom of the decanter allowed removing tert-butyl methyl ether in addition to water from the decanter. The reaction mixture was heated to distill the tert-butyl methyl ether/water azeotrope. As the decanter trap contained an amount of tert-butyl methyl ether sufficient to dissolve all of the water formed by the reaction, the condensate in the trap did not separate into layers containing predominately water and predominately tert-butyl methyl ether. Because the reaction mixture initially contained mostly tert-butyl methyl ether, the mixture boiled at a temperature not much exceeding the normal boiling point of tert-butyl methyl ether (e.g., about 65-70° C.). The reaction proceeded relatively slowly at this temperature, so condensate was gradually drained from the decanter trap to remove tert-butyl methyl ether. As the concentration of tert-butyl methyl ether decreased in the reaction mixture, the temperature of the boiling mixture increased. Tert-butyl methyl ether was removed by draining the decanter until the temperature of the boiling reaction mixture reached about 85° C. To maintain this temperature, tert-butyl methyl ether was added as needed to compensate for loss of solvent from the apparatus. The total time from the start of heating the reaction mixture to stopping distillation, not including a shut-down period overnight, was about 6 h.

To isolate the product, the mixture was cooled to room temperature and was added to a mixture of tert-butyl methyl ether (50 mL) and 1N hydrochloric acid (100 mL). The organic phase was separated, and heptane (60 mL) was added dropwise. The mixture was filtered to provide the title product as an off white solid mixture of isomers (14 g, 81% yield) melting at 174.5-177° C.

IR (nujol) 3294, 1697, 1674, 1641, 1541, 1441, 1364, 1313, 1275, 1246, 1163, 1104 cm$^{-1}$.

$^1$H NMR (CD$_3$S(=O)CD$_3$): (major isomer) 8.91 (t, J=6.2 Hz, 1H), 8.73 (t, J=6.4 Hz, 1H), 8.44-8.30 (m, 2H), 8.18 (d, J=7.7 Hz, 1H), 7.97-7.61 (m, 7H), 4.06-3.95 (m, 4H).

Step D: Preparation of 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide Aqueous sodium hydroxide (50%, 3.04 g, 38.0 mmol) was added dropwise to a stirred solution of hydroxylamine sulphate (1.48 g, 9.02 mmol) in water (28 mL) at 25° C. After this addition was complete the product of Synthesis Example 7, Step C (10.00 g, 16.33 mmol) in tetrahydrofuran (60 mL) was added dropwise over 40 min. After the addition was complete the mixture was stirred further for 30 min. The solvent was removed under reduced pressure and 1N hydrochloric acid (100 mL) was added. The mixture was extracted with ether (2×100 mL) and the combined extracts were dried and evaporated. The residue was dissolved in acetonitrile (30 mL), cooled to 0° C., and filtered to afford the title product as a white solid (7.84 g, 77% yield) melting at 107-108.5° C. (after recrystallisation from acetonitrile).

IR (nujol) 3312, 1681, 1642, 1536, 1328, 1304, 1271, 1237, 1173, 1116 cm$^{-1}$.

$^1$H NMR (CD$_3$S(=O)CD$_3$): 8.98 (t, J=5.8 Hz, 1H), 8.82 (d, J=7.4 Hz, 1H), 8.74 (t, J=6.5 Hz, 1H), 8.40 (d, J=9.7 Hz, 1H), 8.09 (d, J=15.3 Hz, 2H), 7.93 (d, J=7.6 Hz, 2H), 7.75-7.04 (m, 3H), 4.63 (s, 2H), 4.07-3.96 (4H, m).

Synthesis Example 8

Preparation of methyl 4-[5-[3-chloro-5-(trifluoromethyl)phenyl]-4,5-dihydro-5-(trifluoromethyl)-3-isoxazolyl]-1-naphthalenecarboxylate Step A: Preparation of methyl 4-[3-[3-chloro-5-(trifluoromethyl)phenyl]-4,4,4-trifluoro-1-oxo-2-buten-1-yl]-1-naphthalenecarboxylate A mixture of methyl 4-acetyl-1-naphthalenecarboxylate (7.83 g, 34.3 mmol), 1-[3-chloro-5-(trifluoromethyl)phenyl]-2,2,2-trifluoroethanone (10.43 g, 37.71 mmol), calcium hydroxide (1.25 g, 16.9 mmol), N,N-dimethylformamide (27 mL) and tert-butyl methyl ether (44 mL) was heated to reflux. The tert-butyl methyl ether/water azeotrope was removed as described in Synthesis Example 7, Step C. As the decanter trap contained an amount of tert-butyl methyl ether sufficient to dissolve all of the water formed by the reaction, the condensate in the trap did not separate into layers containing predominately water and predominately tert-butyl methyl ether. Tert-butyl methyl ether was removed by gradually draining the decanter trap until the reaction temperature was 85° C. To maintain this temperature, tert-butyl methyl ether was added as needed to compensate for loss of solvent from the apparatus. The total time from the start of heating the reaction mixture to stopping distillation was about 4.5 h.

The mixture was cooled to 25° C. and poured into a mixture of 0.5 N hydrochloric acid (100 mL) and tert-butyl methyl ether (50 mL). The mixture was acidified with concentrated hydrochloric acid and evaporated, and the residue was crystallized from hexanes (40 mL) to give the title product as a yellow solid (13.24 g, 79% yield) melting at 90-90.5° C. (after recrystallization from hexanes).

IR (nujol) 3071, 1721, 1710, 1671, 1516, 1439, 1316, 1280, 1252, 1178, 1129, 1103, 1026, 888, 861 cm$^{-1}$.

$^1$H NMR (CDCl$_3$): 8.77-8.73 (m, 1H), 8.28-8.25 (m, 1H), 8.0 (d, J=7.6 Hz, 1H), 7.67-7.60 (m, 3H), 7.40 (d, J=1.4 Hz, 1H), 7.32 (s, 1H), 7.23 (s, 1H), 7.20 (s, 1H), 4.02 (s, 3H).

Step B: Preparation of methyl 4-[5-[3-chloro-5-(trifluoromethyl)phenyl]-4,5-dihydro-5-(trifluoromethyl)-3-isoxazolyl]-1-naphthalenecarboxylate Aqueous sodium hydroxide (50%, 2.08 g, 25.5 mmol) was added dropwise to a stirred solution of hydroxylamine sulfate (1.07 g, 6.52 mmol) in water (20 mL) at 25° C. After this addition was complete the product of Synthesis Example 8, Step A (5 g, 10.27 mmol) in tetrahydrofuran (20 mL) was added dropwise over 40 min. After the addition was complete the mixture was stirred further for 30 min. The organic phase was separated and added to hydrochloric acid (100 mL). The mixture was extracted with ethyl acetate (2×20 mL). The organic solvent was evaporated under reduced pressure. The residue was redissolved in acetic acid (16 mL) and then warmed to 100° C. Water (2 mL) was added dropwise and the mixture was cooled to 50° C. The mixture was seeded with a small amount of previously prepared methyl 4-[5-[3-chloro-5-(trifluoromethyl)phenyl]-4,5-dihydro-5-(trifluoromethyl)-3-isoxazolyl]-1-naphthalenecarboxylate and then cooled to 25° C. Water (2 mL) was added and the mixture was cooled to 0° C. The mixture was filtered and the solid was washed with acetic acid:water (8 mL:2 mL). The solid was dried in a vacuum oven to give the title product as a white solid (3.91 g, 76% yield) melting at 111.5-112° C. (after recrystallisation from acetonitrile).

IR (nujol) 1716, 1328, 1306, 1287, 1253, 1242, 1197, 1173, 1137, 1114, 1028, 771 cm$^{-1}$.

$^1$H NMR (CDCl$_3$): 8.90-8.87 (m, 1H), 8.82-8.79 (m, 1H), 8.10 (d, J=7.7 Hz), 7.87 (s, 1H), 7.81 (s, 1H), 7.72-7.67 (m, 3H) 7.55 (d, J=7.6 Hz, 1H), 4.34 (½ ABq, J=17.3 Hz, 1H), 4.03 (s, 3H), 3.93 (½ ABq, J=17.3 Hz, 1H).

The following compounds of Formula 2 defined in Tables 1 to 14 are prepared from corresponding hydroxy ketone compounds of Formula 3 as shown in Scheme 2 by the procedures described herein together with methods known in the art. The compounds listed in Tables 1 to 14 further illustrate the method of Scheme 1, as each of these specifically identified compounds contacted with hydroxylamine and in the presence of base is converted according to the method to specific corresponding 4,5-dihydroisoxazole compounds of Formula 1. In Tables 1-14: Et means ethyl, Me means methyl, CN means cyano, Ph means phenyl, Py means pyridinyl, c-Pr means cyclopropyl, i-Pr means isopropyl, t-Bu means tertiary butyl, SMe means methylthio, SO$_2$ means sulfonyl and Thz means thiazole. Concatenations of groups are abbreviated similarly; for example, "SO$_2$Me" means methylsulfonyl.

TABLE 1

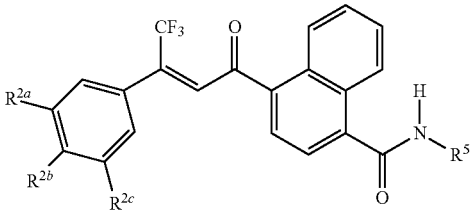

| $R^5$ | $R^5$ | $R^5$ |
|---|---|---|
| $R^{2a}$ is Cl, $R^{2b}$ is H, $R^{2c}$ is Cl | | |
| CH$_2$CH$_3$ | CH$_2$-c-Pr | CH$_2$CH$_2$SO$_2$Et |
| CH$_2$-i-Pr | CH$_2$CH$_2$SMe | CH$_2$CH$_2$SO$_2$(n-Pr) |
| CH$_2$CH$_2$Cl | CH(Me)CH$_2$SMe | CH$_2$CH$_2$CH$_2$SO$_2$Et |
| CH$_2$CH$_2$OH | CH$_2$CH$_2$CH$_2$SMe | CH$_2$C(O)NH(Me) |
| CH(Me)CH$_2$OH | CH$_2$CH$_2$S(O)Me | CH$_2$C(O)NH(n-Pr) |
| CH$_2$CH(Me)OH | CH(Me)CH$_2$S(O)Me | CH$_2$C(O)NH(s-Bu) |
| CH$_2$C(Me)$_2$OH | CH$_2$CH$_2$CH$_2$S(O)Me | CH$_2$C(O)NMe$_2$ |
| CH$_2$CH$_2$CH$_2$OH | CH$_2$CH$_2$SO$_2$Me | CH$_2$C(O)NMe(Et) |
| CH$_2$C(Me)$_2$CH$_2$OH | CH(Me)CH$_2$SO$_2$Me | CH(Me)C(O)NH(Me) |
| CH$_2$CH$_2$CH(Me)OH | CH$_2$CH$_2$CH$_2$SO$_2$Me | CH(Me)C(O)NH(Et) |
| CH$_2$C(O)N(H)Et | CH$_2$C(O)N(H)CH$_2$CF$_3$ | CH(Me)C(O)NH(n-Pr) |
| CH$_2$C(O)N(H)-i-Pr | CH(Me)C(O)N(H)CH$_2$CF$_3$ | CH(Me)C(O)NH(i-Pr) |
| CH$_2$C(O)N(H)CH$_2$-i-Pr | CH$_2$C(O)N(H)CH$_2$CH$_2$SMe | CH(Me)C(O)NH(s-Bu) |
| CH(Me)C(O)N(H)CH$_2$-i-Pr | CH$_2$C(O)N(H)CH$_2$CH$_2$SO$_2$Me | CH$_2$C(O)NHCH$_2$CHF$_2$ |
| CH$_2$C(O)N(H)CH$_2$CH$_2$Cl | | CH$_2$C(O)NHCH$_2$CH$_2$CF$_3$ |
| CH(Me)C(O)N(H)CH$_2$CH$_2$Cl | CH$_2$CH$_2$SEt | CH$_2$C(O)NHCH(Me)CF$_3$ |
| CH$_2$C(O)N(H)CH$_2$CH$_2$F | CH$_2$CH$_2$S(n-Pr) | CH$_2$C(O)NHCH$_2$CH(Me)CF$_3$ |
| CH(Me)C(O)N(H)CH$_2$CH$_2$F | CH$_2$CH$_2$CH$_2$SEt | CH(Me)C(O)NHCH$_2$CHF$_2$ |
| CH$_2$CF$_3$ | CH$_2$CH$_2$S(O)Et | CH(Me)C(O)NHCH$_2$CH$_2$CF$_3$ |
| CH$_2$-(2-Py) | CH$_2$CH$_2$S(O)(n-Pr) | CH(Me)C(O)NHCH(Me)CF$_3$ |
| CH$_2$-(4-Thz) | CH$_2$CH$_2$CH$_2$S(O)Et | CH(Me)C(O)NHCH$_2$CH(Me)CF$_3$ |
| $R^{2a}$ is Cl, $R^{2b}$ is Cl, $R^{2c}$ is Cl | | |
| CH$_2$CH$_3$ | CH$_2$-c-Pr | CH$_2$CH$_2$SO$_2$Et |
| CH$_2$-i-Pr | CH$_2$CH$_2$SMe | CH$_2$CH$_2$SO$_2$(n-Pr) |
| CH$_2$CH$_2$Cl | CH(Me)CH$_2$SMe | CH$_2$CH$_2$CH$_2$SO$_2$Et |
| CH$_2$CH$_2$OH | CH$_2$CH$_2$CH$_2$SMe | CH$_2$C(O)NH(Me) |
| CH(Me)CH$_2$OH | CH$_2$CH$_2$S(O)Me | CH$_2$C(O)NH(n-Pr) |
| CH$_2$CH(Me)OH | CH(Me)CH$_2$S(O)Me | CH$_2$C(O)NH(s-Bu) |
| CH$_2$C(Me)$_2$OH | CH$_2$CH$_2$CH$_2$S(O)Me | CH$_2$C(O)NMe$_2$ |
| CH$_2$CH$_2$CH$_2$OH | CH$_2$CH$_2$SO$_2$Me | CH$_2$C(O)NMe(Et) |
| CH$_2$C(Me)$_2$CH$_2$OH | CH(Me)CH$_2$SO$_2$Me | CH(Me)C(O)NH(Me) |
| CH$_2$CH$_2$CH(Me)OH | CH$_2$CH$_2$CH$_2$SO$_2$Me | CH(Me)C(O)NH(Et) |
| CH$_2$C(O)N(H)Et | CH$_2$C(O)N(H)CH$_2$CF$_3$ | CH(Me)C(O)NH(n-Pr) |
| CH$_2$C(O)N(H)-i-Pr | CH(Me)C(O)N(H)CH$_2$CF$_3$ | CH(Me)C(O)NH(i-Pr) |
| CH$_2$C(O)N(H)CH$_2$-i-Pr | CH$_2$C(O)N(H)CH$_2$CH$_2$SMe | CH(Me)C(O)NH(s-Bu) |
| CH(Me)C(O)N(H)CH$_2$-i-Pr | CH$_2$C(O)N(H)CH$_2$CH$_2$SO$_2$Me | CH$_2$C(O)NHCH$_2$CHF$_2$ |
| CH$_2$C(O)N(H)CH$_2$CH$_2$Cl | | CH$_2$C(O)NHCH$_2$CH$_2$CF$_3$ |
| CH(Me)C(O)N(H)CH$_2$CH$_2$Cl | CH$_2$CH$_2$SEt | CH$_2$C(O)NHCH(Me)CF$_3$ |

TABLE 1-continued

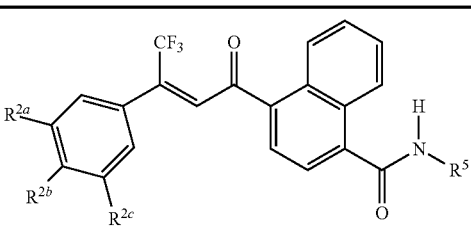

| R⁵ | R⁵ | R⁵ |
|---|---|---|
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |

R²ᵃ is Cl, R²ᵇ is F, R²ᶜ is Cl

| CH₂CH₃ | CH₂-c-Pr | CH₂CH₂SO₂Et |
|---|---|---|
| CH₂-i-Pr | CH₂CH₂SMe | CH₂CH₂SO₂(n-Pr) |
| CH₂CH₂Cl | CH(Me)CH₂SMe | CH₂CH₂CH₂SO₂Et |
| CH₂CH₂OH | CH₂CH₂CH₂SMe | CH₂C(O)NH(Me) |
| CH(Me)CH₂OH | CH₂CH₂S(O)Me | CH₂C(O)NH(n-Pr) |
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |
| CH₂C(O)N(H)CH₂CH₂Cl | | CH₂C(O)NHCH₂CH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |

R²ᵃ is Br, R²ᵇ is H, R²ᶜ is Br

| CH₂CH₃ | CH₂-c-Pr | CH₂CH₂SO₂Et |
|---|---|---|
| CH₂-i-Pr | CH₂CH₂SMe | CH₂CH₂SO₂(n-Pr) |
| CH₂CH₂Cl | CH(Me)CH₂SMe | CH₂CH₂CH₂SO₂Et |
| CH₂CH₂OH | CH₂CH₂CH₂SMe | CH₂C(O)NH(Me) |
| CH(Me)CH₂OH | CH₂CH₂S(O)Me | CH₂C(O)NH(n-Pr) |
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |
| CH₂C(O)N(H)CH₂CH₂Cl | | CH₂C(O)NHCH₂CH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |

R²ᵃ is CF₃, R²ᵇ is H, R²ᶜ is H

| CH₂CH₃ | CH₂-c-Pr | CH₂CH₂SO₂Et |
|---|---|---|
| CH₂-i-Pr | CH₂CH₂SMe | CH₂CH₂SO₂(n-Pr) |
| CH₂CH₂Cl | CH(Me)CH₂SMe | CH₂CH₂CH₂SO₂Et |
| CH₂CH₂OH | CH₂CH₂CH₂SMe | CH₂C(O)NH(Me) |
| CH(Me)CH₂OH | CH₂CH₂S(O)Me | CH₂C(O)NH(n-Pr) |
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |

TABLE 1-continued

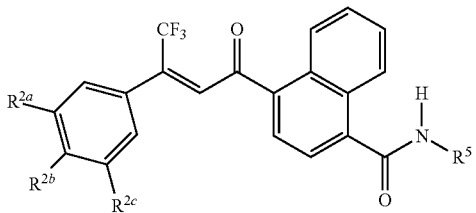

| R⁵ | R⁵ | R⁵ |
|---|---|---|
| CH₂C(O)N(H)CH₂CH₂Cl | | CH₂C(O)NHCH₂CH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |
| | R²ᵃ is CF₃, R²ᵇ is H, R²ᶜ is F | |
| CH₂CH₃ | CH₂-c-Pr | CH₂CH₂SO₂Et |
| CH₂-i-Pr | CH₂CH₂SMe | CH₂CH₂SO₂(n-Pr) |
| CH₂CH₂Cl | CH(Me)CH₂SMe | CH₂CH₂CH₂SO₂Et |
| CH₂CH₂OH | CH₂CH₂CH₂SMe | CH₂C(O)NH(Me) |
| CH(Me)CH₂OH | CH₂CH₂S(O)Me | CH₂C(O)NH(n-Pr) |
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |
| CH₂C(O)N(H)CH₂CH₂Cl | | CH₂C(O)NHCH₂CH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |
| | R²ᵃ is CF₃, R²ᵇ is H, R²ᶜ is Cl | |
| CH₂CH₃ | CH₂-c-Pr | CH₂CH₂SO₂Et |
| CH₂-i-Pr | CH₂CH₂SMe | CH₂CH₂SO₂(n-Pr) |
| CH₂CH₂Cl | CH(Me)CH₂SMe | CH₂CH₂CH₂SO₂Et |
| CH₂CH₂OH | CH₂CH₂CH₂SMe | CH₂C(O)NH(Me) |
| CH(Me)CH₂OH | CH₂CH₂S(O)Me | CH₂C(O)NH(n-Pr) |
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |
| CH₂C(O)N(H)CH₂CH₂Cl | | CH₂C(O)NHCH₂CH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |
| | R²ᵃ is CF₃, R²ᵇ is H, R²ᶜ is Br | |
| CH₂CH₃ | CH₂-c-Pr | CH₂CH₂SO₂Et |
| CH₂-i-Pr | CH₂CH₂SMe | CH₂CH₂SO₂(n-Pr) |
| CH₂CH₂Cl | CH(Me)CH₂SMe | CH₂CH₂CH₂SO₂Et |
| CH₂CH₂OH | CH₂CH₂CH₂SMe | CH₂C(O)NH(Me) |
| CH(Me)CH₂OH | CH₂CH₂S(O)Me | CH₂C(O)NH(n-Pr) |
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |

TABLE 1-continued

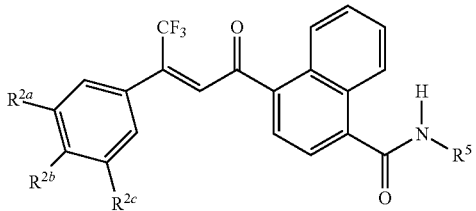

| R[5] | R[5] | R[5] |
|---|---|---|
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |
| CH₂C(O)N(H)CH₂CH₂Cl | | CH₂C(O)NHCH₂CH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |

R[2a] is CF₃, R[2b] is H, R[2c] is CF₃

| CH₂CH₃ | CH₂-c-Pr | CH₂CH₂SO₂Et |
| CH₂-i-Pr | CH₂CH₂SMe | CH₂CH₂SO₂(n-Pr) |
| CH₂CH₂Cl | CH(Me)CH₂SMe | CH₂CH₂CH₂SO₂Et |
| CH₂CH₂OH | CH₂CH₂CH₂SMe | CH₂C(O)NH(Me) |
| CH(Me)CH₂OH | CH₂CH₂S(O)Me | CH₂C(O)NH(n-Pr) |
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |
| CH₂C(O)N(H)CH₂CH₂Cl | | CH₂C(O)NHCH₂CH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |

R[2a] is OCF₃, R[2b] is H, R[2c] is Cl

| CH₂CH₃ | CH₂-c-Pr | CH₂CH₂SO₂Et |
| CH₂-i-Pr | CH₂CH₂SMe | CH₂CH₂SO₂(n-Pr) |
| CH₂CH₂Cl | CH(Me)CH₂SMe | CH₂CH₂CH₂SO₂Et |
| CH₂CH₂OH | CH₂CH₂CH₂SMe | CH₂C(O)NH(Me) |
| CH(Me)CH₂OH | CH₂CH₂S(O)Me | CH₂C(O)NH(n-Pr) |
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |
| CH₂C(O)N(H)CH₂CH₂Cl | | CH₂C(O)NHCH₂CH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |

R[2a] is OCH₂CF₃, R[2b] is H, R[2c] is F

| CH₂CH₃ | CH₂-c-Pr | CH₂CH₂SO₂Et |
| CH₂-i-Pr | CH₂CH₂SMe | CH₂CH₂SO₂(n-Pr) |
| CH₂CH₂Cl | CH(Me)CH₂SMe | CH₂CH₂CH₂SO₂Et |
| CH₂CH₂OH | CH₂CH₂CH₂SMe | CH₂C(O)NH(Me) |
| CH(Me)CH₂OH | CH₂CH₂S(O)Me | CH₂C(O)NH(n-Pr) |
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |

TABLE 1-continued

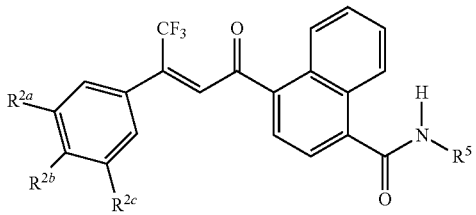

| R⁵ | R⁵ | R⁵ |
|---|---|---|
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |
| CH₂C(O)N(H)CH₂CH₂Cl | | CH₂C(O)NHCH₂CH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |
| R²ᵃ is OCH₂CF₃, R²ᵇ is H, R²ᶜ is Cl | | |
| CH₂CH₃ | CH₂-c-Pr | CH₂CH₂SO₂Et |
| CH₂-i-Pr | CH₂CH₂SMe | CH₂CH₂SO₂(n-Pr) |
| CH₂CH₂Cl | CH(Me)CH₂SMe | CH₂CH₂CH₂SO₂Et |
| CH₂CH₂OH | CH₂CH₂CH₂SMe | CH₂C(O)NH(Me) |
| CH(Me)CH₂OH | CH₂CH₂S(O)Me | CH₂C(O)NH(n-Pr) |
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |
| CH₂C(O)N(H)CH₂CH₂Cl | | CH₂C(O)NHCH₂CH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |
| R²ᵃ is OCH₂CF₃, R²ᵇ is H, R²ᶜ is Br | | |
| CH₂CH₃ | CH₂-c-Pr | CH₂CH₂SO₂Et |
| CH₂-i-Pr | CH₂CH₂SMe | CH₂CH₂SO₂(n-Pr) |
| CH₂CH₂Cl | CH(Me)CH₂SMe | CH₂CH₂CH₂SO₂Et |
| CH₂CH₂OH | CH₂CH₂CH₂SMe | CH₂C(O)NH(Me) |
| CH(Me)CH₂OH | CH₂CH₂S(O)Me | CH₂C(O)NH(n-Pr) |
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |
| CH₂C(O)N(H)CH₂CH₂Cl | | CH₂C(O)NHCH₂CH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |

TABLE 2

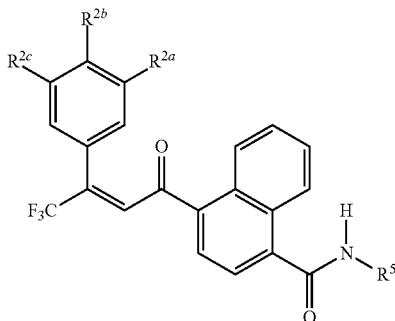

| R[5] | R[5] | R[5] |
|---|---|---|
| $R^{2a}$ is Cl, $R^{2b}$ is H, $R^{2c}$ is Cl | | |
| CH₂CH₃ | CH₂-c-Pr | CH₂CH₂SO₂Et |
| CH₂-i-Pr | CH₂CH₂SMe | CH₂CH₂SO₂(n-Pr) |
| CH₂CH₂Cl | CH(Me)CH₂SMe | CH₂CH₂CH₂SO₂Et |
| CH₂CH₂OH | CH₂CH₂CH₂SMe | CH₂C(O)NH(Me) |
| CH(Me)CH₂OH | CH₂CH₂S(O)Me | CH₂C(O)NH(n-Pr) |
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |
| CH₂C(O)N(H)CH₂CH₂Cl | | CH₂C(O)NHCH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |
| $R^{2a}$ is Cl, $R^{2b}$ is Cl, $R^{2c}$ is Cl | | |
| CH₂CH₃ | CH₂-c-Pr | CH₂CH₂SO₂Et |
| CH₂-i-Pr | CH₂CH₂SMe | CH₂CH₂SO₂(n-Pr) |
| CH₂CH₂Cl | CH(Me)CH₂SMe | CH₂CH₂CH₂SO₂Et |
| CH₂CH₂OH | CH₂CH₂CH₂SMe | CH₂C(O)NH(Me) |
| CH(Me)CH₂OH | CH₂CH₂S(O)Me | CH₂C(O)NH(n-Pr) |
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |
| CH₂C(O)N(H)CH₂CH₂Cl | | CH₂C(O)NHCH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |
| $R^{2a}$ is Cl, $R^{2b}$ is F, $R^{2c}$ is Cl | | |
| CH₂CH₃ | CH₂-c-Pr | CH₂CH₂SO₂Et |
| CH₂-i-Pr | CH₂CH₂SMe | CH₂CH₂SO₂(n-Pr) |
| CH₂CH₂Cl | CH(Me)CH₂SMe | CH₂CH₂CH₂SO₂Et |
| CH₂CH₂OH | CH₂CH₂CH₂SMe | CH₂C(O)NH(Me) |
| CH(Me)CH₂OH | CH₂CH₂S(O)Me | CH₂C(O)NH(n-Pr) |
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |
| CH₂C(O)N(H)CH₂-i-Pr | CH₂C(O)N(H)CH₂CH₂SMe | CH(Me)C(O)NH(s-Bu) |

TABLE 2-continued

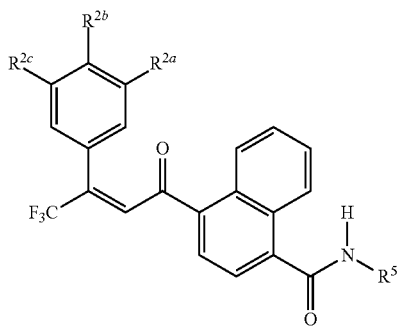

| $R^5$ | $R^5$ | $R^5$ |
|---|---|---|
| CH(Me)C(O)N(H)CH$_2$-i-Pr | CH$_2$C(O)N(H)CH$_2$CH$_2$SO$_2$Me | CH$_2$C(O)NHCH$_2$CHF$_2$ |
| CH$_2$C(O)N(H)CH$_2$CH$_2$Cl | | CH$_2$C(O)NHCH$_2$CH$_2$CF$_3$ |
| CH(Me)C(O)N(H)CH$_2$CH$_2$Cl | CH$_2$CH$_2$SEt | CH$_2$C(O)NHCH(Me)CF$_3$ |
| CH$_2$C(O)N(H)CH$_2$CH$_2$F | CH$_2$CH$_2$S(n-Pr) | CH$_2$C(O)NHCH$_2$CH(Me)CF$_3$ |
| CH(Me)C(O)N(H)CH$_2$CH$_2$F | CH$_2$CH$_2$CH$_2$SEt | CH(Me)C(O)NHCH$_2$CHF$_2$ |
| CH$_2$CF$_3$ | CH$_2$CH$_2$S(O)Et | CH(Me)C(O)NHCH$_2$CH$_2$CF$_3$ |
| CH$_2$-(2-Py) | CH$_2$CH$_2$S(O)(n-Pr) | CH(Me)C(O)NHCH(Me)CF$_3$ |
| CH$_2$-(4-Thz) | CH$_2$CH$_2$CH$_2$S(O)Et | CH(Me)C(O)NHCH$_2$CH(Me)CF$_3$ |
| | $R^{2a}$ is Br, $R^{2b}$ is H, $R^{2c}$ is Br | |
| CH$_2$CH$_3$ | CH$_2$-c-Pr | CH$_2$CH$_2$SO$_2$Et |
| CH$_2$-i-Pr | CH$_2$CH$_2$SMe | CH$_2$CH$_2$SO$_2$(n-Pr) |
| CH$_2$CH$_2$Cl | CH(Me)CH$_2$SMe | CH$_2$CH$_2$CH$_2$SO$_2$Et |
| CH$_2$CH$_2$OH | CH$_2$CH$_2$CH$_2$SMe | CH$_2$C(O)NH(Me) |
| CH(Me)CH$_2$OH | CH$_2$CH$_2$S(O)Me | CH$_2$C(O)NH(n-Pr) |
| CH$_2$CH(Me)OH | CH(Me)CH$_2$S(O)Me | CH$_2$C(O)NH(s-Bu) |
| CH$_2$C(Me)$_2$OH | CH$_2$CH$_2$CH$_2$S(O)Me | CH$_2$C(O)NMe$_2$ |
| CH$_2$CH$_2$CH$_2$OH | CH$_2$CH$_2$SO$_2$Me | CH$_2$C(O)NMe(Et) |
| CH$_2$C(Me)$_2$CH$_2$OH | CH(Me)CH$_2$SO$_2$Me | CH(Me)C(O)NH(Me) |
| CH$_2$CH$_2$CH(Me)OH | CH$_2$CH$_2$CH$_2$SO$_2$Me | CH(Me)C(O)NH(Et) |
| CH$_2$C(O)N(H)Et | CH$_2$C(O)N(H)CH$_2$CF$_3$ | CH(Me)C(O)NH(n-Pr) |
| CH$_2$C(O)N(H)-i-Pr | CH(Me)C(O)N(H)CH$_2$CF$_3$ | CH(Me)C(O)NH(i-Pr) |
| CH$_2$C(O)N(H)CH$_2$-i-Pr | CH$_2$C(O)N(H)CH$_2$CH$_2$SMe | CH(Me)C(O)NH(s-Bu) |
| CH(Me)C(O)N(H)CH$_2$-i-Pr | CH$_2$C(O)N(H)CH$_2$CH$_2$SO$_2$Me | CH$_2$C(O)NHCH$_2$CHF$_2$ |
| CH$_2$C(O)N(H)CH$_2$CH$_2$Cl | | CH$_2$C(O)NHCH$_2$CH$_2$CF$_3$ |
| CH(Me)C(O)N(H)CH$_2$CH$_2$Cl | CH$_2$CH$_2$SEt | CH$_2$C(O)NHCH(Me)CF$_3$ |
| CH$_2$C(O)N(H)CH$_2$CH$_2$F | CH$_2$CH$_2$S(n-Pr) | CH$_2$C(O)NHCH$_2$CH(Me)CF$_3$ |
| CH(Me)C(O)N(H)CH$_2$CH$_2$F | CH$_2$CH$_2$CH$_2$SEt | CH(Me)C(O)NHCH$_2$CHF$_2$ |
| CH$_2$CF$_3$ | CH$_2$CH$_2$S(O)Et | CH(Me)C(O)NHCH$_2$CH$_2$CF$_3$ |
| CH$_2$-(2-Py) | CH$_2$CH$_2$S(O)(n-Pr) | CH(Me)C(O)NHCH(Me)CF$_3$ |
| CH$_2$-(4-Thz) | CH$_2$CH$_2$CH$_2$S(O)Et | CH(Me)C(O)NHCH$_2$CH(Me)CF$_3$ |
| | $R^{2a}$ is CF$_3$, $R^{2b}$ is H, $R^{2c}$ is H | |
| CH$_2$CH$_3$ | CH$_2$-c-Pr | CH$_2$CH$_2$SO$_2$Et |
| CH$_2$-i-Pr | CH$_2$CH$_2$SMe | CH$_2$CH$_2$SO$_2$(n-Pr) |
| CH$_2$CH$_2$Cl | CH(Me)CH$_2$SMe | CH$_2$CH$_2$CH$_2$SO$_2$Et |
| CH$_2$CH$_2$OH | CH$_2$CH$_2$CH$_2$SMe | CH$_2$C(O)NH(Me) |
| CH(Me)CH$_2$OH | CH$_2$CH$_2$S(O)Me | CH$_2$C(O)NH(n-Pr) |
| CH$_2$CH(Me)OH | CH(Me)CH$_2$S(O)Me | CH$_2$C(O)NH(s-Bu) |
| CH$_2$C(Me)$_2$OH | CH$_2$CH$_2$CH$_2$S(O)Me | CH$_2$C(O)NMe$_2$ |
| CH$_2$CH$_2$CH$_2$OH | CH$_2$CH$_2$SO$_2$Me | CH$_2$C(O)NMe(Et) |
| CH$_2$C(Me)$_2$CH$_2$OH | CH(Me)CH$_2$SO$_2$Me | CH(Me)C(O)NH(Me) |
| CH$_2$CH$_2$CH(Me)OH | CH$_2$CH$_2$CH$_2$SO$_2$Me | CH(Me)C(O)NH(Et) |
| CH$_2$C(O)N(H)Et | CH$_2$C(O)N(H)CH$_2$CF$_3$ | CH(Me)C(O)NH(n-Pr) |
| CH$_2$C(O)N(H)-i-Pr | CH(Me)C(O)N(H)CH$_2$CF$_3$ | CH(Me)C(O)NH(i-Pr) |
| CH$_2$C(O)N(H)CH$_2$-i-Pr | CH$_2$C(O)N(H)CH$_2$CH$_2$SMe | CH(Me)C(O)NH(s-Bu) |
| CH(Me)C(O)N(H)CH$_2$-i-Pr | CH$_2$C(O)N(H)CH$_2$CH$_2$SO$_2$Me | CH$_2$C(O)NHCH$_2$CHF$_2$ |
| CH$_2$C(O)N(H)CH$_2$CH$_2$Cl | | CH$_2$C(O)NHCH$_2$CH$_2$CF$_3$ |
| CH(Me)C(O)N(H)CH$_2$CH$_2$Cl | CH$_2$CH$_2$SEt | CH$_2$C(O)NHCH(Me)CF$_3$ |
| CH$_2$C(O)N(H)CH$_2$CH$_2$F | CH$_2$CH$_2$S(n-Pr) | CH$_2$C(O)NHCH$_2$CH(Me)CF$_3$ |
| CH(Me)C(O)N(H)CH$_2$CH$_2$F | CH$_2$CH$_2$CH$_2$SEt | CH(Me)C(O)NHCH$_2$CHF$_2$ |
| CH$_2$CF$_3$ | CH$_2$CH$_2$S(O)Et | CH(Me)C(O)NHCH$_2$CH$_2$CF$_3$ |
| CH$_2$-(2-Py) | CH$_2$CH$_2$S(O)(n-Pr) | CH(Me)C(O)NHCH(Me)CF$_3$ |
| CH$_2$-(4-Thz) | CH$_2$CH$_2$CH$_2$S(O)Et | CH(Me)C(O)NHCH$_2$CH(Me)CF$_3$ |
| | $R^{2a}$ is CF$_3$, $R^{2b}$ is H, $R^{2c}$ is F | |
| CH$_2$CH$_3$ | CH$_2$-c-Pr | CH$_2$CH$_2$SO$_2$Et |
| CH$_2$-i-Pr | CH$_2$CH$_2$SMe | CH$_2$CH$_2$SO$_2$(n-Pr) |
| CH$_2$CH$_2$Cl | CH(Me)CH$_2$SMe | CH$_2$CH$_2$CH$_2$SO$_2$Et |
| CH$_2$CH$_2$OH | CH$_2$CH$_2$CH$_2$SMe | CH$_2$C(O)NH(Me) |
| CH(Me)CH$_2$OH | CH$_2$CH$_2$S(O)Me | CH$_2$C(O)NH(n-Pr) |

TABLE 2-continued

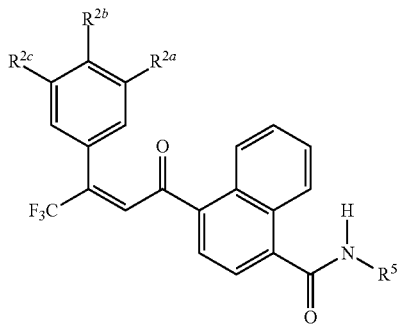

| R⁵ | R⁵ | R⁵ |
|---|---|---|
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |
| CH₂C(O)N(H)CH₂CH₂Cl | | CH₂C(O)NHCH₂CH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |
| | R²ᵃ is CF₃, R²ᵇ is H, R²ᶜ is Cl | |
| CH₂CH₃ | CH₂-c-Pr | CH₂CH₂SO₂Et |
| CH₂-i-Pr | CH₂CH₂SMe | CH₂CH₂SO₂(n-Pr) |
| CH₂CH₂Cl | CH(Me)CH₂SMe | CH₂CH₂CH₂SO₂Et |
| CH₂CH₂OH | CH₂CH₂CH₂SMe | CH₂C(O)NH(Me) |
| CH(Me)CH₂OH | CH₂CH₂S(O)Me | CH₂C(O)NH(n-Pr) |
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |
| CH₂C(O)N(H)CH₂CH₂Cl | | CH₂C(O)NHCH₂CH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |
| | R²ᵃ is CF₃, R²ᵇ is H, R²ᶜ is Br | |
| CH₂CH₃ | CH₂-c-Pr | CH₂CH₂SO₂Et |
| CH₂-i-Pr | CH₂CH₂SMe | CH₂CH₂SO₂(n-Pr) |
| CH₂CH₂Cl | CH(Me)CH₂SMe | CH₂CH₂CH₂SO₂Et |
| CH₂CH₂OH | CH₂CH₂CH₂SMe | CH₂C(O)NH(Me) |
| CH(Me)CH₂OH | CH₂CH₂S(O)Me | CH₂C(O)NH(n-Pr) |
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |
| CH₂C(O)N(H)CH₂CH₂Cl | | CH₂C(O)NHCH₂CH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |

TABLE 2-continued

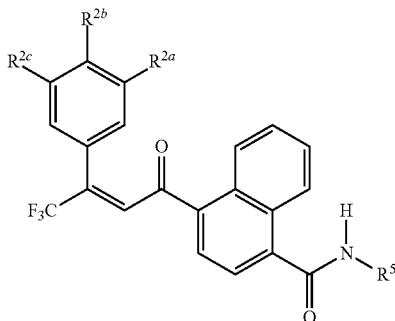

| $R^5$ | $R^5$ | $R^5$ |
|---|---|---|
| $CH_2$-(4-Thz) | $CH_2CH_2CH_2S(O)Et$ | $CH(Me)C(O)NHCH_2CH(Me)CF_3$ |
| | $R^{2a}$ is $CF_3$, $R^{2b}$ is H, $R^{2c}$ is $CF_3$ | |
| $CH_2CH_3$ | $CH_2$-c-Pr | $CH_2CH_2SO_2Et$ |
| $CH_2$-i-Pr | $CH_2CH_2SMe$ | $CH_2CH_2SO_2(n\text{-}Pr)$ |
| $CH_2CH_2Cl$ | $CH(Me)CH_2SMe$ | $CH_2CH_2CH_2SO_2Et$ |
| $CH_2CH_2OH$ | $CH_2CH_2CH_2SMe$ | $CH_2C(O)NH(Me)$ |
| $CH(Me)CH_2OH$ | $CH_2CH_2S(O)Me$ | $CH_2C(O)NH(n\text{-}Pr)$ |
| $CH_2CH(Me)OH$ | $CH(Me)CH_2S(O)Me$ | $CH_2C(O)NH(s\text{-}Bu)$ |
| $CH_2C(Me)_2OH$ | $CH_2CH_2CH_2S(O)Me$ | $CH_2C(O)NMe_2$ |
| $CH_2CH_2CH_2OH$ | $CH_2CH_2SO_2Me$ | $CH_2C(O)NMe(Et)$ |
| $CH_2C(Me)_2CH_2OH$ | $CH(Me)CH_2SO_2Me$ | $CH(Me)C(O)NH(Me)$ |
| $CH_2CH_2CH(Me)OH$ | $CH_2CH_2CH_2SO_2Me$ | $CH(Me)C(O)NH(Et)$ |
| $CH_2C(O)N(H)Et$ | $CH_2C(O)N(H)CH_2CF_3$ | $CH(Me)C(O)NH(n\text{-}Pr)$ |
| $CH_2C(O)N(H)\text{-}i\text{-}Pr$ | $CH(Me)C(O)N(H)CH_2CF_3$ | $CH(Me)C(O)NH(i\text{-}Pr)$ |
| $CH_2C(O)N(H)CH_2\text{-}i\text{-}Pr$ | $CH_2C(O)N(H)CH_2CH_2SMe$ | $CH(Me)C(O)NH(s\text{-}Bu)$ |
| $CH(Me)C(O)N(H)CH_2\text{-}i\text{-}Pr$ | $CH_2C(O)N(H)CH_2CH_2SO_2Me$ | $CH_2C(O)NHCH_2CHF_2$ |
| $CH_2C(O)N(H)CH_2CH_2Cl$ | | $CH_2C(O)NHCH_2CH_2CF_3$ |
| $CH(Me)C(O)N(H)CH_2CH_2Cl$ | $CH_2CH_2SEt$ | $CH_2C(O)NHCH(Me)CF_3$ |
| $CH_2C(O)N(H)CH_2CH_2F$ | $CH_2CH_2S(n\text{-}Pr)$ | $CH_2C(O)NHCH_2CH(Me)CF_3$ |
| $CH(Me)C(O)N(H)CH_2CH_2F$ | $CH_2CH_2CH_2SEt$ | $CH(Me)C(O)NHCH_2CHF_2$ |
| $CH_2CF_3$ | $CH_2CH_2S(O)Et$ | $CH(Me)C(O)NHCH_2CH_2CF_3$ |
| $CH_2$-(2-Py) | $CH_2CH_2S(O)(n\text{-}Pr)$ | $CH(Me)C(O)NHCH(Me)CF_3$ |
| $CH_2$-(4-Thz) | $CH_2CH_2CH_2S(O)Et$ | $CH(Me)C(O)NHCH_2CH(Me)CF_3$ |
| | $R^{2a}$ is $OCF_3$, $R^{2b}$ is H, $R^{2c}$ is Cl | |
| $CH_2CH_3$ | $CH_2$-c-Pr | $CH_2CH_2SO_2Et$ |
| $CH_2$-i-Pr | $CH_2CH_2SMe$ | $CH_2CH_2SO_2(n\text{-}Pr)$ |
| $CH_2CH_2Cl$ | $CH(Me)CH_2SMe$ | $CH_2CH_2CH_2SO_2Et$ |
| $CH_2CH_2OH$ | $CH_2CH_2CH_2SMe$ | $CH_2C(O)NH(Me)$ |
| $CH(Me)CH_2OH$ | $CH_2CH_2S(O)Me$ | $CH_2C(O)NH(n\text{-}Pr)$ |
| $CH_2CH(Me)OH$ | $CH(Me)CH_2S(O)Me$ | $CH_2C(O)NH(s\text{-}Bu)$ |
| $CH_2C(Me)_2OH$ | $CH_2CH_2CH_2S(O)Me$ | $CH_2C(O)NMe_2$ |
| $CH_2CH_2CH_2OH$ | $CH_2CH_2SO_2Me$ | $CH_2C(O)NMe(Et)$ |
| $CH_2C(Me)_2CH_2OH$ | $CH(Me)CH_2SO_2Me$ | $CH(Me)C(O)NH(Me)$ |
| $CH_2CH_2CH(Me)OH$ | $CH_2CH_2CH_2SO_2Me$ | $CH(Me)C(O)NH(Et)$ |
| $CH_2C(O)N(H)Et$ | $CH_2C(O)N(H)CH_2CF_3$ | $CH(Me)C(O)NH(n\text{-}Pr)$ |
| $CH_2C(O)N(H)\text{-}i\text{-}Pr$ | $CH(Me)C(O)N(H)CH_2CF_3$ | $CH(Me)C(O)NH(i\text{-}Pr)$ |
| $CH_2C(O)N(H)CH_2\text{-}i\text{-}Pr$ | $CH_2C(O)N(H)CH_2CH_2SMe$ | $CH(Me)C(O)NH(s\text{-}Bu)$ |
| $CH(Me)C(O)N(H)CH_2\text{-}i\text{-}Pr$ | $CH_2C(O)N(H)CH_2CH_2SO_2Me$ | $CH_2C(O)NHCH_2CHF_2$ |
| $CH_2C(O)N(H)CH_2CH_2Cl$ | | $CH_2C(O)NHCH_2CH_2CF_3$ |
| $CH(Me)C(O)N(H)CH_2CH_2Cl$ | $CH_2CH_2SEt$ | $CH_2C(O)NHCH(Me)CF_3$ |
| $CH_2C(O)N(H)CH_2CH_2F$ | $CH_2CH_2S(n\text{-}Pr)$ | $CH_2C(O)NHCH_2CH(Me)CF_3$ |
| $CH(Me)C(O)N(H)CH_2CH_2F$ | $CH_2CH_2CH_2SEt$ | $CH(Me)C(O)NHCH_2CHF_2$ |
| $CH_2CF_3$ | $CH_2CH_2S(O)Et$ | $CH(Me)C(O)NHCH_2CH_2CF_3$ |
| $CH_2$-(2-Py) | $CH_2CH_2S(O)(n\text{-}Pr)$ | $CH(Me)C(O)NHCH(Me)CF_3$ |
| $CH_2$-(4-Thz) | $CH_2CH_2CH_2S(O)Et$ | $CH(Me)C(O)NHCH_2CH(Me)CF_3$ |
| | $R^{2a}$ is $OCH_2CF_3$, $R^{2b}$ is H, $R^{2c}$ is F | |
| $CH_2CH_3$ | $CH_2$-c-Pr | $CH_2CH_2SO_2Et$ |
| $CH_2$-i-Pr | $CH_2CH_2SMe$ | $CH_2CH_2SO_2(n\text{-}Pr)$ |
| $CH_2CH_2Cl$ | $CH(Me)CH_2SMe$ | $CH_2CH_2CH_2SO_2Et$ |
| $CH_2CH_2OH$ | $CH_2CH_2CH_2SMe$ | $CH_2C(O)NH(Me)$ |
| $CH(Me)CH_2OH$ | $CH_2CH_2S(O)Me$ | $CH_2C(O)NH(n\text{-}Pr)$ |
| $CH_2CH(Me)OH$ | $CH(Me)CH_2S(O)Me$ | $CH_2C(O)NH(s\text{-}Bu)$ |
| $CH_2C(Me)_2OH$ | $CH_2CH_2CH_2S(O)Me$ | $CH_2C(O)NMe_2$ |
| $CH_2CH_2CH_2OH$ | $CH_2CH_2SO_2Me$ | $CH_2C(O)NMe(Et)$ |
| $CH_2C(Me)_2CH_2OH$ | $CH(Me)CH_2SO_2Me$ | $CH(Me)C(O)NH(Me)$ |
| $CH_2CH_2CH(Me)OH$ | $CH_2CH_2CH_2SO_2Me$ | $CH(Me)C(O)NH(Et)$ |
| $CH_2C(O)N(H)Et$ | $CH_2C(O)N(H)CH_2CF_3$ | $CH(Me)C(O)NH(n\text{-}Pr)$ |
| $CH_2C(O)N(H)\text{-}i\text{-}Pr$ | $CH(Me)C(O)N(H)CH_2CF_3$ | $CH(Me)C(O)NH(i\text{-}Pr)$ |

TABLE 2-continued

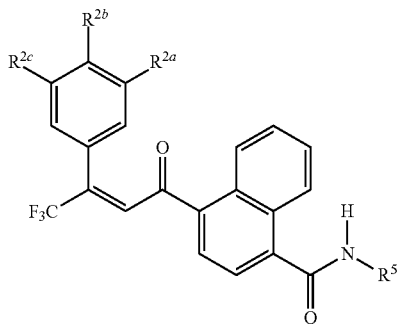

| R⁵ | R⁵ | R⁵ |
|---|---|---|
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |
| CH₂C(O)N(H)CH₂CH₂Cl | | CH₂C(O)NHCH₂CH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |

R²ᵃ is OCH₂CF₃, R²ᵇ is H, R²ᶜ is Cl

| CH₂CH₃ | CH₂-c-Pr | CH₂CH₂SO₂Et |
| CH₂-i-Pr | CH₂CH₂SMe | CH₂CH₂SO₂(n-Pr) |
| CH₂CH₂Cl | CH(Me)CH₂SMe | CH₂CH₂CH₂SO₂Et |
| CH₂CH₂OH | CH₂CH₂CH₂SMe | CH₂C(O)NH(Me) |
| CH(Me)CH₂OH | CH₂CH₂S(O)Me | CH₂C(O)NH(n-Pr) |
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |
| CH₂C(O)N(H)CH₂CH₂Cl | | CH₂C(O)NHCH₂CH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |

R²ᵃ is OCH₂CF₃, R²ᵇ is H, R²ᶜ is Br

| CH₂CH₃ | CH₂-c-Pr | CH₂CH₂SO₂Et |
| CH₂-i-Pr | CH₂CH₂SMe | CH₂CH₂SO₂(n-Pr) |
| CH₂CH₂Cl | CH(Me)CH₂SMe | CH₂CH₂CH₂SO₂Et |
| CH₂CH₂OH | CH₂CH₂CH₂SMe | CH₂C(O)NH(Me) |
| CH(Me)CH₂OH | CH₂CH₂S(O)Me | CH₂C(O)NH(n-Pr) |
| CH₂CH(Me)OH | CH(Me)CH₂S(O)Me | CH₂C(O)NH(s-Bu) |
| CH₂C(Me)₂OH | CH₂CH₂CH₂S(O)Me | CH₂C(O)NMe₂ |
| CH₂CH₂CH₂OH | CH₂CH₂SO₂Me | CH₂C(O)NMe(Et) |
| CH₂C(Me)₂CH₂OH | CH(Me)CH₂SO₂Me | CH(Me)C(O)NH(Me) |
| CH₂CH₂CH(Me)OH | CH₂CH₂CH₂SO₂Me | CH(Me)C(O)NH(Et) |
| CH₂C(O)N(H)Et | CH₂C(O)N(H)CH₂CF₃ | CH(Me)C(O)NH(n-Pr) |
| CH₂C(O)N(H)-i-Pr | CH(Me)C(O)N(H)CH₂CF₃ | CH(Me)C(O)NH(i-Pr) |
| CH₂C(O)N(H)CH₂-i-Pr | CH₂C(O)N(H)CH₂CH₂SMe | CH(Me)C(O)NH(s-Bu) |
| CH(Me)C(O)N(H)CH₂-i-Pr | CH₂C(O)N(H)CH₂CH₂SO₂Me | CH₂C(O)NHCH₂CHF₂ |
| CH₂C(O)N(H)CH₂CH₂Cl | | CH₂C(O)NHCH₂CH₂CF₃ |
| CH(Me)C(O)N(H)CH₂CH₂Cl | CH₂CH₂SEt | CH₂C(O)NHCH(Me)CF₃ |
| CH₂C(O)N(H)CH₂CH₂F | CH₂CH₂S(n-Pr) | CH₂C(O)NHCH₂CH(Me)CF₃ |
| CH(Me)C(O)N(H)CH₂CH₂F | CH₂CH₂CH₂SEt | CH(Me)C(O)NHCH₂CHF₂ |
| CH₂CF₃ | CH₂CH₂S(O)Et | CH(Me)C(O)NHCH₂CH₂CF₃ |
| CH₂-(2-Py) | CH₂CH₂S(O)(n-Pr) | CH(Me)C(O)NHCH(Me)CF₃ |
| CH₂-(4-Thz) | CH₂CH₂CH₂S(O)Et | CH(Me)C(O)NHCH₂CH(Me)CF₃ |

TABLE 3

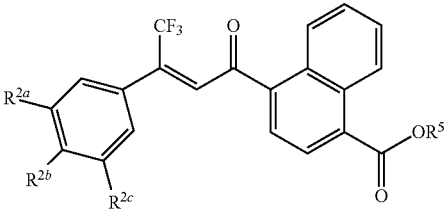

| $R^{2a}$ | $R^{2b}$ | $R^{2c}$ | $R^5$ | $R^{2a}$ | $R^{2b}$ | $R^{2c}$ | $R^5$ |
|---|---|---|---|---|---|---|---|
| Cl | H | Cl | CH₃ | CF₃ | H | Cl | CH₃ |
| Cl | H | Cl | CH₂CH₃ | CF₃ | H | Cl | CH₂CH₃ |
| Cl | H | Cl | CH₂-i-Pr | CF₃ | H | Cl | CH₂-i-Pr |
| Cl | H | Cl | n-Pr | CF₃ | H | Cl | n-Pr |
| Cl | H | Cl | i-Pr | CF₃ | H | Cl | i-Pr |
| Cl | H | Cl | s-Bu | CF₃ | H | Cl | s-Bu |
| Cl | H | Cl | t-Bu | CF₃ | H | Cl | t-Bu |
| Cl | H | Cl | (CH₂)₅CH₃ | CF₃ | H | Cl | (CH₂)₅CH₃ |
| Cl | H | Cl | CH₂Ph | CF₃ | H | Cl | CH₂Ph |
| Br | H | Br | CH₃ | CF₃ | H | CF₃ | CH₃ |
| Br | H | Br | CH₂CH₃ | CF₃ | H | CF₃ | CH₂CH₃ |
| Br | H | Br | CH₂-i-Pr | CF₃ | H | CF₃ | CH₂-i-Pr |
| Br | H | Br | n-Pr | CF₃ | H | CF₃ | n-Pr |
| Br | H | Br | i-Pr | CF₃ | H | CF₃ | i-Pr |
| Br | H | Br | s-Bu | CF₃ | H | CF₃ | s-Bu |
| Br | H | Br | t-Bu | CF₃ | H | CF₃ | t-Bu |
| Br | H | Br | (CH₂)₅CH₃ | CF₃ | H | CF₃ | (CH₂)₅CH₃ |
| Br | H | Br | CH₂Ph | CF₃ | H | CF₃ | CH₂Ph |
| CF₃ | H | H | CH₃ | Cl | Cl | Cl | CH₃ |
| CF₃ | H | H | CH₂CH₃ | Cl | Cl | Cl | CH₂CH₃ |
| CF₃ | H | H | CH₂-i-Pr | Cl | Cl | Cl | CH₂-i-Pr |
| CF₃ | H | H | n-Pr | Cl | Cl | Cl | n-Pr |
| CF₃ | H | H | i-Pr | Cl | Cl | Cl | i-Pr |
| CF₃ | H | H | s-Bu | Cl | Cl | Cl | s-Bu |
| CF₃ | H | H | t-Bu | Cl | Cl | Cl | t-Bu |
| CF₃ | H | H | (CH₂)₅CH₃ | Cl | Cl | Cl | (CH₂)₅CH₃ |
| CF₃ | H | H | CH₂Ph | Cl | Cl | Cl | CH₂Ph |
| CF₃ | H | F | CH₃ | Cl | F | Cl | CH₃ |
| CF₃ | H | F | CH₂CH₃ | Cl | F | Cl | CH₂CH₃ |
| CF₃ | H | F | CH₂-i-Pr | Cl | F | Cl | CH₂-i-Pr |
| CF₃ | H | F | n-Pr | Cl | F | Cl | n-Pr |
| CF₃ | H | F | i-Pr | Cl | F | Cl | i-Pr |
| CF₃ | H | F | s-Bu | Cl | F | Cl | s-Bu |
| CF₃ | H | F | t-Bu | Cl | F | Cl | t-Bu |
| CF₃ | H | F | (CH₂)₅CH₃ | Cl | F | Cl | (CH₂)₅CH₃ |
| CF₃ | H | F | CH₂Ph | Cl | F | Cl | CH₂Ph |
| CF₃ | H | Br | CH₃ | OCF₃ | H | Cl | CH₃ |
| CF₃ | H | Br | CH₂CH₃ | OCF₃ | H | Cl | CH₂CH₃ |
| CF₃ | H | Br | CH₂-i-Pr | OCF₃ | H | Cl | CH₂-i-Pr |
| CF₃ | H | Br | n-Pr | OCF₃ | H | Cl | n-Pr |
| CF₃ | H | Br | i-Pr | OCF₃ | H | Cl | i-Pr |
| CF₃ | H | Br | s-Bu | OCF₃ | H | Cl | s-Bu |
| CF₃ | H | Br | t-Bu | OCF₃ | H | Cl | t-Bu |
| CF₃ | H | Br | (CH₂)₅CH₃ | OCF₃ | H | Cl | (CH₂)₅CH₃ |
| CF₃ | H | Br | CH₂Ph | OCF₃ | H | Cl | CH₂Ph |
| OCH₂CF₃ | H | F | CH₃ | OCH₂CF₃ | H | Cl | CH₃ |
| OCH₂CF₃ | H | F | CH₂CH₃ | OCH₂CF₃ | H | Cl | CH₂CH₃ |
| OCH₂CF₃ | H | F | CH₂-i-Pr | OCH₂CF₃ | H | Cl | CH₂-i-Pr |
| OCH₂CF₃ | H | F | n-Pr | OCH₂CF₃ | H | Cl | n-Pr |
| OCH₂CF₃ | H | F | i-Pr | OCH₂CF₃ | H | Cl | i-Pr |
| OCH₂CF₃ | H | F | s-Bu | OCH₂CF₃ | H | Cl | s-Bu |
| OCH₂CF₃ | H | F | t-Bu | OCH₂CF₃ | H | Cl | t-Bu |
| OCH₂CF₃ | H | F | (CH₂)₅CH₃ | OCH₂CF₃ | H | Cl | (CH₂)₅CH₃ |
| OCH₂CF₃ | H | F | CH₂Ph | OCH₂CF₃ | H | Cl | CH₂Ph |
| OCH₂CF₃ | H | Br | CH₃ | OCH₂CF₃ | H | Br | s-Bu |
| OCH₂CF₃ | H | Br | CH₂CH₃ | OCH₂CF₃ | H | Br | t-Bu |
| OCH₂CF₃ | H | Br | CH₂-i-Pr | OCH₂CF₃ | H | Br | (CH₂)₅CH₃ |
| OCH₂CF₃ | H | Br | n-Pr | OCH₂CF₃ | H | Br | CH₂Ph |
| OCH₂CF₃ | H | Br | i-Pr | | | | |

TABLE 4

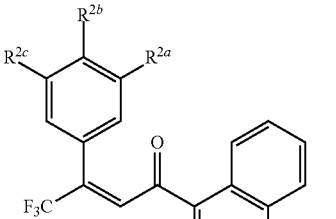

| $R^{2a}$ | $R^{2b}$ | $R^{2c}$ | $R^5$ | $R^{2a}$ | $R^{2b}$ | $R^{2c}$ | $R^5$ |
|---|---|---|---|---|---|---|---|
| Cl | H | Cl | CH₃ | CF₃ | H | Cl | CH₃ |
| Cl | H | Cl | CH₂CH₃ | CF₃ | H | Cl | CH₂CH₃ |
| Cl | H | Cl | CH₂-i-Pr | CF₃ | H | Cl | CH₂-i-Pr |
| Cl | H | Cl | n-Pr | CF₃ | H | Cl | n-Pr |
| Cl | H | Cl | i-Pr | CF₃ | H | Cl | i-Pr |
| Cl | H | Cl | s-Bu | CF₃ | H | Cl | s-Bu |
| Cl | H | Cl | t-Bu | CF₃ | H | Cl | t-Bu |
| Cl | H | Cl | (CH₂)₅CH₃ | CF₃ | H | Cl | (CH₂)₅CH₃ |
| Cl | H | Cl | CH₂Ph | CF₃ | H | Cl | CH₂Ph |
| Br | H | Br | CH₃ | CF₃ | H | CF₃ | CH₃ |
| Br | H | Br | CH₂CH₃ | CF₃ | H | CF₃ | CH₂CH₃ |
| Br | H | Br | CH₂-i-Pr | CF₃ | H | CF₃ | CH₂-i-Pr |
| Br | H | Br | n-Pr | CF₃ | H | CF₃ | n-Pr |
| Br | H | Br | i-Pr | CF₃ | H | CF₃ | i-Pr |
| Br | H | Br | s-Bu | CF₃ | H | CF₃ | s-Bu |
| Br | H | Br | t-Bu | CF₃ | H | CF₃ | t-Bu |
| Br | H | Br | (CH₂)₅CH₃ | CF₃ | H | CF₃ | (CH₂)₅CH₃ |
| Br | H | Br | CH₂Ph | CF₃ | H | CF₃ | CH₂Ph |
| CF₃ | H | H | CH₃ | Cl | Cl | Cl | CH₃ |
| CF₃ | H | H | CH₂CH₃ | Cl | Cl | Cl | CH₂CH₃ |
| CF₃ | H | H | CH₂-i-Pr | Cl | Cl | Cl | CH₂-i-Pr |
| CF₃ | H | H | n-Pr | Cl | Cl | Cl | n-Pr |
| CF₃ | H | H | i-Pr | Cl | Cl | Cl | i-Pr |
| CF₃ | H | H | s-Bu | Cl | Cl | Cl | s-Bu |
| CF₃ | H | H | t-Bu | Cl | Cl | Cl | t-Bu |
| CF₃ | H | H | (CH₂)₅CH₃ | Cl | Cl | Cl | (CH₂)₅CH₃ |
| CF₃ | H | H | CH₂Ph | Cl | Cl | Cl | CH₂Ph |
| CF₃ | H | F | CH₃ | Cl | F | Cl | CH₃ |
| CF₃ | H | F | CH₂CH₃ | Cl | F | Cl | CH₂CH₃ |
| CF₃ | H | F | CH₂-i-Pr | Cl | F | Cl | CH₂-i-Pr |
| CF₃ | H | F | n-Pr | Cl | F | Cl | n-Pr |
| CF₃ | H | F | i-Pr | Cl | F | Cl | i-Pr |
| CF₃ | H | F | s-Bu | Cl | F | Cl | s-Bu |
| CF₃ | H | F | t-Bu | Cl | F | Cl | t-Bu |
| CF₃ | H | F | (CH₂)₅CH₃ | Cl | F | Cl | (CH₂)₅CH₃ |
| CF₃ | H | F | CH₂Ph | Cl | F | Cl | CH₂Ph |
| CF₃ | H | Br | CH₃ | OCF₃ | H | Cl | CH₃ |
| CF₃ | H | Br | CH₂CH₃ | OCF₃ | H | Cl | CH₂CH₃ |
| CF₃ | H | Br | CH₂-i-Pr | OCF₃ | H | Cl | CH₂-i-Pr |
| CF₃ | H | Br | n-Pr | OCF₃ | H | Cl | n-Pr |
| CF₃ | H | Br | i-Pr | OCF₃ | H | Cl | i-Pr |
| CF₃ | H | Br | s-Bu | OCF₃ | H | Cl | s-Bu |
| CF₃ | H | Br | t-Bu | OCF₃ | H | Cl | t-Bu |
| CF₃ | H | Br | (CH₂)₅CH₃ | OCF₃ | H | Cl | (CH₂)₅CH₃ |
| CF₃ | H | Br | CH₂Ph | OCF₃ | H | Cl | CH₂Ph |
| OCH₂CF₃ | H | F | CH₃ | OCH₂CF₃ | H | Cl | CH₃ |
| OCH₂CF₃ | H | F | CH₂CH₃ | OCH₂CF₃ | H | Cl | CH₂CH₃ |
| OCH₂CF₃ | H | F | CH₂-i-Pr | OCH₂CF₃ | H | Cl | CH₂-i-Pr |
| OCH₂CF₃ | H | F | n-Pr | OCH₂CF₃ | H | Cl | n-Pr |
| OCH₂CF₃ | H | F | i-Pr | OCH₂CF₃ | H | Cl | i-Pr |
| OCH₂CF₃ | H | F | s-Bu | OCH₂CF₃ | H | Cl | s-Bu |
| OCH₂CF₃ | H | F | t-Bu | OCH₂CF₃ | H | Cl | t-Bu |
| OCH₂CF₃ | H | F | (CH₂)₅CH₃ | OCH₂CF₃ | H | Cl | (CH₂)₅CH₃ |
| OCH₂CF₃ | H | F | CH₂Ph | OCH₂CF₃ | H | Cl | CH₂Ph |
| OCH₂CF₃ | H | Br | CH₃ | OCH₂CF₃ | H | Br | s-Bu |
| OCH₂CF₃ | H | Br | CH₂CH₃ | OCH₂CF₃ | H | Br | t-Bu |
| OCH₂CF₃ | H | Br | CH₂-i-Pr | OCH₂CF₃ | H | Br | (CH₂)₅CH₃ |
| OCH₂CF₃ | H | Br | n-Pr | OCH₂CF₃ | H | Br | CH₂Ph |
| OCH₂CF₃ | H | Br | i-Pr | | | | |

TABLE 5

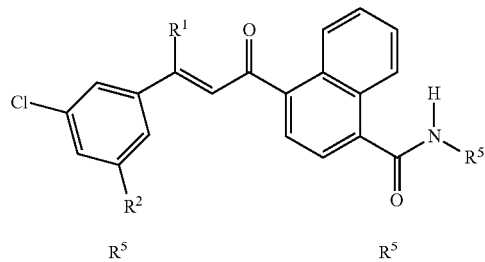

| R⁵ | R⁵ |
|---|---|
| R¹ is CF₂Cl, R² is Cl | |
| CH₂CH₃ | CH₂C(O)N(H)CH₂CF₃ |
| CH₂-i-Pr | CH(Me)C(O)N(H)CH₂CF₃ |
| CH₂CH₂Cl | CH₂C(O)N(H)CH₂CH₂SMe |
| CH₂CH₂OH | CH₂C(O)N(H)CH₂CH₂SO₂Me |
| CH(Me)CH₂OH | CH₂CH₂SEt |
| CH₂CH(Me)OH | CH₂CH₂S(n-Pr) |
| CH₂C(Me)₂OH | CH₂CH₂CH₂SEt |
| CH₂CH₂CH₂OH | CH₂CH₂S(O)Et |
| CH₂C(Me)₂CH₂OH | CH₂CH₂S(O)(n-Pr) |
| CH₂CH₂CH(Me)OH | CH₂CH₂CH₂S(O)Et |
| CH₂C(O)N(H)Et | CH₂CH₂SO₂Et |
| CH₂C(O)N(H)-i-Pr | CH₂CH₂SO₂(n-Pr) |
| CH₂C(O)N(H)CH₂-i-Pr | CH₂CH₂CH₂SO₂Et |
| CH(Me)C(O)N(H)CH₂-i-Pr | CH₂C(O)NH(Me) |
| CH₂C(O)N(H)CH₂CH₂Cl | CH₂C(O)NH(n-Pr) |
| CH(Me)C(O)N(H)CH₂CH₂Cl | CH₂C(O)NH(s-Bu) |
| CH₂C(O)N(H)CH₂CH₂F | CH₂C(O)NMe₂ |
| CH(Me)C(O)N(H)CH₂CH₂F | CH₂C(O)NMe(Et) |
| CH₂CF₃ | CH(Me)C(O)NH(Me) |
| CH₂-(2-Py) | CH(Me)C(O)NH(Et) |
| CH₂-(4-Thz) | CH(Me)C(O)NH(n-Pr) |
| CH₂-c-Pr | CH(Me)C(O)NH(i-Pr) |
| CH₂CH₂SMe | CH(Me)C(O)NH(s-Bu) |
| CH(Me)CH₂SMe | CH₂C(O)NHCH₂CHF₂ |
| CH₂CH₂CH₂SMe | CH₂C(O)NHCH₂CH₂CF₃ |
| CH₂CH₂S(O)Me | CH₂C(O)NHCH(Me)CF₃ |
| CH(Me)CH₂S(O)Me | CH₂C(O)NHCH₂CH(Me)CF₃ |
| CH₂CH₂CH₂S(O)Me | CH(Me)C(O)NHCH₂CHF₂ |
| CH₂CH₂SO₂Me | CH(Me)C(O)NHCH₂CH₂CF₃ |
| CH(Me)CH₂SO₂Me | CH(Me)C(O)NHCH(Me)CF₃ |
| CH₂CH₂CH₂SO₂Me | CH(Me)C(O)NHCH₂CH(Me)CF₃ |
| R¹ is CF₂CF₂H, R² is Cl | |
| CH₂CH₃ | CH₂C(O)N(H)CH₂CF₃ |
| CH₂-i-Pr | CH(Me)C(O)N(H)CH₂CF₃ |
| CH₂CH₂Cl | CH₂C(O)N(H)CH₂CH₂SMe |
| CH₂CH₂OH | CH₂C(O)N(H)CH₂CH₂SO₂Me |
| CH(Me)CH₂OH | CH₂CH₂SEt |
| CH₂CH(Me)OH | CH₂CH₂S(n-Pr) |
| CH₂C(Me)₂OH | CH₂CH₂CH₂SEt |
| CH₂CH₂CH₂OH | CH₂CH₂S(O)Et |
| CH₂C(Me)₂CH₂OH | CH₂CH₂S(O)(n-Pr) |
| CH₂CH₂CH(Me)OH | CH₂CH₂CH₂S(O)Et |
| CH₂C(O)N(H)Et | CH₂CH₂SO₂Et |
| CH₂C(O)N(H)-i-Pr | CH₂CH₂SO₂(n-Pr) |
| CH₂C(O)N(H)CH₂-i-Pr | CH₂CH₂CH₂SO₂Et |
| CH(Me)C(O)N(H)CH₂-i-Pr | CH₂C(O)NH(Me) |
| CH₂C(O)N(H)CH₂CH₂Cl | CH₂C(O)NH(n-Pr) |
| CH(Me)C(O)N(H)CH₂CH₂Cl | CH₂C(O)NH(s-Bu) |
| CH₂C(O)N(H)CH₂CH₂F | CH₂C(O)NMe₂ |
| CH(Me)C(O)N(H)CH₂CH₂F | CH₂C(O)NMe(Et) |
| CH₂CF₃ | CH(Me)C(O)NH(Me) |
| CH₂-(2-Py) | CH(Me)C(O)NH(Et) |
| CH₂-(4-Thz) | CH(Me)C(O)NH(n-Pr) |
| CH₂-c-Pr | CH(Me)C(O)NH(i-Pr) |
| CH₂CH₂SMe | CH(Me)C(O)NH(s-Bu) |
| CH(Me)CH₂SMe | CH₂C(O)NHCH₂CHF₂ |
| CH₂CH₂CH₂SMe | CH₂C(O)NHCH₂CH₂CF₃ |
| CH₂CH₂S(O)Me | CH₂C(O)NHCH(Me)CF₃ |
| CH(Me)CH₂S(O)Me | CH₂C(O)NHCH₂CH(Me)CF₃ |
| CH₂CH₂CH₂S(O)Me | CH(Me)C(O)NHCH₂CHF₂ |
| CH₂CH₂SO₂Me | CH(Me)C(O)NHCH₂CH₂CF₃ |
| CH(Me)CH₂SO₂Me | CH(Me)C(O)NHCH(Me)CF₃ |
| CH₂CH₂CH₂SO₂Me | CH(Me)C(O)NHCH₂CH(Me)CF₃ |

TABLE 5-continued

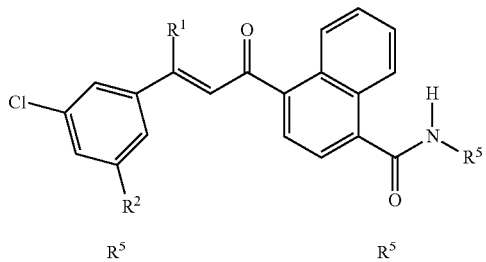

| R⁵ | R⁵ |
|---|---|
| R¹ is CCl₂F, R² is Cl | |
| CH₂CH₃ | CH₂C(O)N(H)CH₂CF₃ |
| CH₂-i-Pr | CH(Me)C(O)N(H)CH₂CF₃ |
| CH₂CH₂Cl | CH₂C(O)N(H)CH₂CH₂SMe |
| CH₂CH₂OH | CH₂C(O)N(H)CH₂CH₂SO₂Me |
| CH(Me)CH₂OH | CH₂CH₂SEt |
| CH₂CH(Me)OH | CH₂CH₂S(n-Pr) |
| CH₂C(Me)₂OH | CH₂CH₂CH₂SEt |
| CH₂CH₂CH₂OH | CH₂CH₂S(O)Et |
| CH₂C(Me)₂CH₂OH | CH₂CH₂S(O)(n-Pr) |
| CH₂CH₂CH(Me)OH | CH₂CH₂CH₂S(O)Et |
| CH₂C(O)N(H)Et | CH₂CH₂SO₂Et |
| CH₂C(O)N(H)-i-Pr | CH₂CH₂SO₂(n-Pr) |
| CH₂C(O)N(H)CH₂-i-Pr | CH₂CH₂CH₂SO₂Et |
| CH(Me)C(O)N(H)CH₂-i-Pr | CH₂C(O)NH(Me) |
| CH₂C(O)N(H)CH₂CH₂Cl | CH₂C(O)NH(n-Pr) |
| CH(Me)C(O)N(H)CH₂CH₂Cl | CH₂C(O)NH(s-Bu) |
| CH₂C(O)N(H)CH₂CH₂F | CH₂C(O)NMe₂ |
| CH(Me)C(O)N(H)CH₂CH₂F | CH₂C(O)NMe(Et) |
| CH₂CF₃ | CH(Me)C(O)NH(Me) |
| CH₂-(2-Py) | CH(Me)C(O)NH(Et) |
| CH₂-(4-Thz) | CH(Me)C(O)NH(n-Pr) |
| CH₂-c-Pr | CH(Me)C(O)NH(i-Pr) |
| CH₂CH₂SMe | CH(Me)C(O)NH(s-Bu) |
| CH(Me)CH₂SMe | CH₂C(O)NHCH₂CHF₂ |
| CH₂CH₂CH₂SMe | CH₂C(O)NHCH₂CH₂CF₃ |
| CH₂CH₂S(O)Me | CH₂C(O)NHCH(Me)CF₃ |
| CH(Me)CH₂S(O)Me | CH₂C(O)NHCH₂CH(Me)CF₃ |
| CH₂CH₂CH₂S(O)Me | CH(Me)C(O)NHCH₂CHF₂ |
| CH₂CH₂SO₂Me | CH(Me)C(O)NHCH₂CH₂CF₃ |
| CH(Me)CH₂SO₂Me | CH(Me)C(O)NHCH(Me)CF₃ |
| CH₂CH₂CH₂SO₂Me | CH(Me)C(O)NHCH₂CH(Me)CF₃ |
| R¹ is CF₂CF₃, R² is Cl | |
| CH₂CH₃ | CH₂C(O)N(H)CH₂CF₃ |
| CH₂-i-Pr | CH(Me)C(O)N(H)CH₂CF₃ |
| CH₂CH₂Cl | CH₂C(O)N(H)CH₂CH₂SMe |
| CH₂CH₂OH | CH₂C(O)N(H)CH₂CH₂SO₂Me |
| CH(Me)CH₂OH | CH₂CH₂SEt |
| CH₂CH(Me)OH | CH₂CH₂S(n-Pr) |
| CH₂C(Me)₂OH | CH₂CH₂CH₂SEt |
| CH₂CH₂CH₂OH | CH₂CH₂S(O)Et |
| CH₂C(Me)₂CH₂OH | CH₂CH₂S(O)(n-Pr) |
| CH₂CH₂CH(Me)OH | CH₂CH₂CH₂S(O)Et |
| CH₂C(O)N(H)Et | CH₂CH₂SO₂Et |
| CH₂C(O)N(H)-i-Pr | CH₂CH₂SO₂(n-Pr) |
| CH₂C(O)N(H)CH₂-i-Pr | CH₂CH₂CH₂SO₂Et |
| CH(Me)C(O)N(H)CH₂-i-Pr | CH₂C(O)NH(Me) |
| CH₂C(O)N(H)CH₂CH₂Cl | CH₂C(O)NH(n-Pr) |
| CH(Me)C(O)N(H)CH₂CH₂Cl | CH₂C(O)NH(s-Bu) |
| CH₂C(O)N(H)CH₂CH₂F | CH₂C(O)NMe₂ |
| CH(Me)C(O)N(H)CH₂CH₂F | CH₂C(O)NMe(Et) |
| CH₂CF₃ | CH(Me)C(O)NH(Me) |
| CH₂-(2-Py) | CH(Me)C(O)NH(Et) |
| CH₂-(4-Thz) | CH(Me)C(O)NH(n-Pr) |
| CH₂-c-Pr | CH(Me)C(O)NH(i-Pr) |
| CH₂CH₂SMe | CH(Me)C(O)NH(s-Bu) |
| CH(Me)CH₂SMe | CH₂C(O)NHCH₂CHF₂ |
| CH₂CH₂CH₂SMe | CH₂C(O)NHCH₂CH₂CF₃ |
| CH₂CH₂S(O)Me | CH₂C(O)NHCH(Me)CF₃ |
| CH(Me)CH₂S(O)Me | CH₂C(O)NHCH₂CH(Me)CF₃ |
| CH₂CH₂CH₂S(O)Me | CH(Me)C(O)NHCH₂CHF₂ |
| CH₂CH₂SO₂Me | CH(Me)C(O)NHCH₂CH₂CF₃ |
| CH(Me)CH₂SO₂Me | CH(Me)C(O)NHCH(Me)CF₃ |
| CH₂CH₂CH₂SO₂Me | CH(Me)C(O)NHCH₂CH(Me)CF₃ |

TABLE 6

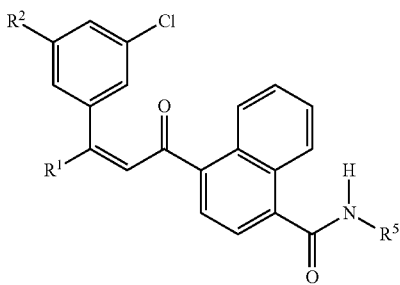

| R⁵ | R⁵ |
|---|---|
| R¹ is CF₂Cl, R² is Cl | |
| CH₂CH₃ | CH₂C(O)N(H)CH₂CF₃ |
| CH₂-i-Pr | CH(Me)C(O)N(H)CH₂CF₃ |
| CH₂CH₂Cl | CH₂C(O)N(H)CH₂CH₂SMe |
| CH₂CH₂OH | CH₂C(O)N(H)CH₂CH₂SO₂Me |
| CH(Me)CH₂OH | CH₂CH₂SEt |
| CH₂CH(Me)OH | CH₂CH₂S(n-Pr) |
| CH₂C(Me)₂OH | CH₂CH₂CH₂SEt |
| CH₂CH₂CH₂OH | CH₂CH₂S(O)Et |
| CH₂C(Me)₂CH₂OH | CH₂CH₂S(O)(n-Pr) |
| CH₂CH₂CH(Me)OH | CH₂CH₂CH₂S(O)Et |
| CH₂C(O)N(H)Et | CH₂CH₂SO₂Et |
| CH₂C(O)N(H)CH₂-i-Pr | CH₂CH₂SO₂(n-Pr) |
| CH(Me)C(O)N(H)CH₂-i-Pr | CH₂CH₂CH₂SO₂Et |
| CH₂C(O)N(H)CH₂CH₂Cl | CH₂C(O)NH(Me) |
| CH(Me)C(O)N(H)CH₂CH₂Cl | CH₂C(O)NH(n-Pr) |
| CH₂C(O)N(H)CH₂CH₂F | CH₂C(O)NH(s-Bu) |
| CH(Me)C(O)N(H)CH₂CH₂F | CH₂C(O)NMe₂ |
| CH₂CF₃ | CH₂C(O)NMe(Et) |
| CH₂-(2-Py) | CH(Me)C(O)NH(Me) |
| CH₂-(4-Thz) | CH(Me)C(O)NH(Et) |
| CH₂-c-Pr | CH(Me)C(O)NH(n-Pr) |
| CH₂CH₂SMe | CH(Me)C(O)NH(i-Pr) |
| CH(Me)CH₂SMe | CH(Me)C(O)NH(s-Bu) |
| CH₂CH₂CH₂SMe | CH₂C(O)NHCH₂CHF₂ |
| CH₂CH₂S(O)Me | CH₂C(O)NHCH₂CH₂CF₃ |
| CH(Me)CH₂S(O)Me | CH₂C(O)NHCH₂CH(Me)CF₃ |
| CH₂CH₂CH₂S(O)Me | CH(Me)C(O)NHCH₂CHF₂ |
| CH₂CH₂SO₂Me | CH(Me)C(O)NHCH₂CH₂CF₃ |
| CH(Me)CH₂SO₂Me | CH(Me)C(O)NHCH₂CF₃ |
| CH₂CH₂CH₂SO₂Me | CH(Me)C(O)NHCH₂CH(Me)CF₃ |
| R¹ is CF₂CF₂H, R² is Cl | |
| CH₂CH₃ | CH₂C(O)N(H)CH₂CF₃ |
| CH₂-i-Pr | CH(Me)C(O)N(H)CH₂CF₃ |
| CH₂CH₂Cl | CH₂C(O)N(H)CH₂CH₂SMe |
| CH₂CH₂OH | CH₂C(O)N(H)CH₂CH₂SO₂Me |
| CH(Me)CH₂OH | CH₂CH₂SEt |
| CH₂CH(Me)OH | CH₂CH₂S(n-Pr) |
| CH₂C(Me)₂OH | CH₂CH₂CH₂SEt |
| CH₂CH₂CH₂OH | CH₂CH₂S(O)Et |
| CH₂C(Me)₂CH₂OH | CH₂CH₂S(O)(n-Pr) |
| CH₂CH₂CH(Me)OH | CH₂CH₂CH₂S(O)Et |
| CH₂C(O)N(H)Et | CH₂CH₂SO₂Et |
| CH₂C(O)N(H)CH₂-i-Pr | CH₂CH₂SO₂(n-Pr) |
| CH(Me)C(O)N(H)CH₂-i-Pr | CH₂CH₂CH₂SO₂Et |
| CH₂C(O)N(H)CH₂CH₂Cl | CH₂C(O)NH(Me) |
| CH(Me)C(O)N(H)CH₂CH₂Cl | CH₂C(O)NH(n-Pr) |
| CH₂C(O)N(H)CH₂CH₂F | CH₂C(O)NH(s-Bu) |
| CH(Me)C(O)N(H)CH₂CH₂F | CH₂C(O)NMe₂ |
| CH₂CF₃ | CH₂C(O)NMe(Et) |
| CH₂-(2-Py) | CH(Me)C(O)NH(Me) |
| CH₂-(4-Thz) | CH(Me)C(O)NH(Et) |
| CH₂-c-Pr | CH(Me)C(O)NH(n-Pr) |
| CH₂CH₂SMe | CH(Me)C(O)NH(i-Pr) |
| CH(Me)CH₂SMe | CH(Me)C(O)NH(s-Bu) |
| CH₂CH₂CH₂SMe | CH₂C(O)NHCH₂CHF₂ |
| CH₂CH₂S(O)Me | CH₂C(O)NHCH₂CH(Me)CF₃ |
| CH(Me)CH₂S(O)Me | CH₂C(O)NHCH₂CH₂CF₃ |
| CH₂CH₂CH₂S(O)Me | CH(Me)C(O)NHCH₂CHF₂ |
| CH₂CH₂SO₂Me | CH(Me)C(O)NHCH₂CH₂CF₃ |

TABLE 6-continued

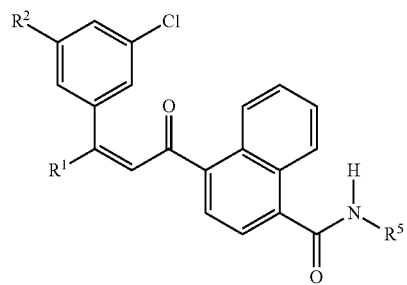

| R⁵ | R⁵ |
|---|---|
| CH(Me)CH₂SO₂Me | CH(Me)C(O)NHCH(Me)CF₃ |
| CH₂CH₂CH₂SO₂Me | CH(Me)C(O)NHCH₂CH(Me)CF₃ |
| R¹ is CCl₂F, R² Cl | |
| CH₂CH₃ | CH₂C(O)N(H)CH₂CF₃ |
| CH₂-i-Pr | CH(Me)C(O)N(H)CH₂CF₃ |
| CH₂CH₂Cl | CH₂C(O)N(H)CH₂CH₂SMe |
| CH₂CH₂OH | CH₂C(O)N(H)CH₂CH₂SO₂Me |
| CH(Me)CH₂OH | CH₂CH₂SEt |
| CH₂CH(Me)OH | CH₂CH₂S(n-Pr) |
| CH₂C(Me)₂OH | CH₂CH₂CH₂SEt |
| CH₂CH₂CH₂OH | CH₂CH₂S(O)Et |
| CH₂C(Me)₂CH₂OH | CH₂CH₂S(O)(n-Pr) |
| CH₂CH₂CH(Me)OH | CH₂CH₂CH₂S(O)Et |
| CH₂C(O)N(H)Et | CH₂CH₂SO₂Et |
| CH₂C(O)N(H)CH₂-i-Pr | CH₂CH₂SO₂(n-Pr) |
| CH(Me)C(O)N(H)CH₂-i-Pr | CH₂CH₂CH₂SO₂Et |
| CH₂C(O)N(H)CH₂CH₂Cl | CH₂C(O)NH(Me) |
| CH(Me)C(O)N(H)CH₂CH₂Cl | CH₂C(O)NH(n-Pr) |
| CH₂C(O)N(H)CH₂CH₂F | CH₂C(O)NH(s-Bu) |
| CH(Me)C(O)N(H)CH₂CH₂F | CH₂C(O)NMe₂ |
| CH₂CF₃ | CH₂C(O)NMe(Et) |
| CH₂-(2-Py) | CH(Me)C(O)NH(Me) |
| CH₂-(4-Thz) | CH(Me)C(O)NH(Et) |
| CH₂-c-Pr | CH(Me)C(O)NH(n-Pr) |
| CH₂CH₂SMe | CH(Me)C(O)NH(i-Pr) |
| CH(Me)CH₂SMe | CH(Me)C(O)NH(s-Bu) |
| CH₂CH₂CH₂SMe | CH₂C(O)NHCH₂CHF₂ |
| CH₂CH₂S(O)Me | CH₂C(O)NHCH₂CH₂CF₃ |
| CH(Me)CH₂S(O)Me | CH₂C(O)NHCH₂CH(Me)CF₃ |
| CH₂CH₂CH₂S(O)Me | CH(Me)C(O)NHCH₂CHF₂ |
| CH₂CH₂SO₂Me | CH(Me)C(O)NHCH₂CH₂CF₃ |
| CH(Me)CH₂SO₂Me | CH(Me)C(O)NHCH(Me)CF₃ |
| CH₂CH₂CH₂SO₂Me | CH(Me)C(O)NHCH₂CH(Me)CF₃ |
| R¹ is CF₂CF₃, R² is Cl | |
| CH₂CH₃ | CH₂C(O)N(H)CH₂CF₃ |
| CH₂-i-Pr | CH(Me)C(O)N(H)CH₂CF₃ |
| CH₂CH₂Cl | CH₂C(O)N(H)CH₂CH₂SMe |
| CH₂CH₂OH | CH₂C(O)N(H)CH₂CH₂SO₂Me |
| CH(Me)CH₂OH | CH₂CH₂SEt |
| CH₂CH(Me)OH | CH₂CH₂S(n-Pr) |
| CH₂C(Me)₂OH | CH₂CH₂CH₂SEt |
| CH₂CH₂CH₂OH | CH₂CH₂S(O)Et |
| CH₂C(Me)₂CH₂OH | CH₂CH₂S(O)(n-Pr) |
| CH₂CH₂CH(Me)OH | CH₂CH₂CH₂S(O)Et |
| CH₂C(O)N(H)Et | CH₂CH₂SO₂Et |
| CH₂C(O)N(H)CH₂-i-Pr | CH₂CH₂SO₂(n-Pr) |
| CH(Me)C(O)N(H)CH₂-i-Pr | CH₂CH₂CH₂SO₂Et |
| CH₂C(O)N(H)CH₂CH₂Cl | CH₂C(O)NH(Me) |
| CH(Me)C(O)N(H)CH₂CH₂Cl | CH₂C(O)NH(n-Pr) |
| CH₂C(O)N(H)CH₂CH₂F | CH₂C(O)NH(s-Bu) |
| CH(Me)C(O)N(H)CH₂CH₂F | CH₂C(O)NMe₂ |
| CH₂CF₃ | CH₂C(O)NMe(Et) |
| CH₂-(2-Py) | CH(Me)C(O)NH(Me) |
| CH₂-(4-Thz) | CH(Me)C(O)NH(Et) |
| CH₂-c-Pr | CH(Me)C(O)NH(n-Pr) |
| CH₂CH₂SMe | CH(Me)C(O)NH(i-Pr) |
| CH(Me)CH₂SMe | CH(Me)C(O)NH(s-Bu) |
| CH₂CH₂CH₂SMe | CH₂C(O)NHCH₂CHF₂ |
| CH₂CH₂S(O)Me | CH₂C(O)NHCH₂CH₂CF₃ |
| CH(Me)CH₂S(O)Me | CH₂C(O)NHCH(Me)CF₃ |

TABLE 6-continued

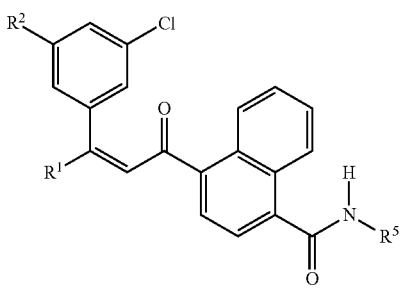

| R[5] | R[5] |
|---|---|
| CH$_2$CH$_2$CH$_2$S(O)Me | CH(Me)C(O)NHCH$_2$CHF$_2$ |
| CH$_2$CH$_2$SO$_2$Me | CH(Me)C(O)NHCH$_2$CH$_2$CF$_3$ |
| CH(Me)CH$_2$SO$_2$Me | CH(Me)C(O)NHCH(Me)CF$_3$ |
| CH$_2$CH$_2$CH$_2$SO$_2$Me | CH(Me)C(O)NHCH$_2$CH(Me)CF$_3$ |

TABLE 7

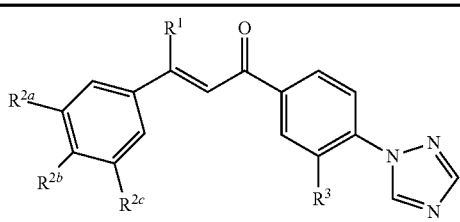

| R$^{2a}$ | R$^{2b}$ | R$^{2c}$ | R[1] | R[3] |
|---|---|---|---|---|
| Cl | H | Cl | CF$_3$ | H |
| Cl | H | Cl | CF$_3$ | Me |
| Cl | H | Cl | CF$_3$ | CN |
| Cl | F | Cl | CF$_3$ | H |
| Cl | F | Cl | CF$_3$ | Me |
| Cl | F | Cl | CF$_3$ | CN |
| CF$_3$ | H | H | CF$_3$ | H |
| CF$_3$ | H | H | CF$_3$ | Me |
| CF$_3$ | H | H | CF$_3$ | CN |
| CF$_3$ | H | Cl | CF$_3$ | H |
| CF$_3$ | H | Cl | CF$_3$ | Me |
| CF$_3$ | H | Cl | CF$_3$ | CN |
| CF$_3$ | H | CF$_3$ | CF$_3$ | H |
| CF$_3$ | H | CF$_3$ | CF$_3$ | Me |
| CF$_3$ | H | CF$_3$ | CF$_3$ | CN |
| Cl | H | Cl | CF$_2$Cl | H |
| Cl | H | Cl | CF$_2$Cl | Me |
| Cl | H | Cl | CF$_2$Cl | CN |
| Cl | H | Cl | CCl$_2$F | H |
| Cl | H | Cl | CCl$_2$F | Me |
| Cl | Cl | Cl | CF$_3$ | H |
| Cl | Cl | Cl | CF$_3$ | Me |
| Cl | Cl | Cl | CF$_3$ | CN |
| Br | H | Br | CF$_3$ | H |
| Br | H | Br | CF$_3$ | Me |
| Br | H | Br | CF$_3$ | CN |
| CF$_3$ | H | F | CF$_3$ | H |
| CF$_3$ | H | F | CF$_3$ | Me |
| CF$_3$ | H | F | CF$_3$ | CN |
| CF$_3$ | H | Br | CF$_3$ | H |
| CF$_3$ | H | Br | CF$_3$ | Me |
| CF$_3$ | H | Br | CF$_3$ | CN |
| Cl | H | Cl | CCl$_2$F | CN |
| Cl | H | Cl | CF$_2$CF$_2$H | H |
| Cl | H | Cl | CF$_2$CF$_2$H | Me |
| Cl | H | Cl | CF$_2$CF$_2$H | CN |
| Cl | H | Cl | CF$_2$CF$_3$ | H |
| Cl | H | Cl | CF$_2$CF$_3$ | Me |
| Cl | H | Cl | CF$_2$CF$_3$ | CN |

TABLE 8

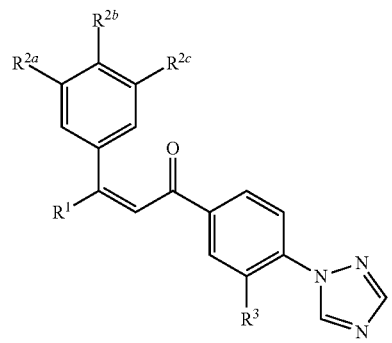

| R$^{2a}$ | R$^{2b}$ | R$^{2c}$ | R[1] | R[3] |
|---|---|---|---|---|
| Cl | H | Cl | CF$_3$ | H |
| Cl | H | Cl | CF$_3$ | Me |
| Cl | H | Cl | CF$_3$ | CN |
| Cl | F | Cl | CF$_3$ | H |
| Cl | F | Cl | CF$_3$ | Me |
| Cl | F | Cl | CF$_3$ | CN |
| CF$_3$ | H | H | CF$_3$ | H |
| CF$_3$ | H | H | CF$_3$ | Me |
| CF$_3$ | H | H | CF$_3$ | CN |
| CF$_3$ | H | Cl | CF$_3$ | H |
| CF$_3$ | H | Cl | CF$_3$ | Me |
| CF$_3$ | H | Cl | CF$_3$ | CN |
| CF$_3$ | H | CF$_3$ | CF$_3$ | H |
| CF$_3$ | H | CF$_3$ | CF$_3$ | Me |
| CF$_3$ | H | CF$_3$ | CF$_3$ | CN |
| Cl | H | Cl | CF$_2$Cl | H |
| Cl | H | Cl | CF$_2$Cl | Me |
| Cl | H | Cl | CF$_2$Cl | CN |
| Cl | H | Cl | CCl$_2$F | H |
| Cl | H | Cl | CCl$_2$F | Me |
| Cl | Cl | Cl | CF$_3$ | H |
| Cl | Cl | Cl | CF$_3$ | Me |
| Cl | Cl | Cl | CF$_3$ | CN |
| Br | H | Br | CF$_3$ | H |
| Br | H | Br | CF$_3$ | Me |
| Br | H | Br | CF$_3$ | CN |
| CF$_3$ | H | F | CF$_3$ | H |
| CF$_3$ | H | F | CF$_3$ | Me |
| CF$_3$ | H | F | CF$_3$ | CN |
| CF$_3$ | H | Br | CF$_3$ | H |
| CF$_3$ | H | Br | CF$_3$ | Me |
| CF$_3$ | H | Br | CF$_3$ | CN |
| Cl | H | Cl | CCl$_2$F | CN |
| Cl | H | Cl | CF$_2$CF$_2$H | H |
| Cl | H | Cl | CF$_2$CF$_2$H | Me |
| Cl | H | Cl | CF$_2$CF$_2$H | CN |
| Cl | H | Cl | CF$_2$CF$_3$ | H |
| Cl | H | Cl | CF$_2$CF$_3$ | Me |
| Cl | H | Cl | CF$_2$CF$_3$ | CN |

TABLE 9

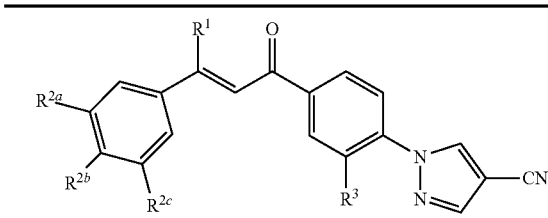

| R$^{2a}$ | R$^{2b}$ | R$^{2c}$ | R[1] | R[3] |
|---|---|---|---|---|
| Cl | H | Cl | CF$_3$ | H |
| Cl | H | Cl | CF$_3$ | Me |
| Cl | H | Cl | CF$_3$ | CN |
| Cl | F | Cl | CF$_3$ | H |

TABLE 9-continued

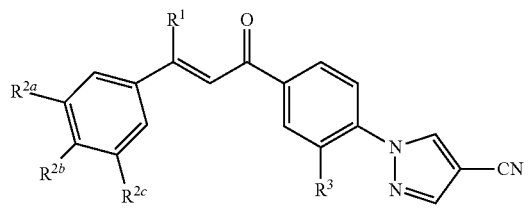

| R2a | R2b | R2c | R1 | R3 |
|---|---|---|---|---|
| Cl | F | Cl | CF3 | Me |
| Cl | F | Cl | CF3 | CN |
| CF3 | H | H | CF3 | H |
| CF3 | H | H | CF3 | Me |
| CF3 | H | H | CF3 | CN |
| CF3 | H | Cl | CF3 | H |
| CF3 | H | Cl | CF3 | Me |
| CF3 | H | Cl | CF3 | CN |
| CF3 | H | CF3 | CF3 | H |
| CF3 | H | CF3 | CF3 | Me |
| CF3 | H | CF3 | CF3 | CN |
| Cl | H | Cl | CF2Cl | H |
| Cl | H | Cl | CF2Cl | Me |
| Cl | H | Cl | CF2Cl | CN |
| Cl | H | Cl | CCl2F | H |
| Cl | H | Cl | CCl2F | Me |
| Cl | Cl | Cl | CF3 | H |
| Cl | Cl | Cl | CF3 | Me |
| Cl | Cl | Cl | CF3 | CN |
| Br | H | Br | CF3 | H |
| Br | H | Br | CF3 | Me |
| Br | H | Br | CF3 | CN |
| CF3 | H | F | CF3 | H |
| CF3 | H | F | CF3 | Me |
| CF3 | H | F | CF3 | CN |
| CF3 | H | Br | CF3 | H |
| CF3 | H | Br | CF3 | Me |
| CF3 | H | Br | CF3 | CN |
| Cl | H | Cl | CCl2F | CN |
| Cl | H | Cl | CF2CF2H | H |
| Cl | H | Cl | CF2CF2H | Me |
| Cl | H | Cl | CF2CF2H | CN |
| Cl | H | Cl | CF2CF3 | H |
| Cl | H | Cl | CF2CF3 | Me |
| Cl | H | Cl | CF2CF3 | CN |

TABLE 10

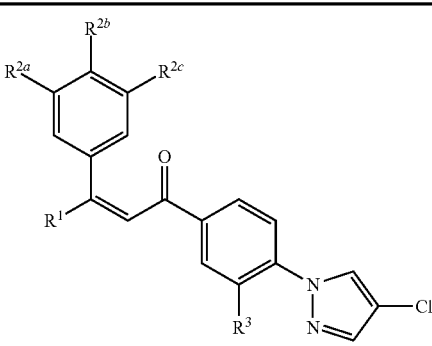

| R2a | R2b | R2c | R1 | R3 |
|---|---|---|---|---|
| Cl | H | Cl | CF3 | H |
| Cl | H | Cl | CF3 | Me |
| Cl | H | Cl | CF3 | CN |
| Cl | F | Cl | CF3 | H |
| Cl | F | Cl | CF3 | Me |
| Cl | F | Cl | CF3 | CN |
| CF3 | H | H | CF3 | H |
| CF3 | H | H | CF3 | Me |

TABLE 10-continued

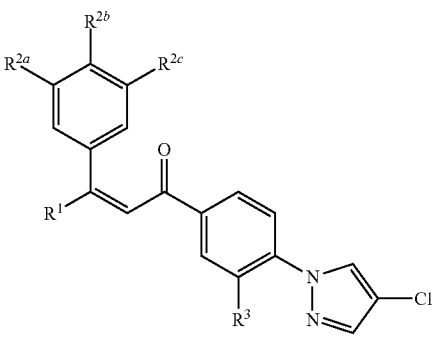

| R2a | R2b | R2c | R1 | R3 |
|---|---|---|---|---|
| CF3 | H | H | CF3 | CN |
| CF3 | H | Cl | CF3 | H |
| CF3 | H | Cl | CF3 | Me |
| CF3 | H | Cl | CF3 | CN |
| CF3 | H | CF3 | CF3 | H |
| CF3 | H | CF3 | CF3 | Me |
| CF3 | H | CF3 | CF3 | CN |
| Cl | H | Cl | CF2Cl | H |
| Cl | H | Cl | CF2Cl | Me |
| Cl | H | Cl | CF2Cl | CN |
| Cl | H | Cl | CCl2F | H |
| Cl | H | Cl | CCl2F | Me |
| Cl | Cl | Cl | CF3 | H |
| Cl | Cl | Cl | CF3 | Me |
| Cl | Cl | Cl | CF3 | CN |
| Br | H | Br | CF3 | H |
| Br | H | Br | CF3 | Me |
| Br | H | Br | CF3 | CN |
| CF3 | H | F | CF3 | H |
| CF3 | H | F | CF3 | Me |
| CF3 | H | F | CF3 | CN |
| CF3 | H | Br | CF3 | H |
| CF3 | H | Br | CF3 | Me |
| CF3 | H | Br | CF3 | CN |
| Cl | H | Cl | CCl2F | CN |
| Cl | H | Cl | CF2CF2H | H |
| Cl | H | Cl | CF2CF2H | Me |
| Cl | H | Cl | CF2CF2H | CN |
| Cl | H | Cl | CF2CF3 | H |
| Cl | H | Cl | CF2CF3 | Me |
| Cl | H | Cl | CF2CF3 | CN |

TABLE 11

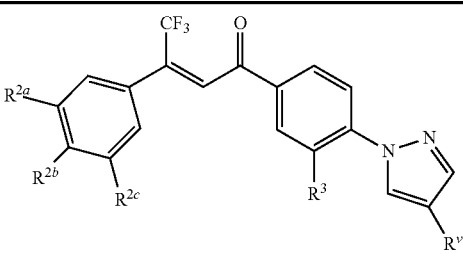

| R2a | R2b | R2c | Rv | R3 |
|---|---|---|---|---|
| Cl | H | Cl | Br | H |
| Cl | H | Cl | Br | Me |
| Cl | H | Cl | Br | CN |
| Cl | Cl | Cl | Br | H |
| Cl | Cl | Cl | Br | CN |
| Cl | Cl | Cl | Br | Me |
| CF3 | H | H | Br | H |
| CF3 | H | H | Br | Me |
| CF3 | H | H | Br | CN |
| CF3 | H | Cl | Br | H |
| CF3 | H | Cl | Br | Me |

TABLE 11-continued

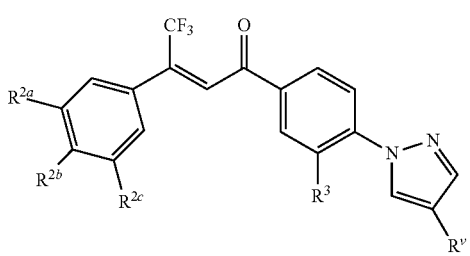

| R2a | R2b | R2c | Rv | R3 |
|---|---|---|---|---|
| CF3 | H | Cl | Br | CN |
| CF3 | H | CF3 | Br | H |
| CF3 | H | CF3 | Br | Me |
| CF3 | H | CF3 | Br | CN |
| Cl | Cl | Cl | CN | H |
| Cl | Cl | Cl | CN | CN |
| Cl | Cl | Cl | CN | Me |
| CF3 | H | H | CN | H |
| CF3 | H | H | CN | Me |
| CF3 | H | H | CN | CN |
| CF3 | H | Cl | CN | H |
| CF3 | H | Cl | CN | Me |
| CF3 | H | Cl | CN | CN |
| CF3 | H | CF3 | CN | H |
| CF3 | H | CF3 | CN | Me |
| CF3 | H | CF3 | CN | CN |
| Cl | F | Cl | Br | H |
| Cl | F | Cl | Br | CN |
| Cl | F | Cl | Br | Me |
| Br | H | Br | Br | H |
| Br | H | Br | Br | Me |
| Br | H | Br | Br | CN |
| CF3 | H | F | Br | H |
| CF3 | H | F | Br | Me |
| CF3 | H | F | Br | CN |
| CF3 | H | Br | Br | H |
| CF3 | H | Br | Br | Me |
| CF3 | H | Br | Br | CN |
| Cl | H | Cl | CN | H |
| Cl | H | Cl | CN | Me |
| Cl | H | Cl | CN | CN |
| Cl | F | Cl | CN | H |
| Cl | F | Cl | CN | CN |
| Cl | F | Cl | CN | Me |
| Br | H | Br | CN | H |
| Br | H | Br | CN | Me |
| Br | H | Br | CN | CN |
| CF3 | H | F | CN | H |
| CF3 | H | F | CN | Me |
| CF3 | H | F | CN | CN |
| CF3 | H | Br | CN | H |
| CF3 | H | Br | CN | Me |
| CF3 | H | Br | CN | CN |

TABLE 12

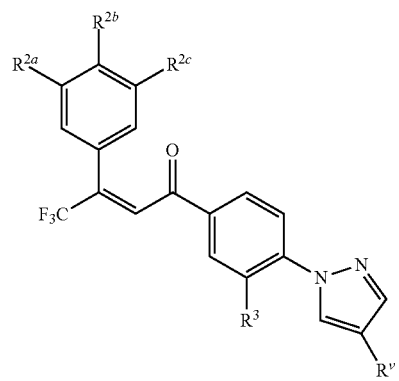

| R2a | R2b | R2c | Rv | R3 |
|---|---|---|---|---|
| Cl | H | Cl | Br | H |
| Cl | H | Cl | Br | Me |
| Cl | H | Cl | Br | CN |
| Cl | Cl | Cl | Br | H |
| Cl | Cl | Cl | Br | CN |
| Cl | Cl | Cl | Br | Me |
| CF3 | H | H | Br | H |
| CF3 | H | H | Br | Me |
| CF3 | H | H | Br | CN |
| CF3 | H | Cl | Br | H |
| CF3 | H | Cl | Br | Me |
| CF3 | H | Cl | Br | CN |
| CF3 | H | CF3 | Br | H |
| CF3 | H | CF3 | Br | Me |
| CF3 | H | CF3 | Br | CN |
| Cl | Cl | Cl | CN | H |
| Cl | Cl | Cl | CN | CN |
| Cl | Cl | Cl | CN | Me |
| CF3 | H | H | CN | H |
| CF3 | H | H | CN | Me |
| CF3 | H | H | CN | CN |
| CF3 | H | Cl | CN | H |
| CF3 | H | Cl | CN | Me |
| CF3 | H | Cl | CN | CN |
| CF3 | H | CF3 | CN | H |
| CF3 | H | CF3 | CN | Me |
| CF3 | H | CF3 | CN | CN |
| Cl | F | Cl | Br | H |
| Cl | F | Cl | Br | CN |
| Cl | F | Cl | Br | Me |
| Br | H | Br | Br | H |
| Br | H | Br | Br | Me |
| Br | H | Br | Br | CN |
| CF3 | H | F | Br | H |
| CF3 | H | F | Br | Me |
| CF3 | H | F | Br | CN |
| CF3 | H | Br | Br | H |
| CF3 | H | Br | Br | Me |
| CF3 | H | Br | Br | CN |
| Cl | H | Cl | CN | H |
| Cl | H | Cl | CN | Me |
| Cl | H | Cl | CN | CN |
| Cl | F | Cl | CN | H |
| Cl | F | Cl | CN | CN |
| Cl | F | Cl | CN | Me |
| Br | H | Br | CN | H |
| Br | H | Br | CN | Me |
| Br | H | Br | CN | CN |
| CF3 | H | F | CN | H |
| CF3 | H | F | CN | Me |
| CF3 | H | F | CN | CN |
| CF3 | H | Br | CN | H |
| CF3 | H | Br | CN | Me |
| CF3 | H | Br | CN | CN |

TABLE 13

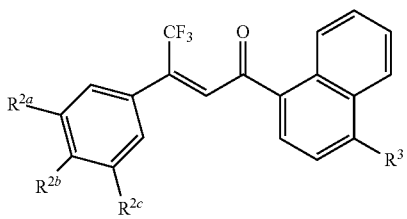

| $R^{2a}$ | $R^{2b}$ | $R^{2c}$ | $R^3$ |
|---|---|---|---|
| Cl | H | Cl | Cl |
| Cl | H | Cl | Br |
| Cl | H | Cl | I |
| Cl | H | Cl | OH |
| Cl | H | Cl | OMe |
| Cl | H | Cl | $OS(O)_2CF_3$ |
| Cl | H | Cl | nitro |
| Cl | H | Cl | $NH_2$ |
| Cl | H | Cl | cyano |
| Cl | H | Cl | Me |
| Cl | H | Cl | $CH_2Cl$ |
| Cl | H | Cl | $CH_2Br$ |
| Cl | H | Cl | $CH_2OH$ |
| Cl | H | Cl | $CH_2OC(O)Me$ |
| Cl | H | Cl | $CO_2H$ |
| Cl | H | Cl | n-Pr |
| Br | H | Br | Cl |
| Br | H | Br | Br |
| Br | H | Br | I |
| Br | H | Br | OH |
| Br | H | Br | OMe |
| Br | H | Br | $OS(O)_2CF_3$ |
| Br | H | Br | nitro |
| Br | H | Br | $NH_2$ |
| Br | H | Br | cyano |
| Br | H | Br | Me |
| Br | H | Br | $CH_2Cl$ |
| Br | H | Br | $CH_2Br$ |
| Br | H | Br | $CH_2OH$ |
| Br | H | Br | $CH_2OC(O)Me$ |
| Br | H | Br | $CO_2H$ |
| Br | H | Br | n-Pr |
| $CF_3$ | H | H | Cl |
| $CF_3$ | H | H | Br |
| $CF_3$ | H | H | I |
| $CF_3$ | H | H | OH |
| $CF_3$ | H | H | OMe |
| $CF_3$ | H | H | $OS(O)_2CF_3$ |
| $CF_3$ | H | H | nitro |
| $CF_3$ | H | H | $NH_2$ |
| $CF_3$ | H | H | cyano |
| $CF_3$ | H | H | Me |
| $CF_3$ | H | H | $CH_2Cl$ |
| $CF_3$ | H | H | $CH_2Br$ |
| $CF_3$ | H | H | $CH_2OH$ |
| $CF_3$ | H | H | $CH_2OC(O)Me$ |
| $CF_3$ | H | H | $CO_2H$ |
| $CF_3$ | H | H | n-Pr |
| $CF_3$ | H | F | Cl |
| $CF_3$ | H | F | Br |
| $CF_3$ | H | F | I |
| $CF_3$ | H | F | OH |
| $CF_3$ | H | F | OMe |
| $CF_3$ | H | F | $OS(O)_2CF_3$ |
| $CF_3$ | H | F | nitro |
| $CF_3$ | H | F | $NH_2$ |
| $CF_3$ | H | F | cyano |
| $CF_3$ | H | F | Me |
| $CF_3$ | H | F | $CH_2Cl$ |
| $CF_3$ | H | F | $CH_2Br$ |
| $CF_3$ | H | F | $CH_2OH$ |
| $CF_3$ | H | F | $CH_2OC(O)Me$ |
| $CF_3$ | H | F | $CO_2H$ |
| $CF_3$ | H | F | n-Pr |
| $CF_3$ | H | Br | Cl |
| $CF_3$ | H | Br | Br |
| $CF_3$ | H | Br | I |

TABLE 13-continued

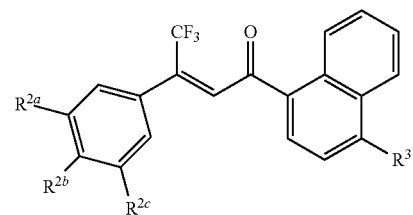

| $R^{2a}$ | $R^{2b}$ | $R^{2c}$ | $R^3$ |
|---|---|---|---|
| $CF_3$ | H | Br | OH |
| $CF_3$ | H | Br | OMe |
| $CF_3$ | H | Br | $OS(O)_2CF_3$ |
| $CF_3$ | H | Br | nitro |
| $CF_3$ | H | Br | $NH_2$ |
| $CF_3$ | H | Br | cyano |
| $CF_3$ | H | Br | Me |
| $CF_3$ | H | Br | $CH_2Cl$ |
| $CF_3$ | H | Br | $CH_2Br$ |
| $CF_3$ | H | Br | $CH_2OH$ |
| $CF_3$ | H | Br | $CH_2OC(O)Me$ |
| $CF_3$ | H | Br | $CO_2H$ |
| $CF_3$ | H | Br | n-Pr |
| $OCH_2CF_3$ | H | F | Cl |
| $OCH_2CF_3$ | H | F | Br |
| $OCH_2CF_3$ | H | F | I |
| $OCH_2CF_3$ | H | F | OH |
| $OCH_2CF_3$ | H | F | OMe |
| $OCH_2CF_3$ | H | F | $OS(O)_2CF_3$ |
| $OCH_2CF_3$ | H | F | nitro |
| $OCH_2CF_3$ | H | F | $NH_2$ |
| $OCH_2CF_3$ | H | F | cyano |
| $OCH_2CF_3$ | H | F | Me |
| $OCH_2CF_3$ | H | F | $CH_2Cl$ |
| $OCH_2CF_3$ | H | F | $CH_2Br$ |
| $OCH_2CF_3$ | H | F | $CH_2OH$ |
| $OCH_2CF_3$ | H | F | $CH_2OC(O)Me$ |
| $OCH_2CF_3$ | H | F | $CO_2H$ |
| $OCH_2CF_3$ | H | F | n-Pr |
| $OCH_2CF_3$ | H | Br | Cl |
| $OCH_2CF_3$ | H | Br | Br |
| $OCH_2CF_3$ | H | Br | I |
| $OCH_2CF_3$ | H | Br | OH |
| $OCH_2CF_3$ | H | Br | OMe |
| $OCH_2CF_3$ | H | Br | $OS(O)_2CF_3$ |
| $OCH_2CF_3$ | H | Br | nitro |
| $OCH_2CF_3$ | H | Br | $NH_2$ |
| $CF_3$ | H | Cl | Cl |
| $CF_3$ | H | Cl | Br |
| $CF_3$ | H | Cl | I |
| $CF_3$ | H | Cl | OH |
| $CF_3$ | H | Cl | OMe |
| $CF_3$ | H | Cl | $OS(O)_2CF_3$ |
| $CF_3$ | H | Cl | nitro |
| $CF_3$ | H | Cl | $NH_2$ |
| $CF_3$ | H | Cl | cyano |
| $CF_3$ | H | Cl | Me |
| $CF_3$ | H | Cl | $CH_2Cl$ |
| $CF_3$ | H | Cl | $CH_2Br$ |
| $CF_3$ | H | Cl | $CH_2OH$ |
| $CF_3$ | H | Cl | $CH_2OC(O)Me$ |
| $CF_3$ | H | Cl | $CO_2H$ |
| $CF_3$ | H | Cl | n-Pr |
| $CF_3$ | H | $CF_3$ | Cl |
| $CF_3$ | H | $CF_3$ | Br |
| $CF_3$ | H | $CF_3$ | I |
| $CF_3$ | H | $CF_3$ | OH |
| $CF_3$ | H | $CF_3$ | OMe |
| $CF_3$ | H | $CF_3$ | $OS(O)_2CF_3$ |
| $CF_3$ | H | $CF_3$ | nitro |
| $CF_3$ | H | $CF_3$ | $NH_2$ |
| $CF_3$ | H | $CF_3$ | cyano |
| $CF_3$ | H | $CF_3$ | Me |
| $CF_3$ | H | $CF_3$ | $CH_2Cl$ |
| $CF_3$ | H | $CF_3$ | $CH_2Br$ |
| $CF_3$ | H | $CF_3$ | $CH_2OH$ |
| $CF_3$ | H | $CF_3$ | $CH_2OC(O)Me$ |

TABLE 13-continued

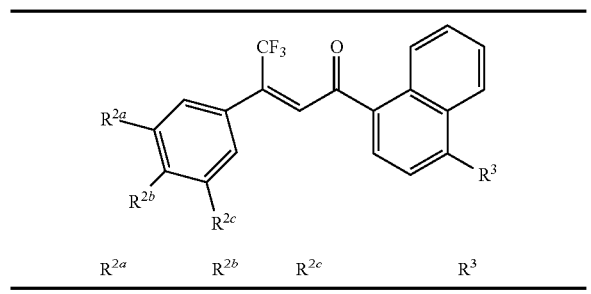

| R²ᵃ | R²ᵇ | R²ᶜ | R³ |
|---|---|---|---|
| CF₃ | H | CF₃ | CO₂H |
| CF₃ | H | CF₃ | n-Pr |
| Cl | Cl | Cl | Cl |
| Cl | Cl | Cl | Br |
| Cl | Cl | Cl | I |
| Cl | Cl | Cl | OH |
| Cl | Cl | Cl | OMe |
| Cl | Cl | Cl | OS(O)₂CF₃ |
| Cl | Cl | Cl | nitro |
| Cl | Cl | Cl | NH₂ |
| Cl | Cl | Cl | cyano |
| Cl | Cl | Cl | Me |
| Cl | Cl | Cl | CH₂Cl |
| Cl | Cl | Cl | CH₂Br |
| Cl | Cl | Cl | CH₂OH |
| Cl | Cl | Cl | CH₂OC(O)Me |
| Cl | Cl | Cl | CO₂H |
| Cl | Cl | Cl | n-Pr |
| Cl | F | Cl | Cl |
| Cl | F | Cl | Br |
| Cl | F | Cl | I |
| Cl | F | Cl | OH |
| Cl | F | Cl | OMe |
| Cl | F | Cl | OS(O)₂CF₃ |
| Cl | F | Cl | nitro |
| Cl | F | Cl | NH₂ |
| Cl | F | Cl | cyano |
| Cl | F | Cl | Me |
| Cl | F | Cl | CH₂Cl |
| Cl | F | Cl | CH₂Br |
| Cl | F | Cl | CH₂OH |
| Cl | F | Cl | CH₂OC(O)Me |
| Cl | F | Cl | CO₂H |
| Cl | F | Cl | n-Pr |
| OCF₃ | H | Cl | Cl |
| OCF₃ | H | Cl | Br |
| OCF₃ | H | Cl | I |
| OCF₃ | H | Cl | OH |
| OCF₃ | H | Cl | OMe |
| OCF₃ | H | Cl | OS(O)₂CF₃ |
| OCF₃ | H | Cl | nitro |
| OCF₃ | H | Cl | NH₂ |
| OCF₃ | H | Cl | cyano |
| OCF₃ | H | Cl | Me |
| OCF₃ | H | Cl | CH₂Cl |
| OCF₃ | H | Cl | CH₂Br |
| OCF₃ | H | Cl | CH₂OH |
| OCF₃ | H | Cl | CH₂OC(O)Me |
| OCF₃ | H | Cl | CO₂H |
| OCF₃ | H | Cl | n-Pr |
| OCH₂CF₃ | H | Cl | Cl |
| OCH₂CF₃ | H | Cl | Br |
| OCH₂CF₃ | H | Cl | I |
| OCH₂CF₃ | H | Cl | OH |
| OCH₂CF₃ | H | Cl | OMe |
| OCH₂CF₃ | H | Cl | OS(O)₂CF₃ |
| OCH₂CF₃ | H | Cl | nitro |
| OCH₂CF₃ | H | Cl | NH₂ |
| OCH₂CF₃ | H | Cl | cyano |
| OCH₂CF₃ | H | Cl | Me |
| OCH₂CF₃ | H | Cl | CH₂Cl |
| OCH₂CF₃ | H | Cl | CH₂Br |
| OCH₂CF₃ | H | Cl | CH₂OH |
| OCH₂CF₃ | H | Cl | CH₂OC(O)Me |
| OCH₂CF₃ | H | Cl | CO₂H |
| OCH₂CF₃ | H | Cl | n-Pr |
| OCH₂CF₃ | H | Br | cyano |
| OCH₂CF₃ | H | Br | Me |
| OCH₂CF₃ | H | Br | CH₂Cl |
| OCH₂CF₃ | H | Br | CH₂Br |
| OCH₂CF₃ | H | Br | CH₂OH |
| OCH₂CF₃ | H | Br | CH₂OC(O)Me |
| OCH₂CF₃ | H | Br | CO₂H |
| OCH₂CF₃ | H | Br | n-Pr |

TABLE 14

| R²ᵃ | R²ᵇ | R²ᶜ | R³ |
|---|---|---|---|
| Cl | H | Cl | Cl |
| Cl | H | Cl | Br |
| Cl | H | Cl | I |
| Cl | H | Cl | OH |
| Cl | H | Cl | OMe |
| Cl | H | Cl | OS(O)₂CF₃ |
| Cl | H | Cl | nitro |
| Cl | H | Cl | NH₂ |
| Cl | H | Cl | cyano |
| Cl | H | Cl | Me |
| Cl | H | Cl | CH₂Cl |
| Cl | H | Cl | CH₂Br |
| Cl | H | Cl | CH₂OH |
| Cl | H | Cl | CH₂OC(O)Me |
| Cl | H | Cl | CO₂H |
| Cl | H | Cl | n-Pr |
| Br | H | Br | Cl |
| Br | H | Br | Br |
| Br | H | Br | I |
| Br | H | Br | OH |
| Br | H | Br | OMe |
| Br | H | Br | OS(O)₂CF₃ |
| Br | H | Br | nitro |
| Br | H | Br | NH₂ |
| Br | H | Br | cyano |
| Br | H | Br | Me |
| Br | H | Br | CH₂Cl |
| Br | H | Br | CH₂Br |
| Br | H | Br | CH₂OH |
| Br | H | Br | CH₂OC(O)Me |
| Br | H | Br | CO₂H |
| Br | H | Br | n-Pr |
| CF₃ | H | H | Cl |
| CF₃ | H | H | Br |
| CF₃ | H | H | I |
| CF₃ | H | H | OH |
| CF₃ | H | H | OMe |
| CF₃ | H | H | OS(O)₂CF₃ |

TABLE 14-continued

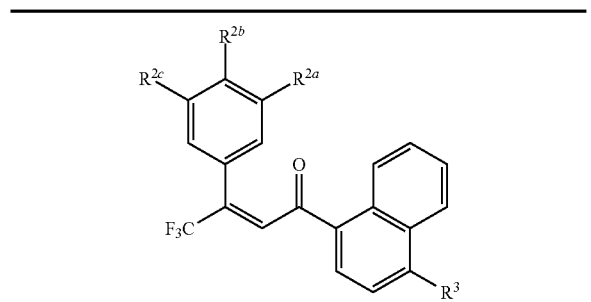
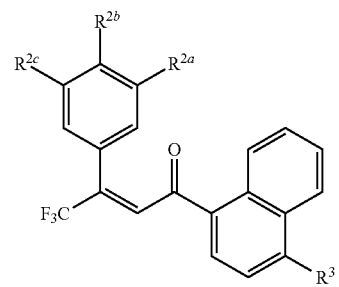

| $R^{2a}$ | $R^{2b}$ | $R^{2c}$ | $R^3$ |
|---|---|---|---|
| $CF_3$ | H | H | nitro |
| $CF_3$ | H | H | $NH_2$ |
| $CF_3$ | H | H | cyano |
| $CF_3$ | H | H | Me |
| $CF_3$ | H | H | $CH_2Cl$ |
| $CF_3$ | H | H | $CH_2Br$ |
| $CF_3$ | H | H | $CH_2OH$ |
| $CF_3$ | H | H | $CH_2OC(O)Me$ |
| $CF_3$ | H | H | $CO_2H$ |
| $CF_3$ | H | H | n-Pr |
| $CF_3$ | H | F | Cl |
| $CF_3$ | H | F | Br |
| $CF_3$ | H | F | I |
| $CF_3$ | H | F | OH |
| $CF_3$ | H | F | OMe |
| $CF_3$ | H | F | $OS(O)_2CF_3$ |
| $CF_3$ | H | F | nitro |
| $CF_3$ | H | F | $NH_2$ |
| $CF_3$ | H | F | cyano |
| $CF_3$ | H | F | Me |
| $CF_3$ | H | F | $CH_2Cl$ |
| $CF_3$ | H | F | $CH_2Br$ |
| $CF_3$ | H | F | $CH_2OH$ |
| $CF_3$ | H | F | $CH_2OC(O)Me$ |
| $CF_3$ | H | F | $CO_2H$ |
| $CF_3$ | H | F | n-Pr |
| $CF_3$ | H | Br | Cl |
| $CF_3$ | H | Br | Br |
| $CF_3$ | H | Br | I |
| $CF_3$ | H | Br | OH |
| $CF_3$ | H | Br | OMe |
| $CF_3$ | H | Br | $OS(O)_2CF_3$ |
| $CF_3$ | H | Br | nitro |
| $CF_3$ | H | Br | $NH_2$ |
| $CF_3$ | H | Br | cyano |
| $CF_3$ | H | Br | Me |
| $CF_3$ | H | Br | $CH_2Cl$ |
| $CF_3$ | H | Br | $CH_2Br$ |
| $CF_3$ | H | Br | $CH_2OH$ |
| $CF_3$ | H | Br | $CH_2OC(O)Me$ |
| $CF_3$ | H | Br | $CO_2H$ |
| $CF_3$ | H | Br | n-Pr |
| $OCH_2CF_3$ | H | F | Cl |
| $OCH_2CF_3$ | H | F | Br |
| $OCH_2CF_3$ | H | F | I |
| $OCH_2CF_3$ | H | F | OH |
| $OCH_2CF_3$ | H | F | OMe |
| $OCH_2CF_3$ | H | F | $OS(O)_2CF_3$ |
| $OCH_2CF_3$ | H | F | nitro |
| $OCH_2CF_3$ | H | F | $NH_2$ |
| $OCH_2CF_3$ | H | F | cyano |
| $OCH_2CF_3$ | H | F | Me |
| $OCH_2CF_3$ | H | F | $CH_2Cl$ |
| $OCH_2CF_3$ | H | F | $CH_2Br$ |
| $OCH_2CF_3$ | H | F | $CH_2OH$ |
| $OCH_2CF_3$ | H | F | $CH_2OC(O)Me$ |
| $OCH_2CF_3$ | H | F | $CO_2H$ |
| $OCH_2CF_3$ | H | F | n-Pr |
| $OCH_2CF_3$ | H | Br | Cl |
| $OCH_2CF_3$ | H | Br | Br |
| $OCH_2CF_3$ | H | Br | I |
| $OCH_2CF_3$ | H | Br | OH |
| $OCH_2CF_3$ | H | Br | OMe |
| $OCH_2CF_3$ | H | Br | $OS(O)_2CF_3$ |
| $OCH_2CF_3$ | H | Br | nitro |
| $OCH_2CF_3$ | H | Br | $NH_2$ |
| $CF_3$ | H | Cl | Cl |
| $CF_3$ | H | Cl | Br |
| $CF_3$ | H | Cl | I |
| $CF_3$ | H | Cl | OH |
| $CF_3$ | H | Cl | OMe |
| $CF_3$ | H | Cl | $OS(O)_2CF_3$ |
| $CF_3$ | H | Cl | nitro |
| $CF_3$ | H | Cl | $NH_2$ |
| $CF_3$ | H | Cl | cyano |
| $CF_3$ | H | Cl | Me |
| $CF_3$ | H | Cl | $CH_2Cl$ |
| $CF_3$ | H | Cl | $CH_2Br$ |
| $CF_3$ | H | Cl | $CH_2OH$ |
| $CF_3$ | H | Cl | $CH_2OC(O)Me$ |
| $CF_3$ | H | Cl | $CO_2H$ |
| $CF_3$ | H | Cl | n-Pr |
| $CF_3$ | H | $CF_3$ | Cl |
| $CF_3$ | H | $CF_3$ | Br |
| $CF_3$ | H | $CF_3$ | I |
| $CF_3$ | H | $CF_3$ | OH |
| $CF_3$ | H | $CF_3$ | OMe |
| $CF_3$ | H | $CF_3$ | $OS(O)_2CF_3$ |
| $CF_3$ | H | $CF_3$ | nitro |
| $CF_3$ | H | $CF_3$ | $NH_2$ |
| $CF_3$ | H | $CF_3$ | cyano |
| $CF_3$ | H | $CF_3$ | Me |
| $CF_3$ | H | $CF_3$ | $CH_2Cl$ |
| $CF_3$ | H | $CF_3$ | $CH_2Br$ |
| $CF_3$ | H | $CF_3$ | $CH_2OH$ |
| $CF_3$ | H | $CF_3$ | $CH_2OC(O)Me$ |
| $CF_3$ | H | $CF_3$ | $CO_2H$ |
| $CF_3$ | H | $CF_3$ | n-Pr |
| Cl | Cl | Cl | Cl |
| Cl | Cl | Cl | Br |
| Cl | Cl | Cl | I |
| Cl | Cl | Cl | OH |
| Cl | Cl | Cl | OMe |
| Cl | Cl | Cl | $OS(O)_2CF_3$ |
| Cl | Cl | Cl | nitro |
| Cl | Cl | Cl | $NH_2$ |
| Cl | Cl | Cl | cyano |
| Cl | Cl | Cl | Me |
| Cl | Cl | Cl | $CH_2Cl$ |
| Cl | Cl | Cl | $CH_2Br$ |
| Cl | Cl | Cl | $CH_2OH$ |
| Cl | Cl | Cl | $CH_2OC(O)Me$ |
| Cl | Cl | Cl | $CO_2H$ |
| Cl | Cl | Cl | n-Pr |
| Cl | F | Cl | Cl |
| Cl | F | Cl | Br |
| Cl | F | Cl | I |
| Cl | F | Cl | OH |
| Cl | F | Cl | OMe |
| Cl | F | Cl | $OS(O)_2CF_3$ |
| Cl | F | Cl | nitro |
| Cl | F | Cl | $NH_2$ |
| Cl | F | Cl | cyano |
| Cl | F | Cl | Me |
| Cl | F | Cl | $CH_2Cl$ |
| Cl | F | Cl | $CH_2Br$ |

TABLE 14-continued

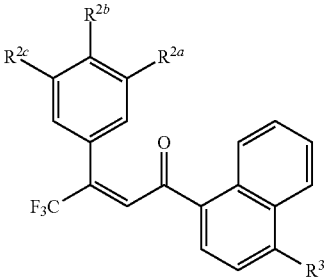

| R2a | R2b | R2c | R3 |
|---|---|---|---|
| Cl | F | Cl | CH$_2$OH |
| Cl | F | Cl | CH$_2$OC(O)Me |
| Cl | F | Cl | CO$_2$H |
| Cl | F | Cl | n-Pr |
| OCF$_3$ | H | Cl | Cl |
| OCF$_3$ | H | Cl | Br |
| OCF$_3$ | H | Cl | I |
| OCF$_3$ | H | Cl | OH |
| OCF$_3$ | H | Cl | OMe |
| OCF$_3$ | H | Cl | OS(O)$_2$CF$_3$ |
| OCF$_3$ | H | Cl | nitro |
| OCF$_3$ | H | Cl | NH$_2$ |
| OCF$_3$ | H | Cl | cyano |
| OCF$_3$ | H | Cl | Me |
| OCF$_3$ | H | Cl | CH$_2$Cl |
| OCF$_3$ | H | Cl | CH$_2$Br |
| OCF$_3$ | H | Cl | CH$_2$OH |
| OCF$_3$ | H | Cl | CH$_2$OC(O)Me |
| OCF$_3$ | H | Cl | CO$_2$H |
| OCF$_3$ | H | Cl | n-Pr |
| OCH$_2$CF$_3$ | H | Cl | Cl |
| OCH$_2$CF$_3$ | H | Cl | Br |
| OCH$_2$CF$_3$ | H | Cl | I |
| OCH$_2$CF$_3$ | H | Cl | OH |
| OCH$_2$CF$_3$ | H | Cl | OMe |
| OCH$_2$CF$_3$ | H | Cl | OS(O)$_2$CF$_3$ |
| OCH$_2$CF$_3$ | H | Cl | nitro |
| OCH$_2$CF$_3$ | H | Cl | NH$_2$ |
| OCH$_2$CF$_3$ | H | Cl | cyano |
| OCH$_2$CF$_3$ | H | Cl | Me |
| OCH$_2$CF$_3$ | H | Cl | CH$_2$Cl |
| OCH$_2$CF$_3$ | H | Cl | CH$_2$Br |
| OCH$_2$CF$_3$ | H | Cl | CH$_2$OH |
| OCH$_2$CF$_3$ | H | Cl | CH$_2$OC(O)Me |
| OCH$_2$CF$_3$ | H | Cl | CO$_2$H |
| OCH$_2$CF$_3$ | H | Cl | n-Pr |
| OCH$_2$CF$_3$ | H | Br | cyano |
| OCH$_2$CF$_3$ | H | Br | Me |
| OCH$_2$CF$_3$ | H | Br | CH$_2$Cl |
| OCH$_2$CF$_3$ | H | Br | CH$_2$Br |
| OCH$_2$CF$_3$ | H | Br | CH$_2$OH |
| OCH$_2$CF$_3$ | H | Br | CH$_2$OC(O)Me |
| OCH$_2$CF$_3$ | H | Br | CO$_2$H |
| OCH$_2$CF$_3$ | H | Br | n-Pr |

What is claimed is:
1. A method for preparing a compound of Formula 1

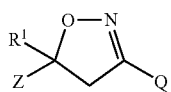

wherein
$R^1$ is CHX$_2$, CX$_3$, CX$_2$CHX$_2$ or CX$_2$CX$_3$;
each X is independently Cl or F;
Z is optionally substituted phenyl;
Q is $Q^a$ or $Q^b$;

$Q^a$ is phenyl substituted with one $Q^1$ and optionally substituted with one to four substituents independently selected from $R^3$;

$Q^1$ is a phenyl ring or a 5- or 6-membered saturated or unsaturated heterocyclic ring, each ring optionally substituted with one or more substituents independently selected from halogen, C$_1$-C$_6$ alkyl, C$_1$-C$_6$ haloalkyl, C$_3$-C$_6$ cycloalkyl, C$_3$-C$_6$ halocycloalkyl, C$_1$-C$_6$ alkoxy, C$_1$-C$_6$ haloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, —CN, —NO$_2$, —N(R$^4$)R$^5$, —C(=W)N(R$^4$)R$^5$, —C(=O)OR$^5$ and R$^7$;

$Q^b$ is optionally substituted 1-naphthalenyl;

each $R^3$ is independently halogen, C$_1$-C$_6$ alkyl, C$_1$-C$_6$ haloalkyl, C$_2$-C$_6$ alkenyl, C$_2$-C$_6$ haloalkenyl, C$_2$-C$_6$ alkynyl, C$_3$-C$_6$ haloalkynyl, C$_3$-C$_6$ cycloalkyl, C$_3$-C$_6$ halocycloalkyl, C$_1$-C$_6$ alkoxy, C$_1$-C$_6$ haloalkoxy, C$_1$-C$_6$ alkylthio, C$_2$-C$_7$ alkylcarbonyl, C$_2$-C$_7$ haloalkylcarbonyl, C$_1$-C$_6$ haloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, —N(R$^4$)R$^5$, —C(=W)N(R$^4$)R$^5$, —C(=W)OR$^5$, —CN, —OR$^{11}$ or —NO$_2$; or a phenyl ring or a 5- or 6-membered saturated or unsaturated heterocyclic ring, each ring optionally substituted with one or more substituents independently selected from halogen, C$_1$-C$_6$ alkyl, C$_1$-C$_6$ haloalkyl, C$_3$-C$_6$ cycloalkyl, C$_3$-C$_6$ halocycloalkyl, C$_1$-C$_6$ alkoxy, C$_1$-C$_6$ haloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, —CN, —NO$_2$, —N(R$^4$)R$^5$, —C(=W)N(R$^4$)R$^5$, —C(=O)OR$^5$ and R$^7$;

each $R^4$ is independently H, C$_1$-C$_6$ alkyl, C$_2$-C$_6$ alkenyl, C$_2$-C$_6$ alkynyl, C$_3$-C$_6$ cycloalkyl, C$_4$-C$_7$ alkylcycloalkyl, C$_4$-C$_7$ cycloalkylalkyl, C$_2$-C$_7$ alkylcarbonyl or C$_2$-C$_7$ alkoxycarbonyl;

each $R^5$ is independently H; or C$_1$-C$_6$ alkyl, C$_2$-C$_6$ alkenyl, C$_2$-C$_6$ alkynyl, C$_3$-C$_6$ cycloalkyl, C$_4$-C$_7$ alkylcycloalkyl or C$_4$-C$_7$ cycloalkylalkyl, each optionally substituted with one or more substituents independently selected from R$^6$;

each $R^6$ is independently halogen, C$_1$-C$_6$ alkyl, C$_1$-C$_6$ alkoxy, C$_1$-C$_6$ alkylthio, C$_1$-C$_6$ alkylsulfinyl, C$_1$-C$_6$ alkylsulfonyl, C$_1$-C$_6$ alkylamino, C$_2$-C$_8$ dialkylamino, C$_3$-C$_6$ cycloalkylamino, C$_2$-C$_7$ alkylcarbonyl, C$_2$-C$_7$ alkoxycarbonyl, C$_2$-C$_7$ alkylaminocarbonyl, C$_3$-C$_9$ dialkylaminocarbonyl, C$_2$-C$_7$ haloalkylcarbonyl, C$_2$-C$_7$ haloalkoxycarbonyl, C$_2$-C$_7$ haloalkylaminocarbonyl, C$_3$-C$_9$ halodialkylaminocarbonyl, —OH, —NH$_2$, —CN or —NO$_2$; or Q$^2$;

each $R^7$ is independently a phenyl ring or a pyridinyl ring, each ring optionally substituted with one or more substituents independently selected from R$^8$;

each $R^8$ is independently halogen, C$_1$-C$_6$ alkyl, C$_1$-C$_6$ haloalkyl, C$_1$-C$_6$ alkoxy, C$_1$-C$_6$ haloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, C$_1$-C$_6$ alkylamino, C$_2$-C$_6$ dialkylamino, C$_2$-C$_4$ alkylcarbonyl, C$_2$-C$_4$ alkoxycarbonyl, C$_2$-C$_7$ alkylaminocarbonyl, C$_3$-C$_7$ dialkylaminocarbonyl, —OH, —NH$_2$, —C(=O)OH, —CN or —NO$_2$;

each $Q^2$ is independently a phenyl ring or a 5- or 6-membered saturated or unsaturated heterocyclic ring, each ring optionally substituted with one or more substituents independently selected from halogen, C$_1$-C$_6$ alkyl, C$_1$-C$_6$ haloalkyl, C$_3$-C$_6$ cycloalkyl, C$_3$-C$_6$ halocycloalkyl, C$_1$-C$_6$ alkoxy, C$_1$-C$_6$ haloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —$NO_2$, —C(=W)N($R^9$)$R^{10}$ and —C(=O)O$R^{10}$;

each $R^9$ is independently H, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

each $R^{10}$ is independently H; or $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl;

each $R^{11}$ is independently H; or $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl, $C_2$-$C_7$ alkoxycarbonyl, $C_1$-$C_6$ alkylsulfonyl or $C_1$-$C_6$ haloalkylsulfonyl; and each W is independently O or S;

comprising contacting a compound of Formula 2

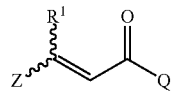

2 wherein $R^1$, Q and Z are as previously defined for Formula 1, with hydroxylamine in the presence of a base.

2. The method of claim 1 wherein

Z is phenyl optionally substituted with one to five substituents independently selected from $R^2$; and each $R^2$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylamino, $C_2$-$C_6$ dialkylamino, —CN or —$NO_2$.

3. The method of claim 2 wherein $R^1$ is $CF_3$;

Z is phenyl substituted with one to three substituents independently selected from $R^2$, said substituents attached at the 3-, 4- or 5-positions of the phenyl ring; and each $R^2$ is independently halogen, $C_1$-$C_3$ alkyl, $C_1$-$C_3$ haloalkyl, $C_1$-$C_3$ haloalkoxy or —CN.

4. The method of claim 3 wherein

Q is $Q^a$.

5. The method of claim 4 wherein $Q^a$ is phenyl substituted with one $Q^1$ attached at the 4-position of the phenyl ring, said phenyl ring further optionally substituted with one or two substituents independently selected from $R^3$;

$Q^1$ is a 5-membered heteroaromatic ring optionally substituted with one or two substituents independently selected from halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, —CN, —C(=W)N($R^4$)$R^5$ and —C(=O)O$R^5$; and each $R^3$ is independently halogen, $C_1$-$C_6$ alkyl or —CN.

6. The method of claim 5 wherein $Q^1$ is a pyrazole or triazole ring optionally substituted with one or two substituents independently selected from halogen, —CN and —C(=W)N($R^4$)$R^5$;

one $R^3$ is Cl, $CH_3$ or —CN and is attached at the 3-position of the phenyl ring adjacent to $Q^1$;

$R^4$ is H; and $R^5$ is H; or $C_1$-$C_3$ alkyl, cyclopropyl or cyclopropylmethyl, each optionally substituted with halogen and further optionally substituted with 1 or 2 $CH_3$.

7. The method of claim 3 wherein

Q is $Q^b$.

8. The method of claim 7 wherein $Q^b$ is 1-naphthalenyl substituted with one or two substituents independently selected from $R^3$.

9. The method of claim 8 wherein one $R^3$ is halogen, $C_1$-$C_6$ alkyl, $C_1$-$C_6$ haloalkyl, $C_1$-$C_6$ alkoxy, —N($R^4$)$R^5$, —C(=W)N($R^4$)$R^5$, —C(=W)O$R^5$, —CN, —O$R^{11}$ or —$NO_2$, and said $R^3$ is attached at the 4-position of the naphthalene ring;

each $R^4$ is independently H, $C_1$-$C_6$ alkyl, $C_2$-$C_7$ alkylcarbonyl or $C_2$-$C_7$ alkoxycarbonyl;

$R^5$ is $C_1$-$C_6$ alkyl substituted with one substituent selected from hydroxy, $C_1$-$C_6$ alkoxy, $C_1$-$C_6$ alkylthio, $C_1$-$C_6$ alkylsulfinyl, $C_1$-$C_6$ alkylsulfonyl, $C_2$-$C_7$ alkylaminocarbonyl, $C_3$-$C_9$ dialkylaminocarbonyl, $C_2$-$C_7$ haloalkylaminocarbonyl, $C_3$-$C_9$ halodialkylaminocarbonyl and $Q^2$;

$Q^2$ is a pyridinyl ring optionally substituted with one to four halogen; and $R^{11}$ is H, $C_2$-$C_6$ alkenyl, $C_2$-$C_6$ alkynyl, $C_2$-$C_7$ alkylcarbonyl, $C_2$-$C_7$ alkoxycarbonyl, $C_1$-$C_6$ alkylsulfonyl or $C_1$-$C_6$ haloalkylsulfonyl.

10. The method of claim 9 wherein $Q^b$ is 1-naphthalenyl substituted with one $R^3$ attached at the 4-position of the naphthalene ring;

$R^3$ is —C(=O)N($R^4$)$R^5$;

$R^4$ is H; and $R^5$ is $C_1$-$C_2$ alkyl substituted with $C_2$-$C_7$ haloalkylaminocarbonyl.

11. The method of claim 1 wherein the hydroxylamine is derived from a hydroxylamine salt.

12. The method of claim 11 wherein the hydroxylamine salt is a hydroxylamine salt of hydrochloric acid, sulfuric acid, phosphoric acid, or a mixture thereof.

13. The method of claim 1 wherein the base comprises one or more compounds selected from amine bases, alkali metal hydroxide bases, alkali metal alkoxide bases and alkali metal carbonate bases.

14. The method of claim 13 wherein the base comprises sodium carbonate, potassium carbonate, or a mixture thereof.

15. The method of claim 13 wherein the base comprises sodium hydroxide, potassium hydroxide, or a mixture thereof.

16. The method of claim 1 wherein the compound of Formula 2 is 4-[3-[3-chloro-5-(trifluoromethyl)phenyl]-4,4,4-trifluoro-1-oxo-2-buten-1-yl]-N-[2-oxo-2-[(2,2,2-trifluoroethyl)amino]ethyl]-1-naphthalenecarboxamide.

17. The method of claim 10 wherein $R^5$ is $CH_2C(O)NHCH_2CF_3$.

* * * * *